United States Patent
Harwin et al.

(10) Patent No.: US 12,304,956 B1
(45) Date of Patent: *May 20, 2025

(54) DOSING REGIMEN FOR TREATING INFLAMMATORY BOWEL DISEASE

(71) Applicant: Paragon Therapeutics, Inc., Waltham, MA (US)

(72) Inventors: Peter Evan Harwin, Dorado, PR (US); Tomas Kiselak, Dorado, PR (US); Hussam Hisham Shaheen, Auburn, NH (US); Eric Franklin Zhu, Cambridge, MA (US)

(73) Assignee: Paragon Therapeutics, Inc., Waltham, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/774,123

(22) Filed: Jul. 16, 2024

Related U.S. Application Data

(63) Continuation of application No. PCT/US2024/031569, filed on May 30, 2024.

(60) Provisional application No. 63/559,081, filed on Feb. 28, 2024, provisional application No. 63/554,886, filed on Feb. 16, 2024, provisional application No. 63/599,922, filed on Nov. 16, 2023, provisional application No. 63/505,962, filed on Jun. 2, 2023, provisional application No. 63/504,966, filed on May 30, 2023.

(51) Int. Cl.
| | | |
|---|---|---|
| *C07K 16/28* | (2006.01) | |
| *A61K 9/00* | (2006.01) | |
| *A61K 47/18* | (2017.01) | |
| *A61K 47/26* | (2006.01) | |
| *A61P 1/00* | (2006.01) | |
| *A61K 39/00* | (2006.01) | |

(52) U.S. Cl.
CPC ........ *C07K 16/2839* (2013.01); *A61K 9/0019* (2013.01); *A61K 47/183* (2013.01); *A61K 47/26* (2013.01); *A61P 1/00* (2018.01); *A61K 2039/505* (2013.01); *A61K 2039/545* (2013.01)

(58) Field of Classification Search
None
See application file for complete search history.

(56) References Cited

U.S. PATENT DOCUMENTS

| | | | |
|---|---|---|---|
| 5,811,523 A | 9/1998 | Trinchieri et al. | |
| 5,840,299 A | 11/1998 | Bendig et al. | |
| 7,083,784 B2 | 8/2006 | Dall'Acqua et al. | |
| 7,090,845 B2 | 8/2006 | Fong et al. | |
| 7,147,851 B1 | 12/2006 | Ponath et al. | |
| 7,211,252 B2 | 5/2007 | Mundy et al. | |
| 7,402,410 B2 | 7/2008 | Ponath et al. | |
| 7,435,802 B2 | 10/2008 | Bendig et al. | |
| 7,528,236 B2 | 5/2009 | Fong et al. | |
| 7,682,613 B2 | 3/2010 | Fabene et al. | |
| 7,687,605 B2 | 3/2010 | Fong et al. | |
| 7,803,904 B2 | 9/2010 | Briskin et al. | |
| 8,124,082 B2 | 2/2012 | Fong et al. | |
| 8,246,958 B2 | 8/2012 | Bendig et al. | |
| 8,444,981 B2 | 5/2013 | Hsu et al. | |
| 8,449,489 B2 | 5/2013 | Thorn et al. | |
| 8,454,961 B2 | 6/2013 | Hsu et al. | |
| 8,454,962 B2 | 6/2013 | Hsu et al. | |
| 8,722,019 B2 | 5/2014 | Jefferies et al. | |
| 8,871,490 B2 | 10/2014 | Hsu et al. | |
| 8,962,804 B2 | 2/2015 | Williams et al. | |
| 9,028,815 B2 | 5/2015 | Stavenhagen et al. | |
| 9,040,295 B2 | 5/2015 | Kon et al. | |
| 9,193,790 B2 | 11/2015 | Arthos et al. | |
| 9,364,567 B2 | 6/2016 | Vitalis et al. | |
| 9,441,041 B2 | 9/2016 | Arthos et al. | |
| 9,499,620 B2 | 11/2016 | Hsu et al. | |
| 9,662,490 B2 | 5/2017 | Tracey et al. | |
| 9,663,579 B2 | 5/2017 | Fox et al. | |
| 9,678,071 B2 | 6/2017 | Escalante et al. | |
| 9,717,453 B2 | 8/2017 | Cadavid et al. | |
| 9,764,033 B2 | 9/2017 | Diluzio et al. | |
| 9,821,049 B2 | 11/2017 | Richardson et al. | |
| 9,873,742 B2 | 1/2018 | Keir et al. | |
| 9,896,509 B2 | 2/2018 | Arthos et al. | |
| 9,914,779 B2 | 3/2018 | Borie et al. | |
| 9,976,166 B2 | 5/2018 | Schellenberger et al. | |
| 10,004,808 B2 | 6/2018 | Fox et al. | |
| 10,040,855 B2 | 8/2018 | Diluzio et al. | |
| 10,143,752 B2 | 12/2018 | Fox et al. | |
| 10,221,251 B2 | 3/2019 | Humphreys et al. | |
| 10,273,542 B2 | 4/2019 | Hackney et al. | |
| 10,324,088 B2 | 6/2019 | Singh et al. | |
| 10,519,228 B2 | 12/2019 | Srinivasan et al. | |

(Continued)

FOREIGN PATENT DOCUMENTS

| | | |
|---|---|---|
| BR | 102020016890 A2 | 5/2022 |
| EP | 1173201 B1 | 6/2005 |

(Continued)

OTHER PUBLICATIONS

Aliprantis et al., "A Phase 1 Randomized, Double-Blind, Placebo-Controlled Trial to Assess the Safety, Tolerability, and Pharmacokinetics of a Respiratory Syncytial Virus Neutralizing Monoclonal Antibody MK-1654 in Healthy Adults", Clinical Pharm in Drug Development, vol. 10, No. 5, pp. 556-566, 2021.

Arijs et al., "Effect of Vedolizumab (anti-α4β7-integrin) Therapy on Histological Healing and Mucosal Gene Expression in Patients with UC", Gut Published Online First: Oct. 7, 2016 doi: 10.1136/gutjnl-2016-312293.

Ayalew et al., "C-Terminal Lysine Processing of IgG in Human Suction Blister Fluid: Implications for Subcutaneous Administration", Molecular Pharmaceutics, vol. 19, pp. 4043-4054, 2022.

Boden et al., "Identification of Candidate Biomarkers Associated with Response to Vedolizumab in Inflammatory Bowel Disease", Digestive Diseases and Sciences, vol. 63, pp. 2419-2429, 2018.

(Continued)

*Primary Examiner* — Brad Duffy
(74) *Attorney, Agent, or Firm* — Greenberg Traurig, LLP; Prashant Girinath; Natalie Salem

(57) ABSTRACT

Provided herein are variant α4β7 integrin antibodies and methods of use.

18 Claims, 17 Drawing Sheets

Specification includes a Sequence Listing.

(56) References Cited

U.S. PATENT DOCUMENTS

| | | |
|---|---|---|
| 10,532,051 B2 | 1/2020 | Ebsworth et al. |
| 10,654,931 B2 | 5/2020 | Hosen et al. |
| 10,669,587 B2 | 6/2020 | Hackney et al. |
| 10,844,416 B2 | 11/2020 | Tescione et al. |
| 10,918,716 B2 | 2/2021 | Lissoos et al. |
| 10,947,254 B2 | 3/2021 | Hudson et al. |
| 10,981,965 B2 | 4/2021 | Mumm |
| 10,981,966 B2 | 4/2021 | Mumm |
| 10,988,540 B2 | 4/2021 | Hosen et al. |
| 11,045,469 B2 | 6/2021 | Campbell et al. |
| 11,053,303 B2 | 7/2021 | Lebert et al. |
| 11,059,911 B2 | 7/2021 | Humphreys et al. |
| 11,091,551 B2 | 8/2021 | Keir et al. |
| 11,261,493 B2 | 3/2022 | Hackney et al. |
| 11,268,119 B2 | 3/2022 | Mitchelson et al. |
| 11,286,308 B2 | 3/2022 | Waldman et al. |
| 11,377,499 B2 | 7/2022 | Wu |
| 11,389,533 B2 | 7/2022 | Rosario et al. |
| 11,560,434 B2 | 1/2023 | Diluzio et al. |
| 11,596,688 B2 | 3/2023 | Rosario et al. |
| 11,639,390 B2 | 5/2023 | Min et al. |
| 11,753,668 B2 | 9/2023 | Mitchelson et al. |
| 11,760,803 B2 | 9/2023 | Brake et al. |
| 11,780,852 B2 | 10/2023 | Hudson et al. |
| 11,806,507 B2 | 11/2023 | Herzlinger |
| 2001/0046496 A1 | 11/2001 | Brettman et al. |
| 2002/0197233 A1 | 12/2002 | Relton et al. |
| 2004/0132642 A1 | 7/2004 | Hwang |
| 2005/0053598 A1 | 3/2005 | Burke et al. |
| 2005/0074451 A1 | 4/2005 | Yednock et al. |
| 2005/0095238 A1 | 5/2005 | Brettman et al. |
| 2005/0233387 A1 | 10/2005 | Artis et al. |
| 2005/0255118 A1 | 11/2005 | Wehner |
| 2005/0260193 A1 | 11/2005 | Lieberburg |
| 2005/0276803 A1 | 12/2005 | Chan et al. |
| 2006/0029600 A1 | 2/2006 | Rubin et al. |
| 2006/0128607 A1 | 6/2006 | Bosserhoff et al. |
| 2006/0234306 A1 | 10/2006 | Artis et al. |
| 2007/0048219 A1 | 3/2007 | Hsei et al. |
| 2007/0122403 A1 | 5/2007 | Dall'Acqua et al. |
| 2007/0122404 A1 | 5/2007 | O'Keefe |
| 2008/0075719 A1 | 3/2008 | Chan et al. |
| 2008/0153756 A1 | 6/2008 | Krissansen et al. |
| 2009/0011464 A1 | 1/2009 | Ponath et al. |
| 2009/0208492 A1 | 8/2009 | O'Connor et al. |
| 2009/0214527 A1 | 8/2009 | Burgess et al. |
| 2009/0263421 A1 | 10/2009 | Spetz-Holmgren et al. |
| 2009/0298195 A1 | 12/2009 | Ruker et al. |
| 2010/0119517 A1 | 5/2010 | Burgess et al. |
| 2010/0129353 A1 | 5/2010 | DeLuca |
| 2010/0247431 A1 | 9/2010 | Armour et al. |
| 2010/0255508 A1 | 10/2010 | Gelzleichter et al. |
| 2010/0266587 A1 | 10/2010 | McLachlan |
| 2010/0266636 A1 | 10/2010 | Richardson et al. |
| 2010/0267934 A1 | 10/2010 | VandeWinkel et al. |
| 2010/0297699 A1 | 11/2010 | Li et al. |
| 2011/0002851 A1 | 1/2011 | Haas et al. |
| 2011/0158982 A1 | 6/2011 | Segal et al. |
| 2012/0034243 A1 | 2/2012 | Brettman et al. |
| 2012/0039907 A1 | 2/2012 | Armour et al. |
| 2012/0121580 A1 | 5/2012 | Bhambhani et al. |
| 2012/0282249 A1 | 11/2012 | Fox et al. |
| 2013/0052642 A1 | 2/2013 | Alvarez et al. |
| 2013/0059337 A1 | 3/2013 | Bendig et al. |
| 2013/0108617 A1 | 5/2013 | Kappos et al. |
| 2013/0109032 A1 | 5/2013 | Gelzleichter et al. |
| 2013/0337470 A1 | 12/2013 | Chackerian |
| 2014/0004130 A1 | 1/2014 | Bordignon |
| 2014/0080762 A1 | 3/2014 | Hazlehurst et al. |
| 2014/0120084 A1 | 5/2014 | Anand et al. |
| 2014/0135483 A1 | 5/2014 | Seito et al. |
| 2014/0154252 A1 | 6/2014 | Thompson et al. |
| 2014/0170157 A1 | 6/2014 | Agarwal et al. |
| 2014/0186345 A1 | 7/2014 | Brettman et al. |
| 2014/0212425 A1 | 7/2014 | Chang et al. |
| 2014/0377253 A1 | 12/2014 | Harding et al. |
| 2015/0010563 A1 | 1/2015 | Hamrah et al. |
| 2015/0056205 A1 | 2/2015 | Lieberburg |
| 2015/0064177 A1 | 3/2015 | Bendig et al. |
| 2015/0093399 A1 | 4/2015 | Jefferies |
| 2015/0197560 A1 | 7/2015 | Fong et al. |
| 2015/0238602 A1 | 8/2015 | Cadavid et al. |
| 2016/0129112 A1 | 5/2016 | Neelon |
| 2016/0209426 A1 | 7/2016 | Diehl et al. |
| 2016/0340435 A1 | 11/2016 | Chang et al. |
| 2016/0340443 A1 | 11/2016 | Rossi et al. |
| 2016/0375133 A1 | 12/2016 | Bhambhani et al. |
| 2017/0002077 A1 | 1/2017 | Tam et al. |
| 2017/0020867 A1 | 1/2017 | Moussy et al. |
| 2017/0102393 A1 | 4/2017 | Gelzleichter et al. |
| 2017/0210807 A1 | 7/2017 | Fong et al. |
| 2017/0258869 A1 | 9/2017 | Li |
| 2017/0275365 A1 | 9/2017 | Hsu et al. |
| 2017/0315133 A1 | 11/2017 | Alexander et al. |
| 2017/0327584 A1 | 11/2017 | Lasch |
| 2017/0360926 A1 | 12/2017 | Rosario et al. |
| 2018/0051086 A1 | 2/2018 | Abhyanker |
| 2018/0086833 A1 | 3/2018 | Hassanali et al. |
| 2018/0142017 A1 | 5/2018 | Hamrah et al. |
| 2018/0148514 A1 | 5/2018 | Williams |
| 2018/0207279 A1 | 7/2018 | Fox et al. |
| 2018/0289811 A1 | 10/2018 | Fox et al. |
| 2018/0291104 A1 | 10/2018 | Fong et al. |
| 2018/0327497 A1 | 11/2018 | Diluzio et al. |
| 2018/0346578 A1 | 12/2018 | Diluzio et al. |
| 2019/0010242 A1 | 1/2019 | Eckelman et al. |
| 2019/0038744 A1 | 2/2019 | Cadavid et al. |
| 2019/0040140 A1 | 2/2019 | Brake et al. |
| 2019/0076532 A1 | 3/2019 | Diluzio et al. |
| 2019/0077868 A1 | 3/2019 | Sachs et al. |
| 2019/0192683 A1 | 6/2019 | Jefferies |
| 2019/0231878 A1 | 8/2019 | Brown et al. |
| 2019/0310266 A1 | 10/2019 | Gelzleichter et al. |
| 2019/0330318 A1 | 10/2019 | Bennett et al. |
| 2019/0330366 A1 | 10/2019 | Eckelman et al. |
| 2019/0345240 A1 | 11/2019 | Srinivasan et al. |
| 2020/0002422 A1 | 1/2020 | Sachs et al. |
| 2020/0002423 A1 | 1/2020 | Brettman et al. |
| 2020/0018751 A1 | 1/2020 | Singh et al. |
| 2020/0025775 A1 | 1/2020 | Diehl et al. |
| 2020/0031937 A1 | 1/2020 | Lasch |
| 2020/0048354 A1 | 2/2020 | Fong et al. |
| 2020/0087401 A1 | 3/2020 | Rosario et al. |
| 2020/0148773 A1 | 5/2020 | Taylor et al. |
| 2020/0155673 A1 | 5/2020 | Rosario et al. |
| 2020/0165677 A1 | 5/2020 | Stappenbeck et al. |
| 2020/0179486 A1 | 6/2020 | Rosario et al. |
| 2020/0206353 A1 | 7/2020 | Fox et al. |
| 2020/0241006 A1 | 7/2020 | Naik et al. |
| 2020/0253506 A1 | 8/2020 | Jones et al. |
| 2020/0265940 A1 | 8/2020 | Dulai |
| 2020/0276303 A1 | 9/2020 | Cadavid et al. |
| 2020/0283533 A1 | 9/2020 | Hosen et al. |
| 2020/0323772 A1 | 10/2020 | Jones et al. |
| 2020/0376092 A1 | 12/2020 | Vitalis et al. |
| 2020/0392231 A1 | 12/2020 | Anania et al. |
| 2020/0392232 A1 | 12/2020 | Hassanali et al. |
| 2021/0024636 A1 | 1/2021 | Mansour-Awad |
| 2021/0052733 A1 | 2/2021 | Diluzio et al. |
| 2021/0147555 A1 | 5/2021 | Jayaraman et al. |
| 2021/0238288 A1 | 8/2021 | Anand et al. |
| 2021/0252141 A1 | 8/2021 | Lissoos et al. |
| 2021/0253714 A1 | 8/2021 | Jayaraman et al. |
| 2021/0260185 A1 | 8/2021 | Cadavid et al. |
| 2021/0262032 A1 | 8/2021 | Chowers et al. |
| 2021/0278416 A1 | 9/2021 | Ananthakrishnan et al. |
| 2021/0290604 A1 | 9/2021 | Williams |
| 2021/0301002 A1 | 9/2021 | Bennett et al. |
| 2021/0322410 A1 | 10/2021 | Campbell et al. |
| 2021/0338836 A1 | 11/2021 | Yu et al. |
| 2021/0340261 A1 | 11/2021 | Diluzio et al. |
| 2021/0340584 A1 | 11/2021 | Tescione et al. |
| 2021/0388092 A1 | 12/2021 | Abhyankar |
| 2021/0396753 A1 | 12/2021 | Rubin et al. |

(56) References Cited

U.S. PATENT DOCUMENTS

| | | |
|---|---|---|
| 2021/0401982 A1 | 12/2021 | Jayaraman et al. |
| 2022/0010019 A1 | 1/2022 | Swirski et al. |
| 2022/0041735 A1 | 2/2022 | Hosen et al. |
| 2022/0048992 A1 | 2/2022 | Gabathuler et al. |
| 2022/0062372 A1 | 3/2022 | Srinivasan et al. |
| 2022/0098329 A1 | 3/2022 | Santich et al. |
| 2022/0162297 A1 | 5/2022 | Basi |
| 2022/0170028 A1 | 6/2022 | Li et al. |
| 2022/0186314 A1 | 6/2022 | Hackney et al. |
| 2022/0193235 A1 | 6/2022 | Herzlinger |
| 2022/0206012 A1 | 6/2022 | Chackerian |
| 2022/0220556 A1 | 7/2022 | Khatri et al. |
| 2022/0259291 A1 | 8/2022 | Oppenheim et al. |
| 2022/0267448 A1 | 8/2022 | Gowtham et al. |
| 2022/0267449 A1 | 8/2022 | Ameli et al. |
| 2022/0289855 A1 | 9/2022 | Ginsberg et al. |
| 2022/0290241 A1 | 9/2022 | McGovern et al. |
| 2022/0298232 A1 | 9/2022 | Srinivasan et al. |
| 2022/0306735 A1 | 9/2022 | Dekosky et al. |
| 2022/0349903 A1 | 11/2022 | Gelzleichter et al. |
| 2022/0357343 A1 | 11/2022 | Diehl et al. |
| 2022/0370617 A1 | 11/2022 | Diluzio et al. |
| 2022/0378739 A1 | 12/2022 | Rezvani et al. |
| 2022/0403033 A1 | 12/2022 | Anand et al. |
| 2022/0403034 A1 | 12/2022 | Hassanali et al. |
| 2023/0033021 A1 | 2/2023 | Jones et al. |
| 2023/0043949 A1 | 2/2023 | Rosario et al. |
| 2023/0048046 A1 | 2/2023 | Li et al. |
| 2023/0093155 A1 | 3/2023 | Li et al. |
| 2023/0096620 A1 | 3/2023 | Mora et al. |
| 2023/0142437 A1 | 5/2023 | Ling et al. |
| 2023/0287075 A1 | 9/2023 | Mumm |
| 2023/0295336 A1 | 9/2023 | Eckelman et al. |
| 2023/0310712 A1 | 10/2023 | Ling et al. |
| 2023/0312727 A1 | 10/2023 | Diluzio et al. |
| 2023/0313305 A1 | 10/2023 | Stappenbeck et al. |
| 2023/0340131 A1 | 10/2023 | Jayaraman et al. |
| 2024/0101679 A1 | 3/2024 | Jayaraman et al. |

FOREIGN PATENT DOCUMENTS

| | | |
|---|---|---|
| EP | 1133315 B1 | 2/2006 |
| EP | 1214091 B1 | 10/2006 |
| EP | 0808367 B1 | 7/2007 |
| EP | 1113810 B1 | 12/2008 |
| EP | 1078006 B1 | 3/2009 |
| EP | 1699826 B1 | 3/2009 |
| EP | 1835922 B1 | 5/2009 |
| EP | 1123086 B1 | 3/2010 |
| EP | 1485127 B1 | 6/2011 |
| EP | 1784426 B1 | 11/2011 |
| EP | 2458990 B1 | 6/2012 |
| EP | 1278543 B1 | 9/2012 |
| EP | 1896504 B1 | 11/2012 |
| EP | 2140881 B1 | 4/2013 |
| EP | 2279004 B1 | 1/2015 |
| EP | 0918797 B2 | 9/2015 |
| EP | 2021025 B1 | 8/2016 |
| EP | 2298348 B1 | 10/2016 |
| EP | 2109480 B1 | 6/2017 |
| EP | 2704742 A1 | 7/2017 |
| EP | 2704798 B1 | 7/2017 |
| EP | 2739649 B1 | 9/2017 |
| EP | 2632492 B1 | 10/2017 |
| EP | 2854845 B1 | 3/2018 |
| EP | 3224619 B1 | 1/2019 |
| EP | 3131559 B1 | 2/2019 |
| EP | 2903691 B1 | 5/2019 |
| EP | 3268742 B1 | 5/2019 |
| EP | 2408816 B1 | 9/2019 |
| EP | 2782599 B1 | 10/2019 |
| EP | 3254697 B1 | 11/2019 |
| EP | 3321281 B1 | 11/2019 |
| EP | 3326645 B1 | 3/2020 |
| EP | 3167902 B1 | 7/2020 |
| EP | 2970372 B1 | 9/2020 |
| EP | 1587540 B1 | 9/2021 |
| EP | 3530673 B1 | 3/2022 |
| EP | 3411120 B1 | 5/2023 |
| EP | 3554539 B9 | 6/2023 |
| EP | 3615001 B1 | 7/2023 |
| WO | WO 1990007321 A2 | 7/1990 |
| WO | WO 2000030681 A1 | 6/2000 |
| WO | WO 2001080833 A1 | 11/2001 |
| WO | WO 2002077610 A2 | 10/2002 |
| WO | WO 2005046731 A1 | 5/2005 |
| WO | WO 2007007151 A2 | 1/2007 |
| WO | WO 2007007152 A2 | 1/2007 |
| WO | WO 2007007159 A2 | 1/2007 |
| WO | WO 2007007160 A2 | 1/2007 |
| WO | 2007061679 A1 | 5/2007 |
| WO | WO 2013142857 | 9/2013 |
| WO | WO 2014049044 A1 | 4/2014 |
| WO | WO 2014182532 A1 | 11/2014 |
| WO | WO 2014193625 A1 | 12/2014 |
| WO | WO 2015174978 A1 | 11/2015 |
| WO | WO 2017019673 A2 | 2/2017 |
| WO | WO 2017087735 A1 | 5/2017 |
| WO | WO 2017158393 A1 | 9/2017 |
| WO | WO 2017165742 A1 | 9/2017 |
| WO | 2017218434 A1 | 12/2017 |
| WO | WO 2018104893 | 6/2018 |
| WO | WO 2019180163 | 9/2019 |
| WO | WO 2019196522 A1 | 10/2019 |
| WO | WO 2020260315 A1 | 12/2020 |
| WO | WO 2021003553 A1 | 1/2021 |
| WO | WO 2021060425 A1 | 4/2021 |
| WO | WO 2021070203 A1 | 4/2021 |
| WO | WO 2021188814 A1 | 9/2021 |
| WO | WO 2021188827 A1 | 9/2021 |
| WO | WO 2022026699 A1 | 2/2022 |
| WO | WO 2022036422 A1 | 2/2022 |
| WO | WO 2022123603 A1 | 6/2022 |
| WO | WO 2022157806 A1 | 7/2022 |
| WO | WO 2022192225 A1 | 9/2022 |
| WO | WO 2022234594 A1 | 11/2022 |
| WO | WO 2022253994 A1 | 12/2022 |
| WO | WO 2022272033 A2 | 12/2022 |
| WO | WO 2023288203 A1 | 1/2023 |
| WO | WO 2023007516 A1 | 2/2023 |
| WO | WO 2023012828 A1 | 2/2023 |
| WO | WO 2023021532 A1 | 2/2023 |
| WO | WO 2023044402 A1 | 3/2023 |
| WO | WO 2023058051 A1 | 4/2023 |
| WO | WO 2023064278 A2 | 4/2023 |
| WO | WO 2023064945 A2 | 4/2023 |
| WO | WO 2023073469 A1 | 5/2023 |
| WO | WO 2023081809 A1 | 5/2023 |
| WO | WO 2023086910 A1 | 5/2023 |
| WO | WO 2023097219 A2 | 6/2023 |
| WO | WO 2023116099 A1 | 6/2023 |
| WO | WO 2023126411 A1 | 7/2023 |
| WO | WO 2023166179 A1 | 9/2023 |
| WO | WO 2023194837 A1 | 10/2023 |
| WO | WO 2023196866 A1 | 10/2023 |
| WO | WO 2023215882 A1 | 11/2023 |
| WO | WO 2023217072 A1 | 11/2023 |
| WO | 2025038708 A1 | 2/2025 |

OTHER PUBLICATIONS

Boden et al., "Vedolizumab Efficacy Is Associated With Decreased Intracolonic Dendritic Cells, Not Memory T Cells", Inflammatory Bowel Diseases, vol. 30, Issue 5, pp. 704-717, May 2024.

Bokemeyer et al., "Real-World Effectiveness of Vedolizumab vs Anti-TNF in Biologic-naïve Crohn's Disease Patients: A 2-year Propensity-score-adjusted Analysis from the VEDO $_{IBD}$-Study", Inflammatory Bowel Diseases, vol. 30, No. 5, pp. 746-756, May 2024.

Bressler et al., "Vedolizumab and Anti-Tumour Necrosis Factor α Real-World Outcomes in Biologic-Naïve Inflammatory Bowel Disease Patients: Results from the EVOLVE Study", Journal of Crohn's and Colitis, vol. 15, No. 10, pp. 1694-1706, Oct. 2021.

(56) References Cited

OTHER PUBLICATIONS

Buer et al., "Combining Anti-TNF-α and Vedolizumab in the Treatment of Inflammatory Bowel Disease: A Case Series", Inflamm Bowel Dis., vol. 24, No. 5, pp. 997-1004, May 2018.

Casanova et al., "Persistence, Effectiveness and Safety of Ustekinumab and Vedolizumab Therapy for Complex Perianal Fistula in Crohn's Disease: The HEAL Study from GETECCU", Digestive and Liver Disease, DOI: 10.1016/j.dld.2024.05.009, Jun. 2024.

Colombel et al., "Vedolizumab, Adalimumab, and Methotrexate Combination Therapy in Crohn's Disease (Explorer)", Clinical Gastroenterology and Hepatology, vol. 22, No. 7, pp. 1487-1496, Jul. 2024.

D'Haens et al., Exposure-Efficacy Relationship of Vedolizumab Subcutaneous and Intravenous Formulations in Crohn's Disease and Ulcerative Colitis, Expert Review of Clinical Pharmacology, vol. 17, No. 4, pp. 403-412, Apr. 2024.

Dosing, "A Randomized Trial of Vedolizumab Dose Optimization in Patients With Moderate to Severe Ulcerative Colitis Who Have Early Nonresponse and High Drug Clearance: The ENTERPRET Trial", Gastroenterol. Hepatol., vol. 18, pp. 7-8, Jul. 2022.

Dreesen et al., "Evidence to Support Monitoring of Vedolizumab Trough Concentrations in Patients With Inflammatory Bowel Diseases", Clinical Gastroenterology and Hepatology, vol. 16, No. 12, pp. 1937-1946, 2018.

Engel et al., "Vedolizumab in IBD-Lessons From Real-World Experience; A Systematic Review and Pooled Analysis", Journal of Crohn's and Colitis, vol. 12, No. 2, pp. 245-257, Jan. 24, 2018.

Feagan et al., "Vedolizumab as Induction and Maintenance Therapy for Ulcerative Colitis", The New England Journal of Medicine, vol. 369, No. 8, pp. 699-710, Aug. 22, 2013.

Gabriels et al., "Using Fluorescently Labeled Vedolizumab to Visualize Local Drug Distribution During Colonoscopy and Identify Mucosal Target Cells in Patients with Inflammatory Bowel Disease".

Gonzalez et al. "Crohn's Patient Serum Proteomics Reveals Response Signature for Infliximab but not Vedolizumab". Inflamm Bowel Dis. Feb. 17, 2024:izae016. doi: 10.1093/ibd/izae016. Epub ahead of print. PMID: 38367209.

Hanzel et al., "Pharmacokinetic-Pharmacodynamic Model of Vedolizumab for Targeting Endoscopic Remission in Patients With Crohn Disease: Posthoc Analysis of the LOVE-CD Study", Inflammatory Bowel Diseases, vol. 28, pp. 689-699, 2022.

Haraya et al., "Translational Approach for Predicting HumanPharmacokinetics of Engineered Therapeutic Monoclonal Antibodies with Increased FcRn-Binding Mutations", BioDrugs, vol. 37, pp. 99-108, 2023.

Honap et al., "An Update on the Safety of Long-Term Vedolizumab Use in Inflammatory Bowel Disease", Expert Opinion on Drug Safety, vol. 22, No. 9, pp. 767-776, 2023.

Hu et al., "Evaluation of Heavy Chain C-Terminal Deletions on Productivity and Product Quality of Monoclonal Antibodies in Chinese Hamster Ovary (CHO) Cells", Biotech Progress, vol. 33, No. 3, pp. 786-794, Mar. 24, 2017.

Hu et al., "Combination "Therapy "Does Not Improve Rate of Clinical or Endoscopic Remission in Patients with Inflammatory Bowel Diseases Treated with Vedolizumb or Ustekinumab", Clinical Gastroenterology and Hepatology, vol. 19, pp. 1366-1376, 2021.

Hui et al., "Vedolizumab for Induction and Maintenance of Remission in Crohn's Disease", Cochrane Database of Systematic Reviews, Issue 7, Art. No.: CD013611, DOI: 10.1002/14651858.CD013611.pub2, pp. 1-66, 2023.

Jiang et al., "Evaluation of Heavy-Chain C-Terminal Deletion on Product Quality and Pharmacokinetics of Monoclonal Antibodies", Journal of Pharmaceutical Sciences, vol. 105, No. 7, pp. 2066-2072, Jul. 1, 2016.

Liu et al., "Ustekinumab and Vedolizumab Dual Biologic Therapy in the Treatment of Crohn's Disease", Case Reports in Medicine, vol. 2017, Article ID 5264216, 2 pages, Nov. 2017.

Loftus et al., "Long-Term Safety of Vedolizumab for Inflammatory Bowel Disease", Alimentary Pharmacology & Therapeutics, vol. 52, pp. 1353-1365, 2020.

Mao et al., "Safety of Dual Biological Therapy in Crohn's Disease: A Case Series of Vedolizumab in Combination with Other Biologics", BMJ Open Gastro, vol. 5, No. 1, e000243. doi: 10.1136/bmjgast-2018-000243.

Nowak et al., "A Phase 1 Randomized Dose-Escalation Study of a Human Monoclonal Antibody to IL-6 in CKD", Kidney360, vol. 2, pp. 224-235, Feb. 2021.

Orito et al., "A Phase I Study to Evaluate Safety, Pharmacokinetics, and Pharmacodynamics of Respiratory Syncytial Virus Neutralizing Monoclonal Antibody MK-1654 in Healthy Japanese Adults" Clinical and Translational Science, vol. 15, No. 7, pp. 1753-1763, Jul. 2022.

Osterman et al., "Vedolizumab Exposure Levels and Clinical Outcomes in Ulcerative Colitis: Determining the Potential for Dose Optimisation", Aliment Pharmacol Ther., vol. 49, pp. 408-418, 2019.

Parikh et al., "Vedolizumab for the Treatment of Active Ulcerative Colitis: A Randomized Controlled Phase 2 Dose-Ranging Study", Inflamm Bowel Dis., vol. 18, No. 8, pp. 1470-1479, Aug. 2012.

Parrot et al., "Systematic Review with Meta-Analysis: the Effectiveness of Either Ustekinumab or Vedolizumab in Patients with Crohn's Disease Refractory to Anti-Tumour Necrosis Factor", Aliment Pharmacol Therap., vol. 55, pp. 380-388, 2022.

Peyrin-Biroulet et al., "Loss of Response to Vedolizumab and Ability of Dose Intensification to Restore Response in Patients with Crohn's Disease or Ulcerative Colitis: A Systematic Review and Meta-Analysis", Clinical Gastroenterology and Hepatology, vol. 17, No. 5, pp. 838-846, Apr. 2019.

Poole et al., "Vedolizumab: First Global Approval", Drugs, vol. 74, pp. 1293-1303, 2014.

Ramdani et al., "Monoclonal Antibody Engineering and Design to Modulate FcRn Activities: A Comprehensive Review", International Journal of Molecular Sciences, vol. 23, No., 17, pp. 9604 (1-12), Aug. 2022.

Ribaldone et al., Dual biological therapy with Anti-TNF, Vedolizumab or Ustekinumab in Inflammatory Bowel Disease: A Systematic Review with Pool Analysis, Scandinavian Journal of Gastroenterology, vol. 54, No. 4, ppl 407-413, 2019.

Rosario et al., "Vedolizumab Pharmacokinetics, Pharmacodynamics, Safety, and Tolerability Following Administration of a Single, Ascending, Intravenous Dose to Healthy Volunteers", Clin. Drug Investig., vol. 36, pp. 913-923, 2016.

Sandborn et al., "Vedolizumab as Induction and Maintenance Therapy for Crohn's Disease", The New England Journal of Medicine, vol. 369, No. 8, pp. 711-721, Aug. 22, 2013.

Sands et al., "Effects of Vedolizumab Induction Therapy for Patients With Crohn's Disease in Whom Tumor Necrosis Factor Antagonist Treatment Failed", Gastroenterology, vol. 147, pp. 618-627, 2014.

Sands et al., "Vedolizumab versus Adalimumab for Moderate-to-Severe Ulcerative Colitis", N.E. Journal of Medicine, vol. 381, No. 13, pp. 1215-1226, 2019.

Schmidt et al., "Predictors and Management of Loss of Response to Vedolizumab in Inflammatory Bowel Disease", Inflamm Bowel Dis., vol. 24, No. 11, pp. 2461-2467, Nov. 2018.

Sengupta et al., Higher Vedolizumab Serum Levels do not Increase the Risk of Adverse Events in Patients with Inflammatory Bowel Disease, Scand. Journal of Gastroenterology, vol. 55, No. 7, pp. 800-805, 2020.

Singh et al., "A Phase 1 Study of the Long-Acting Anti-IL-5 Monoclonal Antibody GSK3511294 in Patients with Asthma", Br. J. Clin. Pharmacol., vol. 88, pp. 702-712, 2022.

Ungar et al., "Association of Vedolizumab Level, Anti-Drug Antibodies, and a4b7 Occupancy With Response in Patients With Inflammatory Bowel Diseases", Clinical Gastroenterology and Hepatology, vol. 16, pp. 697-705, 2018.

Ungar et al., "Dose Optimisation for Loss of Response to Vedolizumab - Pharmacokinetics and Immune Mechanisms", Journal of Crohn's and Colitis, vol. 15, No. 10, pp. 1707-1719, Oct. 2021.

(56) References Cited

OTHER PUBLICATIONS

Vande Casteele et al., Real-world multicentre observational study including population pharmacokinetic modelling to evaluate the exposure-response relationship of vedolizumab in inflammatory bowel disease: ERELATE Study, Alimentary Pharm & Therapeutics, vol. 56, No. 3, pp. 463-476, Aug. 2022.

Veisman et al., Association of Infliximab and Vedolizumab Trough Levels with Reported Rates of Adverse Events: A Cross-Sectional Study, Journal of Clinical Medicine, vol. 10, No. 18, pp. 4265, Sep. 2021.

Vermeire et al., "Efficacy and Safety of Subcutaneous Vedolizumab in Patients With Moderately to Severely Active Crohn's Disease: Results From the VISIBLE 2 Randomised Trial", Journal of Crohn's and Colitis, vol. 16, No. 1, pp. 27-38, Jan. 2022.

Verstockt et al., "Expression Levels of 4 Genes in Colon Tissue Might Be Used to Predict Which Patients Will Enter Endoscopic Remission After Vedolizumab Therapy for Inflammatory Bowel Diseases", Clinical Gastroenterology and Hepatology, vol. 18, pp. 1142-1151, 2020.

Wyant et al., "Development and Validation of Receptor Occupancy Pharmacodynamic Assays Used in the Clinical Development of the Monoclonal Antibody Vedolizumab", Cytometry Part B (Clinical Cytometry), vol. 90B, pp. 168-176, 2016.

Wyant et al., "Vedolizumab Affects Antibody Responses to Immunization Selectively in the Gastrointestinal Tract: Randomised Controlled Trial Results", Gut, vol. 64, No. 1, pp. 77-83, 2015.

Xu et al., "PCSK9 Inhibitor Recaticimab for Hypercholesterolemia on Stable Statin Dose: a Randomized, Double-Blind, Placebo-Controlled Phase 1b/2 Study", BMC Medicine, vol. 20, No. 13, pp. 1-13, 2022.

Yarur et al., "Vedolizumab Concentrations Are Associated with Long-Term Endoscopic Remission in Patients with Inflammatory Bowel Diseases", Digestive Diseases and Sciences, vol. 64, pp. 1651-1659, 2019.

Zeissig et al., "Vedolizumab is Associated with Changes in Innate Rather than Adaptive Immunity in Patients with Inflammatory Bowel Disease", Gut, vol. 68, No. 1, pp. 25-39, Jan. 2019.

Zhu et al., "A Novel Monoclonal Antibody Drug Candidate SPY001 Targeting Integrin $\alpha 4\beta 7$ for the Treatment of IBD Demonstrates Prolonged Half-Life in Non-Human Primates", Abstract citation ID: jjad212.0895 P765.

Zhu et al., "Development and Characterization of a Novel Extended Half-Life Monoclonal Antibody Drug Candidate Targeting Integrin $\alpha 4\beta 7$ for the Treatment of IBD", Abstract citation ID: jjad212.0717 P587.

International Search Report and Written Opinion in PCT International Application No. PCT/US2024/031569 mailed Sep. 23, 2024. (14 pages).

U.S. Appl. No. 18/774,099, filed Jul. 16, 2024, Injectable Formulations for Treatment of the Inflammatory Bowel Disease.

U.S. Appl. No. 18/774,143, filed Jul. 16, 2024, Method of Treating Inflammatory Bowel Disease.

Laursen et al., "Pain Perception After Subcutaneous Injections of Media Containing Different Buffers", Basic and Clinical Pharmacology and Toxicology, vol. 98, pp. 218-221 (Year: 2006).

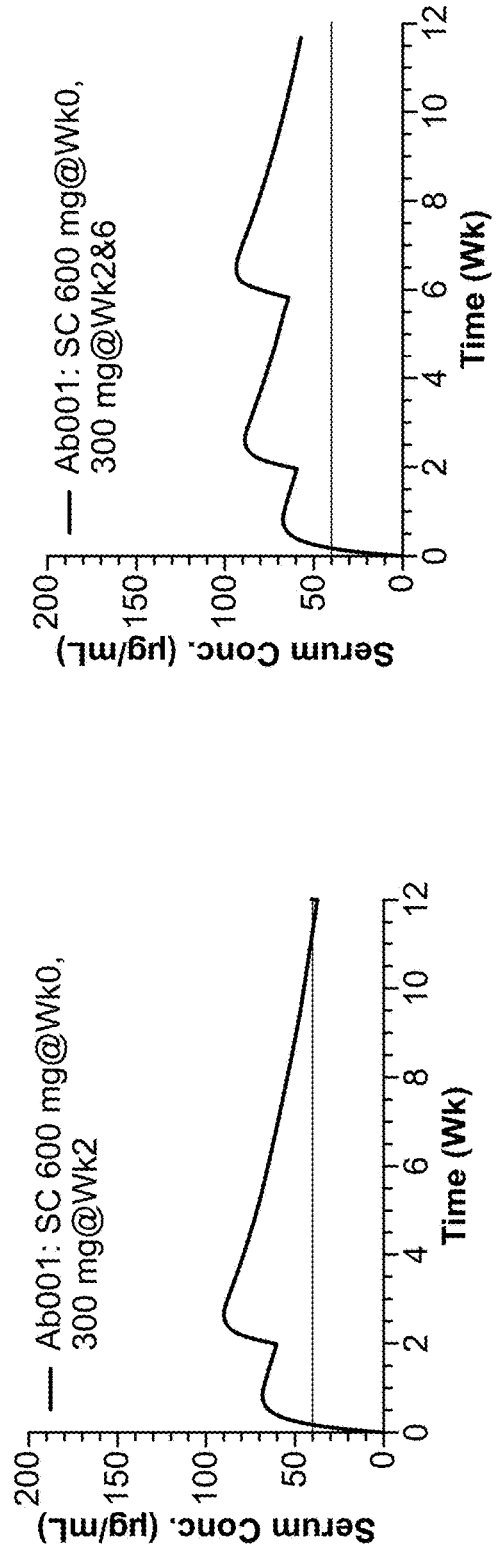
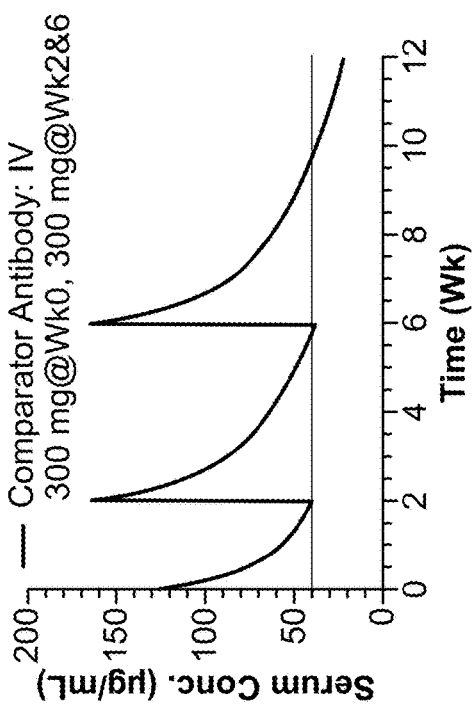
FIG. 10A
FIG. 10B
FIG. 10C

DOSING REGIMEN FOR TREATING INFLAMMATORY BOWEL DISEASE

CROSS-REFERENCE TO RELATED APPLICATIONS

This application is a continuation of International Application No. PCT/US2024/031569, filed May 30, 2024, which claims the benefit of and priority to U.S. Provisional Application No. 63/504,966, filed on May 30, 2023; U.S. Provisional Application No. 63/505,962, filed on Jun. 2, 2023; U.S. Provisional Application No. 63/599,922, filed on Nov. 16, 2023; U.S. Provisional Application No. 63/554,886, filed on Feb. 16, 2024; and U.S. Provisional Application No. 63/559,081, filed on Feb. 28, 2024, the entire contents of each of which are incorporated herein by reference.

SEQUENCE LISTING

This application contains a Sequence Listing which has been submitted electronically in XML format and is hereby incorporated by reference in its entirety. The XML copy, created on Jul. 12, 2024, is titled 220703-010209.xml and is 23.8 kilobytes in size.

BACKGROUND

Integrins are cell-adhesion transmembrane receptors that function as extracellular matrix (ECM)-cytoskeletal linkers and transducers of biochemical and mechanical signals between cells and their environment. Due to their exposure on the cell surface and sensitivity to molecular inhibition, integrins such as α4β7 integrins have been investigated as pharmacological targets for treating various diseases including cancer and inflammatory diseases (e.g., inflammatory bowel disease). However, current integrin therapies have been associated with serious side effects given the role of integrins in important biological processes and/or require multiple and frequent doses to maintain therapeutic efficacy. As such, improved α4β7 therapies are needed.

SUMMARY

The disclosure provides, in one aspect, a multidose regimen for use in treating a disease in a subject in need thereof comprising: (a) a first injectable liquid formulation comprising a total dosage amount of at least 500 mg of an α4β7 binding antibody; and (b) a second injectable liquid formulation comprising a total dosage amount of at least 120 mg of the α4β7 binding antibody, wherein the α4β7 binding antibody consists of: (i) a heavy chain consisting of an amino acid sequence according to SEQ ID NO: 1, and (ii) a light chain consisting of an amino acid sequence according to SEQ ID NO: 3.

In certain embodiments, the first injectable liquid formulation comprises a total dosage amount of from about 500 mg to about 1200 mg of the α4β7 binding antibody and the second injectable liquid formulation comprises a total dosage amount of from about 120 mg to about 450 mg of the α4β7 binding antibody.

In some embodiments, the first injectable liquid formulation comprises a total dosage amount of about 600 mg of the α4β7 binding antibody and the second injectable liquid formulation comprises a total dosage amount of about 300 mg of the α4β7 binding antibody.

In some embodiments, the first injectable liquid formulation is for intravenous administration.

In certain embodiments, the first injectable liquid formulation is for subcutaneous administration. In some embodiments, the first injectable liquid formulation is suitable for administration as a single injection or multiple injections.

In certain embodiments, the second injectable liquid formulation is for subcutaneous administration. In some embodiments, the second injectable liquid formulation is suitable for administration as a single injection or multiple injections.

In some embodiments, the disease is an inflammatory bowel disease. In some embodiments, the inflammatory bowel disease is Crohn's disease. In some embodiments, the inflammatory bowel disease is ulcerative colitis.

In one aspect, the disclosure provides a dosing regimen for use in treating a disease in a subject in need thereof, the dosing regimen comprising: (a) a first formulation comprising a total dosage amount of at least about 500 mg of an α4β7 binding antibody for administration to the subject; (b) a second formulation comprising a total dosage amount of at least about 120 mg of the α4β7 binding antibody for subcutaneous administration to the subject after the first formulation, and thereafter as a maintenance dose at least eight weeks after administration of the second formulation, wherein the α4β7 binding antibody consists of: (i) a heavy chain consisting of an amino acid sequence according to SEQ ID NO: 1, and (ii) a light chain consisting of an amino acid sequence according to SEQ ID NO: 3.

In some embodiments, the first formulation is for subcutaneous administration.

In some embodiments, the first formulation is for intravenous administration.

In certain embodiments, the first formulation comprises a total dosage amount of from about 500 mg to about 1200 mg of the α4β7 binding antibody. For example, in some embodiments, the first formulation comprises a total dosage amount of about 600 mg of the α4β7 binding antibody.

In certain embodiments, the second formulation comprises a total dosage amount of from about 120 mg to about 450 mg of the α4β7 binding antibody. For example, in some embodiments, the second formulation comprises a total dosage amount of about 300 mg of the α4β7 binding antibody.

In certain embodiments, the second formulation is administered at least two weeks after the first formulation, and thereafter as a maintenance dose at least eight weeks after administration of the second formulation.

In some embodiments, the first formulation is suitable for administration as a single injection or multiple injections. In some embodiments, the second formulation is suitable for administration as a single injection or multiple injections.

In certain embodiments, the first formulation and the second formulation do not contain citrate.

In certain embodiments, the disease is an inflammatory bowel disease. In some embodiments, the inflammatory bowel disease is Crohn's disease. In some embodiments, the inflammatory bowel disease is ulcerative colitis.

In another aspect, the disclosure provides an injectable dosage form of an 4β7 binding antibody consisting of (a) a heavy chain consisting of an amino acid sequence according to SEQ ID NO: 1; and (b) a light chain consisting of an amino acid sequence according to SEQ ID NO: 3, wherein the α4β7 binding antibody has an average serum half-life greater than about 10 days in cynomolgus monkeys.

In some embodiments, the average serum half-life is about 17 days or greater in cynomolgus monkeys.

In certain embodiments, the injectable dosage form is an injectable liquid formulation.

In certain embodiments, the α4β7 binding antibody is present at a concentration of at least 180 mg/mL.

In some embodiments, the injectable liquid formulation does not comprise citrate.

In one aspect, the disclosure provides a method of treating a disease in a patient in need thereof, the method comprising: administering to a subject in need thereof (a) an effective amount of an induction dose of an α4β7 binding antibody, and (b) an effective amount of one or more maintenance doses of the α4β7 binding antibody, wherein the one or more maintenance doses are administered subcutaneously at least eight weeks apart, wherein the α4β7 binding antibody consists of: (a) a heavy chain consisting of an amino acid sequence according to SEQ ID NO: 1; and (b) a light chain consisting of an amino acid sequence according to SEQ ID NO: 3.

In certain embodiments, the disease is an inflammatory bowel disease. In some embodiments, the inflammatory bowel disease is Crohn's disease. In some embodiments, the inflammatory bowel disease is ulcerative colitis.

In certain embodiments, the effective amount of the induction dose of the α4β7 binding antibody is at least 600 mg, and the effective amount of each of the one or more maintenance doses of the α4β7 binding antibody is at least 300 mg.

In certain embodiments, the effective amount of the induction dose of the α4β7 binding antibody is about 600 mg and the effective amount of each of the one or more maintenance doses of the α4β7 binding antibody is about 300 mg.

In some embodiments, the effective amount of the induction dose of the α4β7 binding antibody is administered subcutaneously.

In some embodiments, the effective amount of the induction dose of the α4β7 binding antibody is administered intravenously.

In some embodiments, the one or more maintenance doses are administered subcutaneously about 12 weeks apart.

In some embodiments, the one or more maintenance doses are administered subcutaneously about 26 weeks apart.

In some embodiments, the induction dose comprises a dosage amount of the α4β7 binding antibody that is about 2 or more times higher than a dosage amount of each of the one or more maintenance doses.

In one aspect, the disclosure provides a method of achieving $C_{trough}$ of 35 μg/mL or greater for a an α4β7 binding antibody in a subject in need thereof six weeks following administration of the α4β7 binding antibody to the subject, the method comprising administering to the subject in need thereof at least about 600 mg of the α4β7 binding antibody, wherein the α4β7 binding antibody consists of: (a) a heavy chain consisting of an amino acid sequence according to SEQ ID NO: 1; and (b) a light chain consisting of an amino acid sequence according to SEQ ID NO: 3.

In certain embodiments, from about 600 mg to about 1200 mg of the α4β7 binding antibody is administered intravenously.

In certain embodiments, from about 600 mg to about 1200 mg of the α4β7 binding antibody is administered subcutaneously.

In some embodiments, about 600 mg of the α4β7 binding antibody is administered intravenously.

In some embodiments, about 600 mg of the α4β7 binding antibody is administered subcutaneously.

In some embodiments, the method further comprises administering to the subject in need thereof at least about 300 mg of the α4β7 binding antibody, wherein the administration of the at least about 300 mg of the α4β7 binding antibody results in a steady state $C_{trough}$ of at least 6 μg/mL. In certain embodiments, the administration results in a serum $C_{avgW0-W12}$ of at least 60 μg/mL.

In some embodiments, the administration of the at least about 600 mg of the α4β7 binding antibody results in a serum $C_{avgW30-W40}$ of at least 30 μg/mL.

In some embodiments, the method further comprises administering to the subject in need thereof at least about 300 mg of the α4β7 binding antibody and wherein administration results in an average serum concentration of the α4β7 binding antibody above 35 μg/mL for ten weeks following the administration of the at least about 300 mg of the α4β7 binding antibody.

In some embodiments, the method further comprises administering subcutaneously to the subject in need thereof at least about 300 mg of the α4β7 binding antibody four weeks after administration of last dosage amount of the α4β7 binding antibody.

In some embodiments, the method further comprises administering subcutaneously to the subject a maintenance dose of at least about 600 mg of the α4β7 binding antibody every twenty-six weeks after administration of the last dose of the α4β7 binding antibody.

In one aspect, the disclosure provides an α4β7 binding antibody consisting of: (a) a heavy chain consisting of an amino acid sequence according to SEQ ID NO: 1, and (b) a light chain consisting of an amino acid sequence according to SEQ ID NO: 3.

In some embodiments, the disclosure provides an isolated nucleic acid encoding the heavy chain and/or light chain of the α4β7 binding antibody, which antibody consists of (a) a heavy chain consisting of an amino acid sequence according to SEQ ID NO: 1, and (b) a light chain consisting of an amino acid sequence according to SEQ ID NO: 3. In some embodiments, the isolated nucleic acid encodes SEQ ID NO: 1. In some embodiments, the isolated nucleic acid encodes SEQ ID NO: 3.

In certain embodiments, the disclosure provides a recombinant host cell comprising an isolated nucleic acid encoding the heavy chain and/or light chain of the α4β7 binding antibody, which antibody consists of (a) a heavy chain consisting of an amino acid sequence according to SEQ ID NO: 1, and (b) a light chain consisting of an amino acid sequence according to SEQ ID NO: 3. In some embodiments, the host cell comprises an isolated nucleic acid encodes SEQ ID NO: 1. In some embodiments, the host cell comprises an isolated nucleic acid encodes SEQ ID NO: 3.

In certain embodiments, the disclosure provides an expression vector comprising an isolated nucleic acid encoding the heavy chain and/or light chain of the α4β7 binding antibody, which antibody consists of (a) a heavy chain consisting of an amino acid sequence according to SEQ ID NO: 1, and (b) a light chain consisting of an amino acid sequence according to SEQ ID NO: 3. In some embodiments, the expression vector comprises an isolated nucleic acid encodes SEQ ID NO: 1. In some embodiments, the expression vector comprises an isolated nucleic acid encodes SEQ ID NO: 3.

In some embodiments, the disclosure provides a multi-dose regimen, a dosing regimen, an injectable dosage form, and/or a method, each as provided herein, wherein the disease in a gastrointestinal inflammatory disease.

In certain embodiments, the disclosure provides a multi-dose regimen, a dosing regimen, an injectable dosage form, a method, and/or an antibody, each as provided herein, wherein the α4β7 binding antibody has an average serum half-life greater than about 10 days in cynomolgus monkeys. In some embodiments, the average serum half-life is about 17 days or greater in cynomolgus monkeys.

In certain embodiments, the disclosure provides a multi-dose regimen, a dosing regimen, an injectable dosage form, a method, and/or an antibody, each as provided herein, wherein the α4β7 binding antibody has one or more of the following characteristics: (a) a melting temperature TmOnset greater than about 55° C., (b) a melting temperature TmOnset greater than 56.2° C., (c) a proportion of G0F from about 55.1% to about 60.4%, (d) a proportion of G1F from about 16.6% to about 18.8%, (e) a proportion of Man5 from about 7.3% to about 8.8%, (f) does not induce T cell activation markers CD25 or CD69, (g) does not result in release of cytokines, which cytokines are one or more of IL-6, IL-8, IL-1B, IFNγ, IL-4, IL-17, IL-2, IL-23p70 and TNF, (h) does not induce complement-dependent cytotoxicity (CDC) in primary human PBMCs and in α4β7-expressing human β-lymphoid cell, (i) does not induce antibody dependent cellular cytotoxicity (ADCC) in human NK cells, and (j) does not impact suppressive activity of regulatory T cells expressing α4β7 integrin, wherein the suppressive activity is measured by presence of elevated CD71, CD25, Ki67, granzyme B, or OX40.

BRIEF DESCRIPTION OF THE DRAWINGS

FIG. 1B: Labeled (AlexaFluor-647) Ab001 binds to α4β7-expressing cells isolated from PBMCs. FIG. 1C: Modification competing off AF647-Ab001 with unlabeled Ab001 demonstrates receptor occupancy. N=3 donors.

FIG. 2A depicts the percent inhibition of total adhesion of integrin-mediated adhesion by MAdCAM-1. The percent inhibition was calculated after treatment with increasing concentrations of either an α4β7 binding antibody or comparator antibody. The $IC_{50}$ of the α4β7 binding antibody was 86 pM and the $IC_{50}$ of the comparator antibody was 83 pM. FIG. 2B depicts the percent inhibition of total adhesion of integrin-mediated adhesion by VCAM-1, a potential off-target interaction. The percent inhibition was calculated after treatment with increasing concentrations of either an α4β7 binding antibody, comparator antibody or a positive control antibody. The positive control antibody was able to inhibit adhesion by VCAM-1, but neither the α4β7 binding antibody nor the comparator antibody were able to.

FIG. 7A depicts an induction and maintenance dosing regimen by subcutaneous (SC) route of administration based on dosing at W0 and W2 during induction. FIG. 7B depicts serum concentrations based on Q8W IV dosing of comparator antibody and Q12W SC dosing of the α4β7 binding antibody described herein (e.g., Ab001) based on the half-life of the antibodies.

FIG. 7C (right) depicts induction simulation of serum concentrations of the α4β7 binding antibody described herein (e.g., Ab001) and a comparator antibody.

FIG. 8A is a graph showing the α4β7 binding antibody described herein (e.g., Ab001) simulated human profiles at 600 mg. FIG. 8B is a graph showing α4β7 binding antibody described herein (e.g., Ab001) simulated human profiles 600 mg Q26W. FIG. 8C is a graph showing α4β7 binding antibody described herein (e.g., Ab001) simulated human profiles 400 mg, 200 mg, Q12W.

FIGS. 10A-10C are graphs showing human PK induction simulation studies for α4β7 binding antibody Ab001 relative to comparator antibody based on NHP $t_{1/2}$ data. FIG. 10A is a graph showing induction simulation of serum concentrations of Ab001 in human at 600 mg of subcutaneous dose at week 0 and 300 mg of subcutaneous dose at week 2. FIG. 10B is a graph showing induction simulation of serum concentrations of Ab001 in human at 600 mg of subcutaneous dose at week 0, and 300 mg of subcutaneous doses at week 2 and week 6. FIG. 10C is a graph showing induction simulation of serum concentrations of the comparator antibody in human at 300 mg of intravenous dose at week 0, week 2 and week 6.

FIG. 11A is a graph showing maintenance simulation of serum concentrations of Ab001 in human at 600 mg of subcutaneous dose every 26 weeks. FIG. 11B is a graph showing maintenance simulation of serum concentrations of Ab001 in human at 300 mg of subcutaneous dose every 12 weeks. FIG. 11C is a graph showing maintenance simulation of serum concentrations of the comparator antibody in human at 300 mg of intravenous dose every 8 weeks. FIG. 11D is a graph showing maintenance simulation of serum concentrations of the comparator antibody in human at 108 mg of subcutaneous dose every 2 weeks.

DETAILED DESCRIPTION

Figure 1A:
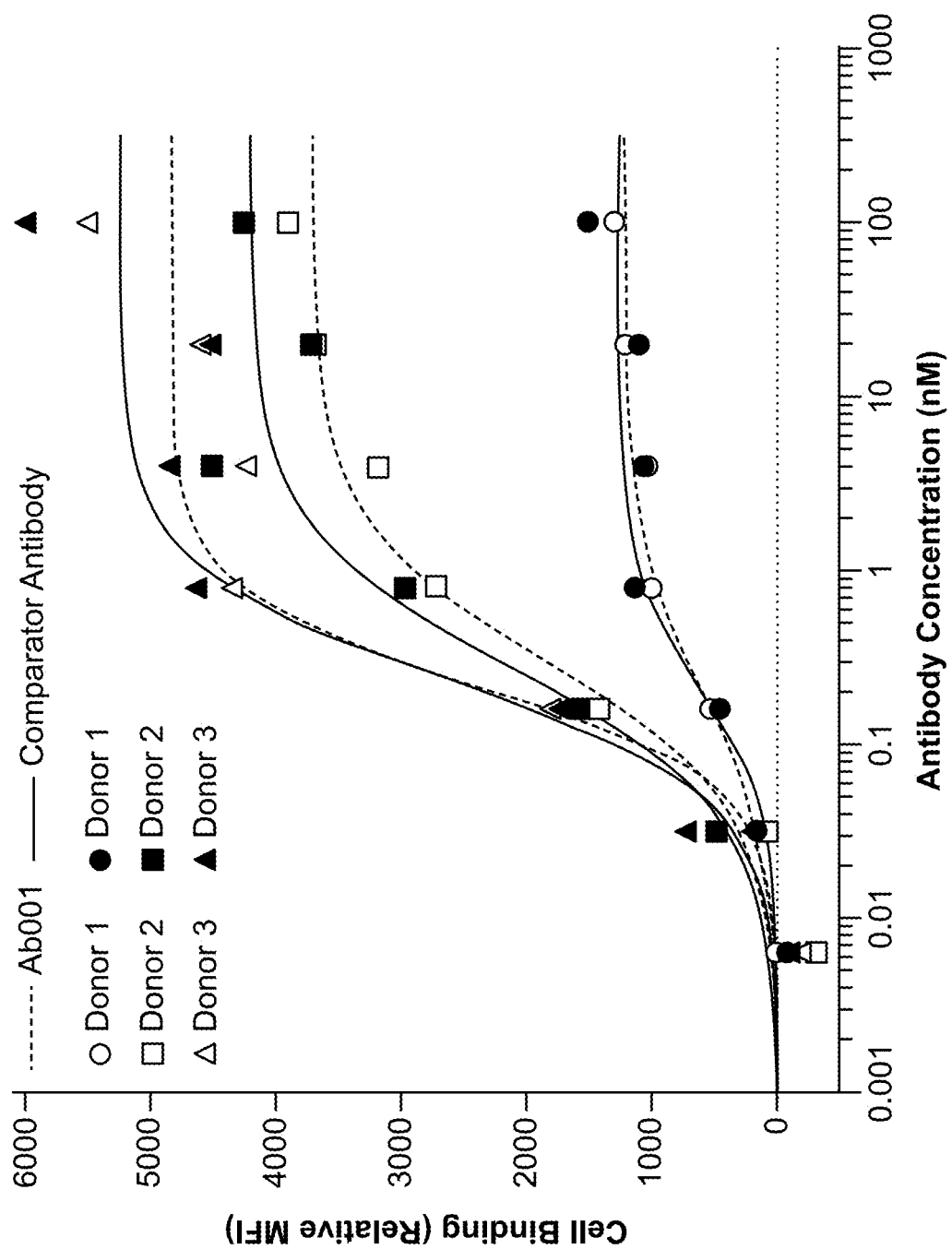
FIG. 1A depicts cell binding an α4β7 binding antibody. Cell binding was determined (Relative MFI) for increasing concentrations of α4β7 binding antibody Ab001 (dashed line, open shapes) or a comparator antibody (solid line, filled shapes) to PBMCs from three donors (Donor 1=circles; Donor 2=squares; Donor 3=triangles). $EC_{50}$ values were calculated for each donor combination and indicated in Table 2.

To facilitate an understanding of the present disclosure, a number of terms and phrases are defined below.

As used herein, unless otherwise indicated, the term "antibody" is understood to mean an intact antibody (e.g., an intact monoclonal antibody), or a fragment thereof, such as a Fc fragment of an antibody (e.g., an Fc fragment of a monoclonal antibody), or an antigen-binding fragment of an antibody (e.g., an antigen-binding fragment of a monoclonal antibody), including an intact antibody, antigen-binding fragment, or Fc fragment that has been modified, engineered, or chemically conjugated. In general, antibodies are multimeric proteins that contain four polypeptide chains. Two of the polypeptide chains are called immunoglobulin heavy chains (H chains), and two of the polypeptide chains are called immunoglobulin light chains (L chains). The immunoglobulin heavy and light chains are connected by an interchain disulfide bond. The immunoglobulin heavy chains are connected by interchain disulfide bonds. A light chain consists of one variable region (VL) and one constant region (CL). The heavy chain consists of one variable region (VH) and at least three constant regions (CH1, CH2 and CH3). The variable regions determine the binding specificity of the antibody. Each variable region contains three hypervariable regions known as complementarity determining regions (CDRs) flanked by four relatively conserved regions known as framework regions (FRs). The extent of the FRs and CDRs has been defined (Kabat, E. A., et al. (1991) Sequences of Proteins of Immunological Interest, Fifth Edition, U.S. Department of Health and Human Services, NIH Publication No. 91-3242; and Chothia, C. et al. (1987) J. Mol. Biol. 196:901-917). The three CDRs, referred to as CDR1, CDR2, and CDR3, contribute to the antibody binding specificity. Naturally occurring antibodies have been used as starting material for engineered antibodies, such as chimeric antibodies and humanized antibodies. Examples of antibody-based antigen-binding fragments include Fab, Fab', (Fab')2, Fv, single chain antibodies (e.g., scFv), minibodies, and diabodies. Examples of antibodies that have been modified or engineered include chimeric antibodies, humanized antibodies, and multispecific antibodies (e.g., bispecific antibodies). An example of a chemically conjugated antibody is an antibody conjugated to a toxin moiety.

The terms "variable domain" and "variable region" are used interchangeably and refer to the portions of the antibody or immunoglobulin domains that exhibit variability in their sequence and that are involved in determining the specificity and binding affinity of a particular antibody. Variability is not evenly distributed throughout the variable domains of antibodies; it is concentrated in sub-domains of each of the heavy and light chain variable regions. These sub-domains are called "hypervariable regions" or "complementarity determining regions" (CDRs). The more conserved (i.e., non-hypervariable) portions of the variable domains are called the "framework" regions (FRM or FR) and provide a scaffold for the six CDRs in three-dimensional space to form an antigen-binding surface.

An "Fc polypeptide" of a dimeric Fc as used herein refers to one of the two polypeptides forming the dimeric Fc domain, i.e. a polypeptide comprising C-terminal constant regions of an immunoglobulin heavy chain, capable of stable self-association. For example, an Fc polypeptide of a dimeric IgG Fc comprises an IgG CH2 and an IgG CH3 constant domain sequence. An Fc can be of the class IgA, IgD, IgE, IgG, and IgM. These classes are also designated α, δ, ε, γ, and μ, respectively. Several of these may be further divided into subclasses (isotypes), e.g., $IgG_1$, $IgG_2$, $IgG_3$, $IgG_4$, $IgA_1$, and $IgA_2$.

The terms "Fc receptor" and "FcR" are used to describe a receptor that binds to the Fc region of an antibody. For example, an FcR can be a native sequence human FcR. Generally, an FcR is one which binds an IgG antibody (a gamma receptor) and includes receptors of the FcγRI, FcγRII, and FcγRIII subclasses, including allelic variants and alternatively spliced forms of these receptors. FcγRII receptors include FcγRIIA (an "activating receptor") and FcγRIIB (an "inhibiting receptor"), which have similar amino acid sequences that differ primarily in the cytoplasmic domains thereof. Immunoglobulins of other isotypes can also be bound by certain FcRs (see, e.g., Janeway et al., *Immuno Biology*: the immune system in health and disease, (Elsevier Science Ltd., NY) (4th ed., 1999)). Activating receptor FcγRIIA contains an immunoreceptor tyrosine-based activation motif (ITAM) in its cytoplasmic domain. Inhibiting receptor FcγRIIB contains an immunoreceptor tyrosine-based inhibition motif (ITIM) in its cytoplasmic domain (reviewed in Daëron, *Annu. Rev. Immunol.* 15:203-234 (1997)). FcRs are reviewed in Ravetch and Kinet, *Annu. Rev. Immunol* 9:457-92 (1991); Capel et al., *Immunomethods* 4:25-34 (1994); and de Haas et al., *J. Lab. Clin. Med.* 126:330-41 (1995). Other FcRs, including those to be identified in the future, are encompassed by the term "FcR" herein. The term also includes the neonatal receptor, FcRn, which is responsible for the transfer of maternal IgGs to the fetus (Guyer et al., *J. Immunol.* 117:587 (1976); and Kim et al., *J. Immunol.* 24:249 (1994)).

The terms "recipient", "individual", "subject", "host", and "patient", are used interchangeably herein and in some embodiments, refer to any mammalian subject for whom diagnosis, treatment, or therapy is desired, particularly humans. "Mammal" for purposes of treatment refers to any animal classified as a mammal, including humans, domestic and farm animals, and laboratory, zoo, sports, or pet animals, such as dogs, horses, cats, cows, sheep, goats, pigs, mice, rats, rabbits, guinea pigs, monkeys etc. In some embodiments, the mammal is human. None of these terms require the supervision of medical personnel.

As used herein, the term "effective amount" refers to the amount of a compound (e.g., a compound of the present disclosure) sufficient to effect beneficial or desired results. An effective amount can be administered in one or more administrations, applications or dosages and is not intended to be limited to a particular formulation or administration route. As used herein, the term "treating" includes any effect, e.g., lessening, reducing, modulating, ameliorating or eliminating, that results in the improvement of the condition, disease, disorder, and the like, or ameliorating a symptom thereof.

As used herein, the term "pharmaceutical composition" refers to the combination of an active agent with a carrier, inert or active, making the composition especially suitable for diagnostic or therapeutic use in vivo or ex vivo.

As used herein, the term "pharmaceutically acceptable carrier" refers to any of the standard pharmaceutical carriers, such as a phosphate buffered saline solution, water, emulsions (e.g., such as an oil/water or water/oil emulsions), and various types of wetting agents. The compositions also can include stabilizers and preservatives. For examples of carriers, stabilizers and adjuvants, see e.g., Martin, Remington's Pharmaceutical Sciences, 15th Ed., Mack Publ. Co., Easton, PA (1975).

The terms "a" and "an" as used herein mean "one or more" and include the plural unless the context is inappropriate.

As used herein, all numerical values or numerical ranges include whole integers within or encompassing such ranges and fractions of the values or the integers within or encompassing ranges unless the context clearly indicates otherwise. Thus, for example, reference to a range of 90-100%, includes 91%, 92%, 93%, 94%, 95%, 95%, 96%, 97%, etc., as well as 91.1%, 91.2%, 91.3%, 91.4%, 91.5%, etc., 92.1%, 92.2%, 92.3%, 92.4%, 92.5%, etc., and so forth. In another example, reference to a range of 1-5,000-fold includes 1, 2, 3, 4, 5, 6, 7, 8, 9, 10, 11, 12, 13, 14, 15, 16, 17, 18, 19, 20, fold, etc., as well as 1.1, 1.2, 1.3, 1.4, 1.5, fold, etc., 2.1, 2.2, 2.3, 2.4, 2.5, fold, etc., and so forth.

"About" a number, as used herein, refers to range including the number and ranging from 10% below that number to 10% above that number. "About" a range refers to 10% below the lower limit of the range, spanning to 10% above the upper limit of the range.

"Percent (%) identity" refers to the extent to which two sequences (nucleotide or amino acid) have the same residue at the same positions in an alignment. For example, "an amino acid sequence is X % identical to SEQ ID NO: Y" refers to % identity of the amino acid sequence to SEQ ID NO: Y and is elaborated as X % of residues in the amino acid sequence are identical to the residues of sequence disclosed in SEQ ID NO: Y. Generally, computer programs are employed for such calculations. Exemplary programs that compare and align pairs of sequences, include ALIGN (Myers and Miller, 1988), FASTA (Pearson and Lipman, 1988; Pearson, 1990) and gapped BLAST (Altschul et al., 1997), BLASTP, BLASTN, or GCG (Devereux et al., 1984).

Throughout the description, where compositions are described as having, including, or comprising specific components, or where processes and methods are described as having, including, or comprising specific steps, it is contemplated that, additionally, there are compositions of the present disclosure that consist essentially of, or consist of, the recited components, and that there are processes and methods according to the present disclosure that consist essentially of, or consist of, the recited processing steps.

As a general matter, compositions specifying a percentage are by weight unless otherwise specified. Further, if a variable is not accompanied by a definition, then the previous definition of the variable controls.

α4β7 Integrin Binding Antibodies

Provided herein are α4β7 binding antibodies (e.g., α4β7 binding proteins, long acting α4β7 binding antibodies, long acting α4β7 binding molecules or long acting α4β7 targeting molecules. The α4β7 binding antibodies provided herein have a binding specificity for target antigen human α4β7 integrin). α4β7 binding antibodies described herein may have improved life and/or specificity. α4β7 binding antibodies described herein may have specificity for α4β7 and not related integrins including α4β1 and αEβ7.

In some embodiments, the α4β7 binding antibody comprises a heavy chain comprising an amino acid sequence having at least 80% sequence identity with an amino acid sequence according to SEQ ID NO: 1 or SEQ ID NO: 2. In some embodiments, the α4β7 binding antibody comprises a heavy chain comprising an amino acid sequence having at least 85% sequence identity with an amino acid sequence according to SEQ ID NO: 1 or SEQ ID NO: 2. In some embodiments, the α4β7 binding antibody comprises a heavy chain comprising an amino acid sequence having at least 90% sequence identity with an amino acid sequence according to SEQ ID NO: 1 or SEQ ID NO: 2. In some embodiments, the α4β7 binding antibody comprises a heavy chain comprising an amino acid sequence having at least 95% sequence identity with an amino acid sequence according to SEQ ID NO: 1 or SEQ ID NO: 2. In some embodiments, the α4β7 binding antibody comprises a heavy chain comprising an amino acid sequence having at least 96% sequence identity with an amino acid sequence according to SEQ ID NO: 1 or SEQ ID NO: 2. In some embodiments, the α4β7 binding antibody comprises a heavy chain comprising an amino acid sequence having at least 97% sequence identity with an amino acid sequence according to SEQ ID NO: 1 or SEQ ID NO: 2. In some embodiments, the α4β7 binding antibody comprises a heavy chain comprising an amino acid sequence having at least 98% sequence identity with an amino acid sequence according to SEQ ID NO: 1 or SEQ ID NO: 2. In some embodiments, the α4β7 binding antibody comprises a heavy chain comprising an amino acid sequence having at least 99% sequence identity with an amino acid sequence according to SEQ ID NO: 1 or SEQ ID NO: 2. In some embodiments, the α4β7 binding antibody comprises a heavy chain comprising an amino acid sequence having 100% sequence identity with an amino acid sequence according to SEQ ID NO: 1 or SEQ ID NO: 2. In a specific embodiment, α4β7 binding antibody comprises or consists of a heavy chain comprising an amino acid sequence having 100% sequence identity with an amino acid sequence according to SEQ ID NO: 1, including lacking a C-terminal lysine residue.

In some embodiments, the α4β7 binding antibody comprises a light chain comprising an amino acid sequence having at least 80% sequence identity with an amino acid sequence according to SEQ ID NO: 3. In some embodiments, the α4β7 binding antibody comprises a light chain comprising an amino acid sequence having at least 85% sequence identity with an amino acid sequence according to SEQ ID NO: 3. In some embodiments, the α4β7 binding antibody comprises a light chain comprising an amino acid sequence having at least 90% sequence identity with an amino acid sequence according to SEQ ID NO: 3. In some embodiments, the α4β7 binding antibody comprises a light chain comprising an amino acid sequence having at least 95% sequence identity with an amino acid sequence according to SEQ ID NO: 3. In some embodiments, the α4β7 binding antibody comprises a light chain comprising an amino acid sequence having at least 96% sequence identity with an amino acid sequence according to SEQ ID NO: 3. In some embodiments, the α4β7 binding antibody comprises a light chain comprising an amino acid sequence having at least 97% sequence identity with an amino acid sequence according to SEQ ID NO: 3. In some embodiments, the α4β7 binding antibody comprises a light chain comprising an amino acid sequence having at least 98% sequence identity with an amino acid sequence according to SEQ ID NO: 3. In some embodiments, the α4β7 binding antibody comprises a light chain comprising an amino acid sequence having at least 99% sequence identity with an amino acid sequence according to SEQ ID NO: 3. In some embodiments, the α4β7 binding antibody comprises a light chain comprising an amino acid sequence having 100% sequence identity with an amino acid sequence according to SEQ ID NO: 3.

In some embodiments, the α4β7 binding antibody comprises a heavy chain that comprises an amino acid sequence at least 60% (e.g., at least 70%, at least 80%, at least 85%, at least 90%, at least 91%, at least 92%, at least 93%, at least 94%, at least 95%, at least 96%, at least 97%, at least 98%, at least 99%, or 100%) identical to the heavy chain of an α4β7 binding antibody disclosed in Table 1, and a light chain that comprises an amino acid sequence at least 60% (e.g., at least 70%, at least 80%, at least 85%, at least 90%, at least 91%, at least 92%, at least 93%, at least 94%, at least 95%, at least 96%, at least 97%, at least 98%, at least 99%, or 100%) identical to the light chain of the same α4β7 binding antibody disclosed in Table 1. In a specific embodiment of such a heavy chain, there is no C-terminal lysine residue.

In some embodiments, the α4β7 binding antibody comprises a heavy chain comprising an amino acid sequence having at least 80% sequence identity with an amino acid sequence according to SEQ ID NO: 1 or SEQ ID NO: 2; and a light chain comprising an amino acid sequence having at least 80% sequence identity with an amino acid sequence according to SEQ ID NO: 3. In some embodiments, the α4β7 binding antibody comprises a heavy chain comprising an amino acid sequence having at least 85% sequence identity with an amino acid sequence according to SEQ ID NO: 1 or SEQ ID NO: 2; and a light chain comprising an amino acid sequence having at least 85% sequence identity with an amino acid sequence according to SEQ ID NO: 3. In some embodiments, the α4β7 binding antibody comprises a heavy chain comprising an amino acid sequence having at least 90% sequence identity with an amino acid sequence according to SEQ ID NO: 1 or SEQ ID NO: 2; and a light chain comprising an amino acid sequence having at least 90% sequence identity with an amino acid sequence according to SEQ ID NO: 3. In some embodiments, the α4β7 binding antibody comprises a heavy chain comprising an amino acid sequence having at least 95% sequence identity with an amino acid sequence according to SEQ ID NO: 1 or SEQ ID NO: 2; and a light chain comprising an amino acid sequence having at least 95% sequence identity with an amino acid sequence according to SEQ ID NO: 3. In some embodiments, the α4β7 binding antibody comprises a heavy chain comprising an amino acid sequence having at least 96% sequence identity with an amino acid sequence according to SEQ ID NO: 1 or SEQ ID NO: 2; and a light chain comprising an amino acid sequence having at least 96% sequence identity with an amino acid sequence according to SEQ ID NO: 3. In some embodiments, the α4β7 binding antibody comprises a heavy chain comprising an amino acid sequence having at least 97% sequence identity with an amino acid sequence according to SEQ ID NO: 1 or SEQ ID NO: 2; and a light chain comprising an amino acid sequence having at least 97% sequence identity with an amino acid sequence according to SEQ ID NO: 3. In some embodiments, the α4β7 binding antibody comprises a heavy chain comprising an amino acid sequence having at least 98% sequence identity with an amino acid sequence according to SEQ ID NO: 1 or SEQ ID NO: 2; and a light chain comprising an amino acid sequence having at least 98% sequence identity with an amino acid sequence according to SEQ ID NO: 3. In some embodiments, the α4β7 binding antibody comprises a heavy chain comprising an amino acid sequence having at least 99% sequence identity with an amino acid sequence according to SEQ ID NO: 1 or SEQ ID NO: 2; and a light chain comprising an amino acid sequence having at least 99% sequence identity with an amino acid sequence according SEQ ID NO: 3. In some embodiments, the α4β7 binding antibody comprises a heavy chain comprising an amino acid sequence according to SEQ ID NO: 1 or SEQ ID NO: 2; and a light chain comprising an amino acid sequence according to SEQ ID NO: 3. In a specific embodiment of such a heavy chain, there is no C-terminal lysine residue.

In some embodiments, the α4β7 binding antibody comprises a heavy chain consisting of an amino acid sequence according to SEQ ID NO: 1; and a light chain comprising an amino acid sequence according to SEQ ID NO: 3. In some embodiments, the α4β7 binding antibody comprises a heavy chain consisting of an amino acid sequence according to SEQ ID NO: 1; and a light chain comprising an amino acid sequence having at least 80% sequence identity with an amino acid sequence according to SEQ ID NO: 3. In some embodiments, the α4β7 binding antibody comprises a heavy chain comprises a heavy chain consisting of an amino acid sequence according to SEQ ID NO: 1; and a light chain comprising an amino acid sequence having at least 85% sequence identity with an amino acid sequence according to SEQ ID NO: 3. In some embodiments, the α4β7 binding antibody comprises a heavy chain consisting of an amino acid sequence according to SEQ ID NO: 1; and a light chain comprising an amino acid sequence having at least 90% sequence identity with an amino acid sequence according to SEQ ID NO: 3. In some embodiments, the α4β7 binding antibody comprises a heavy chain consisting of an amino acid sequence according to SEQ ID NO: 1; and a light chain comprising an amino acid sequence having at least 95% sequence identity with an amino acid sequence according to SEQ ID NO: 3. In some embodiments, the α4β7 binding antibody comprises a heavy chain consisting of an amino acid sequence according to SEQ ID NO: 1; and a light chain comprising an amino acid sequence having at least 96% sequence identity with an amino acid sequence according to SEQ ID NO: 3. In some embodiments, the α4β7 binding antibody comprises a heavy chain consisting of an amino acid sequence according to SEQ ID NO: 1; and a light chain comprising an amino acid sequence having at least 97% sequence identity with an amino acid sequence according to SEQ ID NO: 3. In some embodiments, the α4β7 binding antibody comprises a heavy chain consisting of an amino acid sequence according to SEQ ID NO: 1; and a light chain comprising an amino acid sequence having at least 98% sequence identity with an amino acid sequence according to SEQ ID NO: 3. In some embodiments, the α4β7 binding antibody comprises a heavy chain consisting of an amino acid sequence according to SEQ ID NO: 1; and a light chain comprising an amino acid sequence having at least 99% sequence identity with an amino acid sequence according SEQ ID NO: 3.

In some embodiments, the antigen-binding site comprises the HCDR1, HCDR2, HCDR3, LCDR1, LCDR2, and LCDR3, determined under Kabat (see Kabat et al., (1991) Sequences of Proteins of Immunological Interest, NIH Publication No. 91-3242, Bethesda), Chothia (see, e.g., Chothia C & Lesk A M, (1987), J Mol Biol 196:901-917), MacCallum (see MacCallum R M et al., (1996) J Mol Biol 262:732-745), IMGT (see Lefranc, (1999) The Immunologist, 7, 132-136), or any other CDR determination method known in the art, of the heavy chain and light chain sequences of an antibody disclosed in Table 1A.

TABLE 1A

Sequences of α4β7 binding antibodies

| SEQ ID NO | Name | Sequence |
|---|---|---|
| 1 | YTE Heavy Chain | QVQLVQSGAEVKKPGASVKVSCKGSGYTFTSYWM HWVRQAPGQRLEWIGEIDPSESNTNYNQKFKGRVT LTVDISASTAYMELSSLRSEDTAVYYCARGGYDGW DYAIDYWGQGTLVTVSSASTKGPSVFPLAPSSKSTS GGTAALGCLVKDYFPEPVTVSWNSGALTSGVHTFP AVLQSSGLYSLSSVVTVPSSSLGTQTYICNVNHKPSN TKVDKKVEPKSCDKTHTCPPCPAPELAGAPSVFLFPP KPKDTLYITREPEVTCVVVDVSHEDPEVKFNWYVD GVEVHNAKTKPREEQYNSTYRVVSVLTVLHQDWL NGKEYKCKVSNKALPAPIEKTISKAKGQPREPQVYT LPPSRDELTKNQVSLTCLVKGFYPSDIAVEWESNGQ PENNYKTTPPVLDSDGSFFLYSKLTVDKSRWQQGN VFSCSVMHEALHNHYTQKSLSLSPG |
| 2 | LS Heavy Chain | QVQLVQSGAEVKKPGASVKVSCKGSGYTFTSYWM HWVRQAPGQRLEWIGEIDPSESNTNYNQKFKGRVT LTVDISASTAYMELSSLRSEDTAVYYCARGGYDGW DYAIDYWGQGTLVTVSSASTKGPSVFPLAPSSKSTS GGTAALGCLVKDYFPEPVTVSWNSGALTSGVHTFP AVLQSSGLYSLSSVVTVPSSSLGTQTYICNVNHKPSN TKVDKKVEPKSCDKTHTCPPCPAPELAGAPSVFLFPP KPKDTLMISRTPEVTCVVVDVSHEDPEVKFNWYVD GVEVHNAKTKPREEQYNSTYRVVSVLTVLHQDWL NGKEYKCKVSNKALPAPIEKTISKAKGQPREPQVYT LPPSRDELTKNQVSLTCLVKGFYPSDIAVEWESNGQ PENNYKTTPPVLDSDGSFFLYSKLTVDKSRWQQGN VFSCSVLHEALHSHYTQKSLSLSPG |
| 3 | Light Chain | DVVMTQSPLSLPVTPGEPASISCRSSQSLAKSYGNTY LSWYLQKPGQSPQLLIYGISNRFSGVPDRFSGSGSGT DFTLKISRVEAEDVGVYYCLQGTHQPYTFGQGTKVE IKRTVAAPSVFIFPPSDEQLKSGTASVVCLLNNFYPR EAKVQWKVDNALQSGNSQESVTEQDSKDSTYSLSS TLTLSKADYEKHKVYACEVTHQGLSSPVTKSFNRGE C |

In some embodiments, the antigen-binding site comprises the HCDR1, HCDR2, HCDR3, LCDR1, LCDR2, and LCDR3 disclosed in Table 1B.

TABLE 1B

| SEQ ID NO | Name | Sequence |
|---|---|---|
| 6 | HCDR1 | SYWMH |
| 7 | HCDR2 | EIDPSESNTNYNQKFKG |
| 8 | HCDR3 | GGYDGWDYAIDY |
| 9 | LCDR1 | RSSQSLAKSYGNTYLS |
| 10 | LCDR2 | GISNRFS |
| 11 | LCDR3 | LQGTHQPYT |

In some embodiments, the α4β7 binding antibody comprises a heavy chain comprising an amino acid sequence having at least 80% sequence identity with an amino acid sequence according to SEQ ID NO: 4. In some embodiments, the α4β7 binding antibody comprises a heavy chain comprising an amino acid sequence having at least 85% sequence identity with an amino acid sequence according to SEQ ID NO: 4. In some embodiments, the α4β7 binding antibody comprises a heavy chain comprising an amino acid sequence having at least 90% sequence identity with an amino acid sequence according to SEQ ID NO: 4. In some embodiments, the α4β7 binding antibody comprises a heavy chain comprising an amino acid sequence having at least 95% sequence identity with an amino acid sequence according to SEQ ID NO: 4. In some embodiments, the α4β7 binding antibody comprises a heavy chain comprising an amino acid sequence having at least 96% sequence identity with an amino acid sequence according to SEQ ID NO: 4. In some embodiments, the α4β7 binding antibody comprises a heavy chain comprising an amino acid sequence having at least 97% sequence identity with an amino acid sequence according to SEQ ID NO: 4. In some embodiments, the α4β7 binding antibody comprises a heavy chain comprising an amino acid sequence having at least 98% sequence identity with an amino acid sequence according to SEQ ID NO: 4. In some embodiments, the α4β7 binding antibody comprises a heavy chain comprising an amino acid sequence having at least 99% sequence identity with an amino acid sequence according to SEQ ID NO: 4. In some embodiments, the α4β7 binding antibody comprises a heavy chain comprising an amino acid sequence having 100% sequence identity with an amino acid sequence according to SEQ ID NO: 4.

In some embodiments, the α4β7 binding antibody comprises a light chain comprising an amino acid sequence having at least 80% sequence identity with an amino acid sequence according to SEQ ID NO: 5. In some embodiments, the α4β7 binding antibody comprises a light chain comprising an amino acid sequence having at least 85% sequence identity with an amino acid sequence according to SEQ ID NO: 5. In some embodiments, the α4β7 binding antibody comprises a light chain comprising an amino acid sequence having at least 90% sequence identity with an amino acid sequence according to SEQ ID NO: 5. In some embodiments, the α4β7 binding antibody comprises a light chain comprising an amino acid sequence having at least 95% sequence identity with an amino acid sequence according to SEQ ID NO: 5. In some embodiments, the α4β7 binding antibody comprises a light chain comprising an amino acid sequence having at least 96% sequence identity with an amino acid sequence according to SEQ ID NO: 5. In some embodiments, the α4β7 binding antibody comprises a light chain comprising an amino acid sequence having at least 97% sequence identity with an amino acid sequence according to SEQ ID NO: 5. In some embodiments, the α4β7 binding antibody comprises a light chain comprising an amino acid sequence having at least 98% sequence identity with an amino acid sequence according to SEQ ID NO: 5. In some embodiments, the α4β7 binding antibody comprises a light chain comprising an amino acid sequence having at least 99% sequence identity with an amino acid sequence according to SEQ ID NO: 5. In some embodiments, the α4β7 binding antibody comprises a light chain comprising an amino acid sequence having 100% sequence identity with an amino acid sequence according to SEQ ID NO: 5.

In some embodiments, the α4β7 binding antibody comprises a heavy chain comprising an amino acid sequence having at least 80% sequence identity with an amino acid sequence according to SEQ ID NO: 4; and a light chain comprising an amino acid sequence having at least 80% sequence identity with an amino acid sequence according to SEQ ID NO: 5. In some embodiments, the α4β7 binding antibody comprises a heavy chain comprising an amino acid sequence having at least 85% sequence identity with an amino acid sequence according to SEQ ID NO: 4; and a light chain comprising an amino acid sequence having at least 85% sequence identity with an amino acid sequence according to SEQ ID NO: 5. In some embodiments, the α4β7 binding antibody comprises a heavy chain comprising an amino acid sequence having at least 90% sequence identity with an amino acid sequence according to SEQ ID NO: 4; and a light chain comprising an amino acid sequence having at least 90% sequence identity with an amino acid sequence according to SEQ ID NO: 5. In some embodiments, the α4β7 binding antibody comprises a heavy chain comprising an amino acid sequence having at least 95% sequence identity with an amino acid sequence according to SEQ ID NO: 4; and a light chain comprising an amino acid sequence having at least 95% sequence identity with an amino acid sequence according to SEQ ID NO: 5. In some embodiments, the α4β7 binding antibody comprises a heavy chain comprising an amino acid sequence having at least 96% sequence identity with an amino acid sequence according to SEQ ID NO: 4; and a light chain comprising an amino acid sequence having at least 96% sequence identity with an amino acid sequence according to SEQ ID NO: 5. In some embodiments, the α4β7 binding antibody comprises a heavy chain comprising an amino acid sequence having at least 97% sequence identity with an amino acid sequence according to SEQ ID NO: 4; and a light chain comprising an amino acid sequence having at least 97% sequence identity with an amino acid sequence according to SEQ ID NO: 5. In some embodiments, the α4β7 binding antibody comprises a heavy chain comprising an amino acid sequence having at least 98% sequence identity with an amino acid sequence according to SEQ ID NO: 4; and a light chain comprising an amino acid sequence having at least 98% sequence identity with an amino acid sequence according to SEQ ID NO: 5. In some embodiments, the α4β7 binding antibody comprises a heavy chain comprising an amino acid sequence having at least 99% sequence identity with an amino acid sequence according to SEQ ID NO: 4; and a light chain comprising an amino acid sequence having at least 99% sequence identity with an amino acid sequence according SEQ ID NO: 5. In some embodiments, the α4β7 binding antibody comprises a heavy chain comprising an amino acid sequence according to SEQ ID NO: 4; and a light chain comprising an amino acid sequence according to SEQ ID NO: 5.

In some embodiments, the α4β7 binding antibody comprises a heavy chain consisting of an amino acid sequence according to SEQ ID NO: 1; and a light chain comprising an amino acid sequence consisting of SEQ ID NO: 3.

In some embodiments, the α4β7 binding antibody Ab001 comprises a heavy chain consisting of an amino acid sequence according to SEQ ID NO: 1; and a light chain consisting of an amino acid sequence consisting of SEQ ID NO: 3. In some embodiments, the α4β7 binding antibody Ab001 consists of a heavy chain consisting of an amino acid sequence according to SEQ ID NO: 1; and a light chain consisting of an amino acid sequence consisting of SEQ ID NO: 3.

The α4β7 binding antibody of the disclosure can have the following properties:

| Property | Range | Exemplary Value |
| --- | --- | --- |
| Solubility (30° C.) | 100 mg/ml-300 mg/ml | 200 mg/ml |
| Solubility (5° C.) | 90 mg/ml-270 mg/ml | 206.5 mg/ml |
| Viscosity at 150 mg/ml, 25° C. | 6-16 mPa | 11.1 mPa (161 mg/mL, 25° C.) |
| pI | 7.5-7.9 | 7.7 |
| Expression titer | 1-10 | 4.7 mg/mL |

The α4β7 binding antibody of the disclosure can have the following N-glycan profiling (determined using enzymatically released N-glycans, labeled and monitored by hydrophilic interaction liquid chromatography (HILIC) coupled with a fluorescence detector (FLD)):

| Glycan | Range | Exemplary Value |
| --- | --- | --- |
| G0F | 40-75% | 60.4% (sample 1), 55.1% (sample 2) |
| G1F | 10-35% | 16.6% (sample 1) 18.8% (sample 2) |
| Man5 | 1-15% | 7.3% (sample 1) 8.8% (sample 2) |

In some embodiments, the α4β7 binding antibody comprises one or more of the following characteristics:
(a) an average serum half-life greater than about 10 days in cynomolgus monkeys,
(b) an average serum half-life of about 17 days or greater in cynomolgus monkeys,
(c) a melting temperature TmOnset greater than about 55° C.,
(d) a melting temperature TmOnset greater than 56.2° C.,
(e) does not induce T cell activation markers CD25 or CD69,
(f) does not result in release of cytokines at least 6 hours after the administration, wherein the cytokines comprise one or more of IL-6, IL-8, IL-1B, IFNγ, IL-4, IL-17, IL-2, IL-23p70 and TNF,
(g) does not induce complement-dependent cytotoxicity (CDC) in primary human PBMCs and in α4β7-expressing human β-lymphoid cell,
(h) does not induce antibody dependent cellular cytotoxicity (ADCC) in human NK cells, and
(i) does not impact suppressive activity of regulatory T cells expressing α4β7 integrin, wherein the suppressive activity is measured by presence of elevated CD71, CD25, Ki67, granzyme B, or OX40.

Fc Modifications

Provided herein are α4β7 binding antibodies comprising modified Fc regions. Unless otherwise specified herein, numbering of amino acid residues in the Fc region or constant region is according to the EU numbering system, also called the EU index, as described in Kabat et al, Sequences of Proteins of Immunological Interest, 5th Ed. Public Health Service, National Institutes of Health, Bethesda, MD, 1991.

In some embodiments, the α4β7 binding antibodies comprise a modified Fc comprising one or more modifications. In some embodiments, the one or more modifications promote selective binding of Fc-gamma receptors.

In some embodiments, one or more modifications in the modified Fc is selected from the group consisting of: S298A, E333A, K334A, K326A, F243L, R292P, Y300L, V305I, P396L, F243L, R292P, Y300L, L235V, P396L, F243L, S239D, I332E, A330L, S267E, L328F, D265S, S239E, K326A, A327H, G237F, K326E, G236A, D270L, H268D, S324T, L234F, N325L, V266L, and S267D. In some embodiments, one or more modifications in the modified Fc is selected from the group consisting of S228P, M252Y, S254T, T256E, T256D, T250Q, H285D, T307A, T307Q, T307R, T307W, L309D, Q411H, Q311V, A378V, E380A, M428L, N434A, N434S, N297A, D265A, L234A, L235A, and N434W.

In some embodiments, the modified Fc comprises a specific combination of amino acid substitutions selected from the group consisting of: L234A/L235A; V234A/G237A; L235A/G237A/E318A; S228P/L236E; H268Q/V309L/A330S/A331S; C220S/C226S/C229S/P238S; C226S/C229S/E3233P/L235V/L235A; L234F/L235E/P331S; C226S/P230S; L234A/G237A; L234A/L235A/G237A; L234A/L235A/P329G.

In some embodiments, the modified Fc comprises a specific combination of amino acid substitutions selected from the group consisting of M428L/N434S (LS); M252Y/S254T/T256E (YTE); T250Q/M428L; T307A/E380A/N434A; T256D/T307Q (DQ); T256D/T307W (DW); M252Y/T256D (YD); T307Q/Q311V/A378V (QVV); T256D/H285D/T307R/Q311V/A378V (DDRVV); L309D/Q311H/N434S (DHS); S228P/L235E (SPLE); L234A/L235A (LA); M428L/N434A; L234A/G237A (LAGA); L234A/L235A/G237A; L234A/L235A/P329G; D265A/YTE; LALA/YTE; LAGA/YTE; LALAGA/YTE; LALAPG/YTE; N297A/LS; D265A/LS; LALA/LS; LALAGA/LS; LALAPG/LS; N297A/DHS; D265A/DHS; LALA/DHS; LAGA/DHS; LALAGA/DHS; LALAPG/DHS; SP/YTE; SPLE/YTE; SP/LS; SPLE/LS; SP/DHS; SPLE/DHS; N297A/LA; D265A/LA; LALA/LA; LAGA/LA; LALAGA/LA; LALAPG/LA; N297A/N434A; D265A/N434A; LALA/N434A; LAGA/N434A; LALAGA/N434A; LALAPG/N434A; N297A/N434W; D265A/N434W; LALA/N434W; LAGA/N434W; LALAGA/N434W; LALAPG/N434W; N297A/DQ; D265A/DQ; LALA/DQ; LAGA/DQ; LALAGA/DQ; LALAPG/DQ; N297A/DW; D265A/DW; LALA/DW; LAGA/DW; LALAGA/DW; LALAPG/DW; N297A/YD; D265A/YD; LALA/YD; LAGA/YD; LALAGA/YD; LALAPG/YD; N297A/QVV; D265A/QVV; LALA/QVV; LAGA/QVV; LALAGA/QVV; LALAPG/QVV; DDRVV; N297A/DDRVV; D265A/DDRVV; LALA/DDRVV; LAGA/DDRVV; LALAGA/DDRVV; and LALAPG/DDRVV. In some embodiments, the modified Fc comprises a specific combination of amino acid substitutions selected from the group consisting of M428L/N434S (LS) and M252Y/S254T/T256E (YTE). In some embodiments, the modified Fc comprises M428L/N434S (LS) modifications. In some embodiments, the modified Fc comprises M252Y/S254T/T256E (YTE) modifications.

In some embodiments, the Fc of the α4β7 binding antibodies described herein lacks a C-terminal lysine residue (e.g., Ab001), the lack of which can be expected to decrease pI. In some embodiments, composition comprising the α4β7 binding antibodies wherein the Fc lacks C-terminal lysine residue (e.g., Ab001) has a homogeneous charge profile as compared to a composition comprising an α4β7 binding antibody, wherein the Fc comprises a C-terminal lysine residue. While the lack of C-terminal lysine residue can be expected to decrease solubility or decrease recombinant production yield, it has been discovered that truncation of C-terminal lysine in the α4β7 binding antibody yields a highly soluble protein and allows a relatively high production yield of α4β7 binding antibodies. In particular, Ab001 achieved surprising high yields (greater than 4.5 g/L) and high solubility (greater than 150 g/L).

In some embodiments, the methods provided herein wherein the α4β7 binding antibody comprises a heavy chain consisting of an amino acid sequence according to SEQ ID NO: 1; and a light chain comprising an amino acid sequence according to SEQ ID NO: 3 (e.g., Ab001) may increase FcRn binding, while exhibiting satisfactory bioavailability when the α4β7 binding antibody is administered subcutaneously.

In some embodiments, the α4β7 binding antibodies described herein include modifications to improve its ability to mediate effector function. Such modifications are known in the art and include afucosylation, or engineering of the affinity of the Fc towards an activating receptor, mainly FCGR3a for antibody-dependent cellular cytotoxicity (ADCC), and towards C1q for complement-dependent cytotoxicity (CDC).

In some aspects, an antibody provided herein comprises an IgG1 domain with reduced fucose content at position Asn 297 (EU numbering) compared to a naturally occurring IgG1 domain. Such Fc domains are known to have improved ADCC. In some aspects, such antibodies do not comprise any fucose at position Asn 297.

In some embodiments, the α4β7 binding antibody provided herein comprises glycan moieties. In some embodiments, the α4β7 binding antibody provided herein comprises an IgG1 domain with high total fucose. The major N-glycan types are G0F and G1F. In some embodiments, the α4β7 binding antibody of the disclosure has one or more of the following N-glycan profiling:
the proportion of G0F can be greater than about 40%. For example, the proportion of G0F can range from about 40% to about 75%;
the proportion of G1F can range from about 10% to about 35%; the proportion of Man5 can be less than about 20%.

In some embodiments, the proportion of Man5 can range from about 1% to about 15%. In some embodiments, the proportion of G0F in the α4β7 binding antibody is from about 40% to about 45%, from about 45% to about 50%, from about 50% to about 55%, from about 55% to about 60%, from about 60% to about 65%, from about 65% to about 70%, from about 70% to about 75%.

In some embodiments, the proportion of G1F in the α4β7 binding antibody is from about 10% to about 15%, from about 15% to about 20%, from about 20% to about 25%, from about 25% to about 30%, from about 30% to about 35%.

In some embodiments, the proportion of Man5 in the α4β7 binding antibody is from about 1% to about 5%, from about 5% to about 10%, from about 10% to about 15%.

In some embodiments, the α4β7 binding antibodies described herein comprise an Fc region with one or more amino acid substitutions which improve ADCC, such as a substitution at one or more of positions 298, 333, and 334 of the Fc region. In some embodiments, an antibody provided herein comprises an Fc region with one or more amino acid substitutions at positions 239, 332, and 330.

In some embodiments, the α4β7 binding antibodies described herein comprise an Fc region with at least one galactose residue in the oligosaccharide attached to the Fc region. Such antibody variants may have improved CDC function.

In some embodiments, the α4β7 binding antibodies described herein comprise one or more alterations that improves or diminishes C1q binding and/or CDC.

In certain embodiments, the Fc region comprises one or more amino acid substitutions, wherein the one or more substitutions result in an increase in one or more of antibody half-life, ADCC activity, ADCP activity, or CDC activity compared with the Fc without the one or more substitutions. In certain embodiments, the one or more amino acid substitutions results in increased antibody half-life at pH 6.0 compared to an antibody comprising a wild-type Fc region. In certain embodiments, the antibody has an increased half-life that is about 10,000-fold, 1,000-fold, 500-fold, 100-fold, 50-fold, 20-fold, 10-fold, 9-fold, 8-fold, 7-fold, 6-fold, 5-fold, 4.5-fold, 4-fold, 3.5-fold, 3-fold, 2.5-fold, 2-fold, 1.95-fold, 1.9-fold, 1.85-fold, 1.8-fold, 1.75-fold, 1.7-fold, 1.65-fold, 1.6-fold, 1.55-fold, 1.50-fold, 1.45-fold, 1.4-fold, 1.35-fold, 1.3-fold, 1.25-fold, 1.2-fold, 1.15-fold, 1.1-fold, or 1.05-fold longer compared to an antibody comprising a wild-type Fc region.

In certain embodiments, the Fc region comprises one or more amino acid substitutions, wherein the one or more substitutions result in a decrease in one or more of ADCC activity, ADCP activity, or CDC activity compared with the Fc without the one or more substitutions.

In certain embodiments, the Fc region binds an Fcγ Receptor selected from the group consisting of: FcγRI, FcγRIIa, FcγRIIb, FcγRIIc, FcγRIIIa, and FcγRIIIb. In certain embodiments, the Fc region binds an Fcγ Receptor with higher affinity at pH 6.0 compared to an antibody comprising a wild-type Fc region.

In some embodiments, the α4β7 binding antibodies described herein comprise an extended half-life (i.e., serum half-life). In some embodiments, the α4β7 binding antibodies described herein comprise a half-life of at least about 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 94, 96, or more than 96 days in humans. In some embodiments, the α4β7 binding antibodies described herein comprise a half-life in a range of about 28 days to about 96 days, about 28 days to about 84 days, about 28 days to about 70 days, about 28 days to about 56 days, about 28 days to about 42 days, of about 35 days to about 96 days, about 35 days to about 84 days, about 35 days to about 70 days, about 35 days to about 56 days, about 35 days to about 42 days, of about 42 days to about 96 days, about 42 days to about 84 days, about 42 days to about 70 days, or about 42 days to about 56 days in humans. In some embodiments, the α4β7 binding antibodies described herein comprise a half-life in a range of about 42 days to about 56 days in humans. In some embodiments, the α4β7 binding antibodies described herein comprise a half-life of at least about 50 days in humans. In some embodiments, the α4β7 binding antibodies described herein comprise a half-life of about 42, 43, 44, 45, 46, 47, 48, 49, 50, 51, 52, 53, 54, 55, 56 or more than 56 days in humans.

In some embodiments, the α4β7 binding antibodies described herein comprise a half-life of from about 10 days to about 25 days, from about 17 days to 23 days, from about 20 days to 22 days in non-human primates (NHPs). In some embodiments, the NHP is cynomolgus monkey. In some embodiments, the α4β7 binding antibodies described herein comprise a half-life of from about 11 days to 23 days in cynomolgus monkeys. In some embodiments, the α4β7 binding antibodies described herein comprise a half-life of from about 17 days to 23 days in cynomolgus monkeys. In some embodiments, the α4β7 binding antibodies described herein comprise a half-life of from about 19 days to 23 days in cynomolgus monkeys. In some embodiments, the α4β7 binding antibodies described herein comprise a half-life of from about 20 days to 23 days in cynomolgus monkeys. In some embodiments, the α4β7 binding antibodies described herein comprise a half-life of about 17 days in cynomolgus monkeys. In some embodiments, the α4β7 binding antibodies described herein comprise a half-life of about 20 days in cynomolgus monkeys. In some embodiments, the α4β7 binding antibodies described herein comprise a half-life of about 22 days in cynomolgus monkeys. In some embodiments, the α4β7 binding antibodies described herein comprise a half-life of from about 5 days to about 15 days, or from about 10 to 12 days in transgenic mice expressing human neonatal Fc receptor (hFcRn). In some embodiments, the transgenic mice expressing hFcRn are Tg276 mice. In some embodiments, the α4β7 binding antibodies described herein comprise a half-life of about 12 days in Tg276 mice.

Methods of measuring half-life are known in the art. In some embodiments, the half-life is measured in a rodent model, such as Tg276 mice. In some embodiments, the half-life is measured in a non-human primate, such as cynomolgus monkeys. Other animals can also be used to measure PK of α4β7 binding antibodies. In some embodiments, the half-life is measured in human. In some embodiments, the half-life is following intravenous administration. In some embodiments, the half-life is following subcutaneous administration.

In some embodiments, the α4β7 binding antibodies described herein have a half-life that is at least 20% longer than a comparator antibody. In some embodiments, the comparator antibody comprises the same complementarity determining regions and variable regions but different Fc regions. In some embodiments, the half-life of the α4β7 binding antibodies described herein protein is at least 30%, at least 40%, at least 50%, at least 60%, at least 70%, at least 80%, or at least 90% longer, at least 95% longer, at least 100% longer, at least 150% longer, at last 200% longer, at least 250% longer, at least 300% longer or at least 350% longer than the half-life of the comparator antibody. In some embodiments, the half-life of the α4β7 binding antibodies described herein is longer than the half-life of the comparator antibody by at least 2 fold, at least 3 fold, at least 4 fold, at least 5 fold, at least 6 fold, at least 7 fold, at least 8 fold, at least 9 fold, or at least 10 fold.

In some embodiments, the α4β7 binding antibodies described herein bind α4β7 with a $K_D$ lower than or equal to 20 nM, 15 nM, 10 nM, 9 nM, 8 nM, 7 nM, 6 nM, 5 nM, 4 nM, 3 nM, 2 nM, 1 nM, 0.9 nM, 0.8 nM, 0.7 nM, 0.6 nM, 0.5 nM, 0.4 nM, 0.3 nM, 0.2 nM, 0.1 nM, 90 pM, 80 pM, 70 pM, 60 pM, 50 pM, 40 pM, 30 pM, 20 pM, or 10 pM. For example, in certain embodiments, the first antigen-binding site binds α4β7 with a $K_D$ within the range of about 10 pM-about 1 nM, about 10 pM-about 0.9 nM, about 10 pM-about 0.8 nM, about 10 pM-about 0.7 nM, about 10 pM-about 0.6 nM, about 10 pM-about 0.5 nM, about 10 pM-about 0.4 nM, about 10 pM-about 0.3 nM, about 10 pM-about 0.2 nM, about 10 pM-about 0.1 nM, about 10 pM-about 50 pM, 0.1 nM-about 10 nM, about 0.1 nM-about 9 nM, about 0.1 nM-about 8 nM, about 0.1 nM-about 7 nM, about 0.1 nM-about 6 nM, about 0.1 nM-about 5 nM, about 0.1 nM-about 4 nM, about 0.1 nM-about 3 nM, about 0.1 nM-about 2 nM, about 0.1 nM-about 1 nM, about 0.1 nM-about 0.5 nM, about 0.5 nM-about 10 nM, about 0.5 nM-about 9 nM, about 0.5 nM-about 8 nM, about 0.5 nM-about 7 nM, about 0.5 nM-about 6 nM, about 0.5 nM-about 5 nM, about 0.5 nM-about 4 nM, about 0.5 nM-about 3 nM, about 0.5 nM-about 2 nM, about 0.5 nM-about 1 nM, about 1 nM-about 10 nM, about 1 nM-about 9 nM, about 1 nM-about 8 nM, about 1 nM-about 7 nM, about 1 nM about 6 nM, about 1 nM-about 5 nM, about 1 nM-about 4 nM, about 1 nM-about 3 nM, about 1 nM-about 2 nM, about 2 nM-about 10 nM, about 3 nM-about 10 nM, about 4 nM-about 10 nM, about 5 nM-about 10 nM, about 6 nM-about 10 nM, about 7 nM-about 10 nM, about 8 nM-about 10 nM, or about 9 nM-about 10 nM. In some embodiments, the affinity is measured by SPR. In some embodiments, the affinity is measured by BLI. In some embodiments, the affinity is measured by KinExA.

Methods of Treatment and Dosage Regimens

Described herein, in certain embodiments, are methods of treating a disease or disorder in a patient in need thereof, the method comprising subcutaneously or intravenously administering to the patient an effective amount of an α4β7 binding antibody disclosed herein.

Provided herein are methods of treating a disease or disorder in a patient in need thereof comprising subcutaneously administering to the patient one or more initial doses comprising an effective amount of the α4β7 binding antibody (also referred to herein as "induction dose", "induction regimen" or "induction therapy") and one or more subsequent doses comprising an effective amount of the α4β7 binding antibody (also referred to herein as "maintenance dose").

Also provided herein are methods of treating a disease or disorder in a patient in need thereof comprising intravenously administering to the patient one or more initial doses comprising an effective amount of the α4β7 binding antibody (also referred to herein as "induction dose", "induction regimen" or "induction therapy") and one or more subsequent doses comprising an effective amount of the α4β7 binding antibody (also referred to herein as "maintenance dose"). As used herein, "maintenance dose", "maintenance regimen" and "maintenance therapy" are used interchangeably and is administered after induction dose(s) to continue the response achieved by induction dose(s) of α4β7 binding antibody.

In some embodiments, a single or more than one induction dose is administered, followed by maintenance doses. The disclosure contemplates one, two, three, or more induction doses. An induction dose can be administered intravenously or subcutaneously.

The induction dosing can involve administration of a higher dose than a maintenance dose, more frequent administration than a maintenance dose, or both, of the α4β7 binding antibody, e.g., in case potentially by a factor of 2. Alternatively, the induction dosing amount is the same as the maintenance dosing amount.

In some embodiments, one or more induction dose(s) is greater than the maintenance dose. In some embodiments, the method comprises administering a single induction dose that is greater than the maintenance dose. For example, the induction dose can be 1.5, 2, 3, 4, 5 times higher than the maintenance dose. Alternatively, the one or more induction dose amount(s) is the same amount as the maintenance dose. In some embodiments, one or more induction dose(s) is administered subcutaneously to the patient in need thereof. Yet, in other embodiments, the one or more induction dose(s) is administered intravenously. In some embodiments, an induction dose may require one or more than one subcutaneous injection or infusion on the same day.

In some embodiments, the method comprises administering one or more induction doses, wherein the induction doses are the same or greater than the maintenance dose and/or are administered at a frequency that is greater than the administration of the maintenance dose. For example, the method comprises administering one, two, three or four induction doses of the α4β7 binding antibody. In some embodiments, a first dose is administered at day 0 and a second dose at a subsequent day, for example, day 1 to week 6, e.g. day 1, 2, 3, 4, 5, 6, 7, 8, 9, 10, 11, 12, 13, day 14, days 21, day 28, day 35, day 42. In some embodiments, the one or more induction dose(s) may require one or more than one subcutaneous injection, or one or more than one infusion on the same day.

In some embodiments, a total induction dosage amount corresponding to the sum of the one or more administrations is from about 400 mg to about 1000 mg of the α4β7 binding antibody. In some embodiments, a total induction dosage amount corresponding to the sum of the one or more administrations is from about 500 mg to about 1200 mg of the α4β7 binding antibody. In some embodiments, the total dosage amount is about 400 mg of the α4β7 binding antibody. In some embodiments, the total dosage amount is about 500 mg of the α4β7 binding antibody. In some embodiments, the total dosage amount about 600 mg of the α4β7 binding antibody. In some embodiments, the total dosage amount is about 700 mg of the α4β7 binding antibody. In some embodiments, the dosage amount is about 800 mg of the α4β7 binding antibody. In some embodiments, the total dosage amount is about 900 mg of the α4β7 binding antibody. In some embodiments, the total dosage amount is about 1000 mg of the α4β7 binding antibody. In some embodiments, the total dosage amount is about 1100 mg of the α4β7 binding antibody. In some embodiments, the total dosage amount is about 1200 mg of the α4β7 binding antibody.

In some embodiments, the one or more induction dose(s) is administered subcutaneously to the patient in need thereof. Yet, in other embodiments, the one or more induction dose(s) is administered intravenously.

In some embodiments, the maintenance regimen comprises lower doses than the induction regimen and/or further apart than in the induction regimen. In some embodiments, the maintenance dose is administered every 8, 9, 10, 11, 12, 13, 14, 15, 16, 17, 18, 20, 21, 22, 23, 24, 25, 26 or more weeks. In some embodiments, an induction dose of the α4β7 binding antibody is administered subcutaneously at day zero, and a maintenance dose is administered every 8, 9, 10, 11, 12, 13, 14, 15, 16, 17, 18, 20, 21, 22, 23, 24, 25, 26 or more weeks thereafter.

In some embodiments, one or more induction dose(s) of from about 150 mg to about 1200 mg of the α4β7 binding antibody is administered intravenously or subcutaneously at day zero. In some embodiments, one or more induction dose(s) of from about 300 mg to about 900 mg of the α4β7 binding antibody is administered intravenously or subcutaneously at day zero. In some embodiments, one or more induction dose(s) of from about 300 mg to about 400 mg of the α4β7 binding antibody is administered intravenously or subcutaneously at day zero. In some embodiments, one or more induction dose(s) of from about 400 mg to about 500 mg of the α4β7 binding antibody is administered intravenously or subcutaneously at day zero. In some embodiments, one or more induction dose(s) of from about 500 mg to about 600 mg of the α4β7 binding antibody is administered intravenously or subcutaneously at day zero. In some embodiments, one or more induction dose(s) of from about 600 mg to about 700 mg of the α4β7 binding antibody is administered intravenously or subcutaneously at day zero. In some embodiments, one or more induction dose(s) of from about 700 mg to about 800 mg of the α4β7 binding antibody is administered intravenously or subcutaneously at day zero. In some embodiments, one or more induction dose(s) of from about 800 mg to about 900 mg of the α4β7 binding antibody is administered intravenously or subcutaneously at day zero. In some embodiments, one or more induction dose(s) of from about 900 mg to about 1000 mg of the α4β7 binding antibody is administered intravenously or subcutaneously at day zero. In some embodiments, one or more induction dose(s) of from about 1000 mg to about 1100 mg of the α4β7 binding antibody is administered intravenously or subcutaneously at day zero. In some embodiments, one or more induction dose(s) of from about 1100 mg to about 1200 mg of the α4β7 binding antibody is administered intravenously or subcutaneously at day zero. In some embodiments, one or more induction dose(s) of about 150 mg of the α4β7 binding antibody is administered intravenously or subcutaneously at day zero. In some embodiments, one or more induction dose(s) of about 200 mg of the α4β7 binding antibody is administered intravenously or subcutaneously at day zero. In some embodiments, one or more induction dose(s) of about 250 mg of the α4β7 binding antibody is administered intravenously or subcutaneously at day zero. In some embodiments, one or more induction dose(s) of about 300 mg of the α4β7 binding antibody is administered intravenously or subcutaneously at day zero. In some embodiments, one or more induction dose(s) of about 350 mg of the α4β7 binding antibody is administered intravenously or subcutaneously at day zero. In some embodiments, one or more induction dose(s) of about 400 mg of the α4β7 binding antibody is administered intravenously or subcutaneously at day zero. In some embodiments, one or more induction dose(s) of about 450 mg of the α4β7 binding antibody is administered intravenously or subcutaneously at day zero. In some embodiments, one or more induction dose(s) of about 500 mg of the α4β7 binding antibody is administered intravenously or subcutaneously at day zero. In some embodiments, one or more induction dose(s) of about 550 mg of the α4β7 binding antibody is administered intravenously or subcutaneously at day zero. In some embodiments, one or more induction dose(s) of about 600 mg of the α4β7 binding antibody is administered intravenously or subcutaneously at day zero. In some embodiments, one or more induction dose(s) of about 650 mg of the α4β7 binding antibody is administered intravenously or subcutaneously at day zero. In some embodiments, one or more induction dose(s) of about 700 mg of the α4β7 binding antibody is administered intravenously or subcutaneously at day zero. In some embodiments, one or more induction dose(s) of about 750 mg of the α4β7 binding antibody is administered intravenously or subcutaneously at day zero. In some embodiments, one or more induction dose(s) of about 800 mg of the α4β7 binding antibody is administered intravenously or subcutaneously at day zero. In some embodiments, one or more induction dose(s) of about 850 mg of the α4β7 binding antibody is administered intravenously or subcutaneously at day zero. In some embodiments, one or more induction dose(s) of about 900 mg of the α4β7 binding antibody is administered intravenously or subcutaneously at day zero. In some embodiments, one or more induction dose(s) of about 950 mg of the α4β7 binding antibody is administered intravenously or subcutaneously at day zero. In some embodiments, one or more induction dose(s) of about 1000 mg of the α4β7 binding antibody is administered intravenously or subcutaneously at day zero. In some embodiments, one or more induction dose(s) of about 1050 mg of the α4β7 binding antibody is administered intravenously or subcutaneously at day zero. In some embodiments, one or more induction dose(s) of about 1100 mg of the α4β7 binding antibody is administered intravenously or subcutaneously at day zero. In some embodiments, one or more induction dose(s) of about 1150 mg of the α4β7 binding antibody is administered intravenously or subcutaneously at day zero. In some embodiments, one or more induction dose(s) of about 1200 mg of the α4β7 binding antibody is administered intravenously or subcutaneously at day zero. In some embodiments, the one or more induction dose(s) is administered subcutaneously.

In some embodiments, the method comprises administering two or more induction doses, wherein the first induction dose is greater than the second induction dose, and wherein the two or more induction doses are administered at a frequency that is greater than the administration of the maintenance dose. In some embodiments, the first induction dose is greater than second induction dose and greater than the maintenance dose, and the second induction is the same or greater than the maintenance dose. In some embodiments, one or more induction dose(s) of from about 150 mg to about 1200 mg of the α4β7 binding antibody is administered intravenously or subcutaneously at day zero. In some embodiments, the method comprises administering intravenously or subcutaneously a first induction dose is that greater than the second induction dose of the α4β7 binding antibody (e.g. a first induction dose of about 600 mg) at day zero, an administering a second induction of the α4β7 binding antibody (e.g. a second induction dose of about 150 mg) at day 14, and administering a maintenance dose that is the same or lower than the second inductions dose (e.g. about 150 mg) every two weeks thereafter. In one example, the induction doses are about 600 mg/mL at week 0 and about 300 mg/mL at week 2, with maintenance doses of about 300 mg/mL every 8 to 12 weeks after the second induction dose. In one example, the induction doses are about 600 mg/mL at week 0 and about 300 mg/mL at week 2, and about 300 mg/mL at week 6. In some embodiments, administration of the induction doses can result in plasma or serum $C_{avgW0\text{-}W6}$ of at least about 65 µg/mL, e.g. from about 65 µg/mL to about 75 µg/mL or greater, about 65 µg/mL, about 70 µg/mL, about 75 µg/mL or more. In some embodiments, administration of the induction doses can result in plasma or serum $C_{avgW0\text{-}W6}$ of about 70 µg/mL. In some embodiments, administration of the induction doses can result in plasma or serum $C_{avgW0\text{-}W12}$ of at least about 60 µg/mL, e.g. from about 60 µg/mL to about 70 µg/mL or greater, about 60 µg/mL, about 65 µg/mL, about 70 µg/mL or more. In some embodiments, administration of the induction doses can result in plasma or serum $C_{avgW0\text{-}W12}$ of about 65 µg/mL. Maintenance doses can be about 300 mg/mL at least every 8 weeks, for example every 12 weeks or every 24 weeks after the final induction dose. In some embodiments, administration of the induction doses can result in a plasma or serum $C_{avgW30\text{-}W40}$ of at least about 30 µg/mL, e.g. about 30 µg/mL, about 40 µg/mL, about 50 µg/mL, about 60 µg/mL, about 70 µg/mL or more.

In some embodiments, the plasma or serum concentration of at least about 35 µg/mL (e.g. from 35 to 40 µg/mL, from 40 to 45 µg/mL, from 45 to 50 µg/mL, from 50 to 55 µg/mL, from 55 to 60 µg/mL, e.g. 36 µg/mL, 41 µg/mL, 46 µg/mL, 51 µg/mL, 56 µg/mL, 60 µg/mL or more) is achieved in the patient for at least 4, at least 8, at least 12, at least 16, at least 20, at least 24 weeks or more (e.g. from 4 weeks to 6 weeks, from 6 weeks to 8 weeks, from 8 weeks to 10 weeks, from 10 weeks to 12 weeks, from 12 weeks to 14 weeks, from 14 weeks to 16 weeks, from 16 weeks to 18 weeks, from 18 weeks to 20 weeks, from 20 weeks to 22 weeks, from 22 weeks to 24 weeks or more) upon administration of an effective amount of the α4β7 binding antibody during the induction phase.

In some embodiments, the average plasma or serum concentration of at least about 35 µg/mL (e.g. from 35 to 40 µg/mL, from 40 to 45 µg/mL, from 45 to 50 µg/mL, from 50 to 55 µg/mL, from 55 to 60 µg/mL, e.g. 36 µg/mL, 41 µg/mL, 46 µg/mL, 51 µg/mL, 56 µg/mL, 60 µg/mL or more) is achieved in the patient over the course of the induction period. In some embodiments, the average plasma or serum concentration of at least about 45 µg/mL is achieved in the patient over the course of the induction period. In some embodiments, the average plasma or serum concentration of at least about 60 µg/mL is achieved in the patient over the course of the induction period.

In some embodiments, a maintenance dose of the α4β7 binding antibody is administered subcutaneously at least 4, at least 5, at least 6, at least 7, at least 8, at least 9, at least 10, at least 11, at least 12, at least 13, at least 14, at least 15, at least 16, at least 17, at least 18, at least 19, at least 20, at least 21, at least 22, at least 23, at least 24 weeks or more (e.g. from 4 weeks to 6 weeks, from 6 weeks to 8 weeks, from 8 weeks to 10 weeks, from 10 weeks to 12 weeks, from 12 weeks to 14 weeks, from 14 weeks to 16 weeks, from 16 weeks to 18 weeks, from 18 weeks to 20 weeks, from 20 weeks to 22 weeks, from 22 weeks to 24 weeks or more) after the administration of the final induction dose. In some embodiments, the maintenance dose is lower than the induction dose (e.g. twice, 3 times or more lower than the induction dose). In some embodiments, the maintenance dose is the same as the induction dose. In some embodiments, a maintenance dose of the α4β7 binding antibody is administered subcutaneously every 8, 9, 10, 11, 12, 13, 14, 15, 16, 17, 18, 20, 21, 22, 23, 24, 25, 26 or more weeks. In some embodiments, a maintenance dose of the α4β7 binding antibody is administered subcutaneously every 12, 13, 14, 15, 16, 17, 18, 20, 21, 22, 23, 24, 25, 26 or more weeks. In some embodiments, the maintenance dose comprises an effective amount of the α4β7 binding antibody. In some embodiments, the maintenance dose comprises from about 150 mg to about 300 mg of the α4β7 binding antibody. In some embodiments, upon administration of the maintenance dose results, an effective minimum serum or plasma concentration of the α4β7 binding antibody is achieved. In some embodiments, the plasma or serum concentration of at least about 6 µg/mL (e.g. from about 6 µg/mL to about 10 µg/mL, from about 6 µg/mL to about 20 µg/mL, from about 6 µg/mL to about 30 µg/mL e.g. 6 µg/mL, 10 µg/mL, 15 µg/mL, 20 µg/mL, 30 µg/mL or more) is achieved in the patient for at least 4, at least 8, at least 12, at least 16, at least 20, at least 24 weeks or more (e.g. from 4 weeks to 6 weeks, from 6 weeks to 8 weeks, from 8 weeks to 10 weeks, from 10 weeks to 12 weeks, from 12 weeks to 14 weeks, from 14 weeks to 16 weeks, from 16 weeks to 18 weeks, from 18 weeks to 20 weeks, from 20 weeks to 22 weeks, from 22 weeks to 24 weeks or more) upon the administration upon administration of the α4β7 binding antibody. In some embodiments, the plasma or serum concentration does not fall below 6 µg/mL between maintenance dosing intervals. In some embodiments, the plasma or serum concentration does not fall below 10 µg/mL between maintenance dosing intervals. In some embodiments, the plasma or serum concentration does not fall below 20 µg/mL between maintenance dosing intervals. In some embodiments, the plasma or serum concentration does not fall below 30 µg/mL between maintenance dosing intervals.

In some embodiments, the method comprises administering subcutaneously to the subject in need thereof one or more induction dose(s) of an α4β7 binding antibody, and administering subcutaneously to the subject in need thereof one or more maintenance dose(s) of the α4β7 binding antibody. In some embodiments, the induction dose comprises an amount to the α4β7 binding antibody about 2 or more times higher than the maintenance dose. In some embodiments, the induction dose comprises from about 150 mg to about 1200 mg of the α4β7 binding antibody. For example, the induction dose comprises from about 400 mg to about 600 mg of the α4β7 binding antibody and the maintenance dose of from about 150 mg to about 300 mg of the α4β7 binding antibody. In another example, the induction dose comprises about 400 mg of the α4β7 binding antibody and wherein the maintenance dose of about 200 mg of the α4β7 binding antibody. In some embodiments, the induction dose comprises from about 500 mg to about 1200 mg of the α4β7 binding antibody. For example, in some embodiments, the induction dose comprises about 600 mg of the α4β7 binding antibody and the maintenance dose of about 300 mg of the α4β7 binding antibody. In another example, the induction dose comprises about 1000 mg of the α4β7 binding antibody and the maintenance dose of about 300 mg of the α4β7 binding antibody. In some embodiments, the one or more induction dose comprises a total dosage amount of from about 150 mg to about 1200 mg of the α4β7 binding antibody. For example, the induction dose comprises one or more induction dose comprises a total dosage amount of from about 400 mg to about 600 mg of the α4β7 binding antibody and the maintenance dose of from about 150 mg to about 300 mg of the α4β7 binding antibody. In another example, the one or more induction dose comprises a total dosage amount of about 400 mg of the α4β7 binding antibody and the maintenance dose of about 200 mg of the α4β7 binding antibody. In some embodiments, the one or more induction dose comprises a total dosage amount of from about 500 mg to about 1200 mg of the α4β7 binding antibody. In another example the one or more induction dose comprises a total dosage amount of about 600 mg of the α4β7 binding antibody and the maintenance dose of about 300 mg of the α4β7 binding antibody. In another example, the one or more induction dose comprises a total dosage amount of about 1000 mg of the α4β7 binding antibody and the maintenance dose of about 300 mg of the α4β7 binding antibody.

In some embodiments, upon administration of the one or more induction dose(s), an effective minimum average serum or plasma concentration of the α4β7 binding antibody is achieved over the course of the induction period. In some embodiments, the average serum or plasma concentration of the α4β7 binding antibody of at least about 35 µg/mL is achieved in the patient over the course of the induction period, for example 36 µg/mL, is achieved in the patient over the course of the induction period. In some embodiments, the serum or plasma concentration of the α4β7 binding antibody of at least about 35 µg/mL is achieved in the patient for at least 12 weeks or more upon the administration of the induction dose. In some embodiments, the serum or plasma concentration of the α4β7 binding antibody of at least about 6 µg/mL (e.g. from about 6 µg/mL to about 10 µg/mL from about 6 µg/mL to about 20 µg/mL, from about 6 µg/mL to about 30 µg/mL e.g. 6 µg/mL, 10 µg/mL, 15 µg/mL, 20 µg/mL, 30 µg/mL or more) is achieved in the patient for at least 12 weeks upon the administration of the maintenance dose. In some embodiments, the serum or plasma concentration of the α4β7 binding antibody of at least about 10 µg/mL is achieved in the patient for at least 12 weeks upon the administration of the maintenance dose.

Further described herein, in certain embodiments, are methods of treating a disease or disorder in a patient in need thereof comprising subcutaneously administering to the patient about 108 mg or about 300 mg of an α4β7 binding antibody, wherein the α4β7 binding antibody comprises a heavy chain comprising an amino acid sequence according to SEQ ID NO: 1 or SEQ ID NO: 2 and a light chain comprising an amino acid sequence according to SEQ ID NO: 3; and wherein a plasma or serum concentration of the α4β7 binding antibody of at least about 35 µg/mL is achieved in the patient for at least 2 weeks or more upon the administration.

In some embodiments, the method of treating a disease or disorder in a patient in need thereof comprises subcutaneously administering to the patient one or more induction doses and one or more maintenance doses of an α4β7 binding antibody, wherein the α4β7 binding antibody comprises a heavy chain consisting of an amino acid sequence according to SEQ ID NO: 1; and a light chain comprising an amino acid sequence according to SEQ ID NO: 3; and wherein an average serum or plasma concentration of the α4β7 binding antibody of at least about 60 µg/mL is achieved in the patient during the induction period, and wherein a serum or plasma concentration of the α4β7 binding antibody of at least about 10 µg/mL is achieved in the patient for at least 12 weeks upon the administration of the maintenance dose.

In some embodiments, the average plasma or serum concentration of at least about 35 µg/mL is achieved in the patient during the induction period, for example from about 35 to about 60 µg/mL.

In some embodiments, the plasma or serum concentration of at least about 35 µg/mL is achieved in the patient for at least 2 weeks or more upon the administration of the one or more induction doses(s). In some embodiments, the plasma or serum concentration of at least about 35, 36, 37, 38, 39, 40, 41, 42, 43, 44, 45, 46, 47, 48, 49, 50, 51, 52, 53, 54, 55, 56, 57, 48, 59, 60, or more than 60 µg/mL is achieved in the patient for at least 2 weeks or more upon the administration of the one or more induction doses(s).

In some embodiments, the plasma or serum concentration of at least about 5, 10, 15, 20, 25, 30, 35, 40, 45, 50, 55, 60, or more than 60 µg/mL is achieved in the patient for at least 2 weeks or more upon the administration of the one or more induction dose(s) and/or one or more of the maintenance dose(s) of the α4β7 binding antibody. In some embodiments, the plasma or serum concentration of at least about 5, 10, 15, 20, 25, 30, 35, 40, 45, 50, 55, 60, 100, 150, or more than 150 µg/mL is achieved in the patient for at least 4 weeks or more upon administration of the one or more induction dose(s) and/or one or more of the maintenance dose(s) of the α4β7 binding antibody. In some embodiments, the plasma or serum concentration of at least about 5, 10, 15, 20, 25, 30, 35, 40, 45, 50, 55, 60, 100, 150, or more than 150 µg/mL is achieved in the patient for at least 6 weeks or more upon the administration of the one or more induction dose(s) and/or one or more of the maintenance dose(s) of the α4β7 binding antibody. In some embodiments, the plasma or serum concentration of at least about 5, 10, 15, 20, 25, 30, 35, 40, 45, 50, 55, 60, 100, 150, or more than 150 µg/mL is achieved in the patient for at least 8 weeks or more upon the administration of the one or more induction dose(s) and/or one or more of the maintenance dose(s) of the α4β7 binding antibody. In some embodiments, the plasma or serum concentration of at least about 5, 10, 15, 20, 25, 30, 35, 40, 45, 50, 55, 60, 100, 150, or more than 150 µg/mL is achieved in the patient for at least 10 weeks or more upon the administration of the one or more induction dose(s) and/or one or more of the maintenance dose(s) of the α4β7 binding antibody.

In some embodiments, the plasma or serum concentration of at least about 35 µg/mL is achieved in at least about 80% of the patients for at least 2 weeks or more upon the administration of the one or more induction dose(s) of the α4β7 binding antibody. In some embodiments, the plasma or serum concentration of at least about 35 µg/mL is achieved in at least about 85% of the patients for at least 2 weeks or more upon the administration of the one or more induction dose(s) of the α4β7 binding antibody. In some embodiments, the plasma or serum concentration of at least about 35 µg/mL is achieved in at least about 90% of the patients for at least 2 weeks or more upon the administration of the one or more induction dose(s) of the α4β7 binding antibody. In some embodiments, the plasma or serum concentration of at least about 35 µg/mL is achieved in at least about 95% of the patients for at least 2 weeks or more upon the administration of the one or more induction dose(s) of the α4β7 binding antibody. In some embodiments, the plasma or serum concentration of at least about 35 g/mL is achieved in at least about 99% of the patients for at least 2 weeks or more upon the administration of the one or more induction dose(s) of the α4β7 binding antibody.

In some embodiments, the plasma or serum concentration of at least about 60 µg/mL is achieved in at least about 80% of the patients for at least 2 weeks or more upon the administration of the one or more induction doses(s). In some embodiments, the plasma or serum concentration of at least about 60 µg/mL is achieved in at least about 85% of the patients for at least 2 weeks or more upon the administration of the one or more induction doses(s). In some embodiments, the plasma or serum concentration of at least about 60 µg/mL is achieved in at least about 90% of the patients for at least 2 weeks or more upon the administration of the one or more induction doses(s). In some embodiments, the plasma or serum concentration of at least about 60 µg/mL is achieved in at least about 95% of the patients for at least 2 weeks or more upon the administration of the one or more induction doses(s). In some embodiments, the plasma or serum concentration of at least about 60 g/mL is achieved in at least about 99% of the patients for at least 2 weeks or more upon the administration of the one or more induction doses(s).

In some embodiments, the average plasma or serum concentration of at least about 35 µg/mL is achieved in at least about 80% of the patients during the induction period. In some embodiments, the average plasma or serum concentration of at least about 35 µg/mL is achieved in at least about 85% of the patients during the induction period. In some embodiments, the average plasma or serum concentration of at least about 35 µg/mL is achieved in at least about 90% of the patients during the induction period. In some embodiments, the average plasma or serum concentration of at least about 35 µg/mL is achieved in at least about 95% of the patients during the induction period. In some embodiments, the average plasma or serum concentration of at least about 35 µg/mL is achieved in at least about 99% of the patients during the induction period.

In some embodiments, the average plasma or serum concentration of at least about 60 µg/mL is achieved in at least about 80% of the patients during the induction period. In some embodiments, the average plasma or serum concentration of at least about 60 g/mL is achieved in at least about 85% of the patients during the induction period. In some embodiments, the average plasma or serum concentration of at least about 60 g/mL is achieved in at least about 90% of the patients during the induction period. In some embodiments, the average plasma or serum concentration of at least about 60 g/mL is achieved in at least about 95% of the patients during the induction period. In some embodiments, the average plasma or serum concentration of at least about 60 µg/mL is achieved in at least about 99% of the patients during the induction period.

Further described herein, in certain embodiments, are methods of treating a disease or disorder in a patient in need thereof comprising subcutaneously administering to the patient from about 75 mg to about 300 mg of an α4β7 binding antibody, wherein the α4β7 binding antibody comprises a heavy chain comprising an amino acid sequence according to SEQ ID NO: 1 or SEQ ID NO: 2 and a light chain comprising an amino acid sequence according to SEQ ID NO: 3; and wherein a maintenance $C_{trough}$ of the α4β7 binding antibody of at least about 6 µg/mL is achieved in the patient for at least 2 weeks or more upon the administration. In some embodiments, the α4β7 antibody is a long acting engineered α4β7 binding antibody consisting of a heavy chain consisting of an amino acid sequence according to SEQ ID NO: 1, and a light chain consisting of an amino acid sequence according to SEQ ID NO: 3. In a further embodiment, the dose and administration frequency provide for a maintenance $C_{trough}$ of the α4β7 binding antibody of at least about 6 µg/mL in the patient perpetually upon the administration, and the dosing is no more frequent than every 4 weeks, or alternatively every 8 weeks, or alternatively every 12 weeks, or alternatively every 16 weeks, or alternatively every 26 weeks. In an embodiment, the dose is sufficient for annual (Q52) dosing. In a further embodiment, the dose and administration frequency provide for a maintenance $C_{trough}$ of the α4β7 binding antibody of at least about 10 µg/mL in the patient perpetually upon the administration, and the dosing is no more frequent than every 4 weeks, or alternatively every 8 weeks, or alternatively every 12 weeks, or alternatively every 16 weeks, or alternatively every 26 weeks. The methods may be by intravenous (IV) or subcutaneous (SC) administration, or both (an IV induction dose or doses and SC maintenance dose or doses); a particular advantage of the disclosure is that is provides for subcutaneous administration of both the induction and maintenance doses.

In some embodiments, the maintenance $C_{trough}$ of at least about 6 µg/mL (for example 10 µg/mL) is achieved in the patient upon administration of the one or more maintenance dose(s). In some embodiments, the maintenance $C_{trough}$ of at least about 2, 4, 6, 8, 10, 12, 14, 16, or more than 16

µg/mL is achieved in the patient for at least 2 weeks or more upon the administration. In some embodiments, the maintenance $C_{trough}$ of at least about 2, 4, 6, 8, 10, 12, 14, 16, or more than 16 µg/mL is achieved in the patient for at least 4 weeks or more upon administration. In some embodiments, the maintenance $C_{trough}$ of at least about 2, 4, 6, 8, 10, 12, 14, 16, or more than 16 µg/mL is achieved in the patient for at least 6 weeks or more upon the administration. In some embodiments, the maintenance of at least about 2, 4, 6, 8, 10, 12, 14, 16, or more than 16 µg/mL is achieved in the patient for at least 8 weeks or more upon the administration. In some embodiments, the maintenance $C_{trough}$ of at least about 2, 4, 6, 8, 10, 12, 14, 16, or more than 16 µg/mL is achieved in the patient for at least 10 weeks or more upon the administration.

In some embodiments, the maintenance $C_{trough}$ of at least about 6 µg/mL is achieved in at least about 80% of the patients for at least 2 weeks or more upon the administration. In some embodiments, the maintenance $C_{trough}$ of at least about 6 µg/mL is achieved in at least about 85% of the patients for at least 2 weeks or more upon the administration. In some embodiments, the maintenance $C_{trough}$ of at least about 6 µg/mL is achieved in at least about 90% of the patients for at least 2 weeks or more upon the administration. In some embodiments, the maintenance $C_{trough}$ of at least about 6 µg/mL is achieved in at least about 95% of the patients for at least 2 weeks or more upon the administration. In some embodiments, the maintenance $C_{trough}$ of at least about 6 µg/mL is achieved in at least about 99% of the patients for at least 2 weeks or more upon the administration.

In some embodiments, the $C_{6\text{-}wks,\ induction}$ of at least about 30 µg/mL is achieved in the patient. In some embodiments, the $C_{6\text{-}wks,\ induction}$ of at least about 35 µg/mL is achieved in the patient. In some embodiments, the $C_{6\text{-}wks,\ induction}$ of at least about 20, 25, 30, 35, 40, 45, 50, 55, 60 or more than 60 µg/mL is achieved in the patient. In some embodiments, the $C_{7\text{-}wks,\ induction}$ of at least about 20, 25, 30, 35, 40, 45, 50, 55, 60 or more than 60 µg/mL is achieved in the patient. In some embodiments, the $C_{8\text{-}wks,\ induction}$ of at least about 20, 25, 30, 35, 40, 45, 50, 55, 60 or more than 60 µg/mL is achieved in the patient. In some embodiments, the $C_{9\text{-}wks,\ induction}$ of at least 20, 25, 30, 35, 40, 45, 50, 55, 60 or more than 60 µg/mL is achieved in the patient. In some embodiments, the $C_{10\text{-}wks,\ induction}$ of at least about 20, 25, 30, 35, 40, 45, 50, 55, 60 or more than 60 45 µg/mL is achieved in the patient. In some embodiments, the $C_{11\text{-}wks,\ induction}$ of at least about 20, 25, 30, 35, 40, 45, 50, 55, 60 or more than 60 µg/mL is achieved in the patient. In some embodiments, the $C_{12\text{-}wks,\ induction}$ of at least about 20, 25, 30, 35, 40, 45, 50, 55, 60 or more than 60 µg/mL is achieved in the patient.

In some embodiments, the $C_{6\text{-}wks,\ induction}$ of at least about 35 µg/mL is achieved in at least about 80% of the patients. In some embodiments, the $C_{6\text{-}wks,\ induction}$ of at least about 35 µg/mL is achieved in at least about 85% of the patients. In some embodiments, the $C_{6\text{-}wks,\ induction}$ of at least about 35 µg/mL is achieved in at least about 90% of the patients. In some embodiments, the $C_{6\text{-}wks,\ induction}$ of at least about 35 µg/mL is achieved in at least about 95% of the patients. In some embodiments, the $C_{6\text{-}wks,\ induction}$ of at least about 35 µg/mL is achieved in at least about 99% of the patients.

In some embodiments, the $C_{6\text{-}wks,\ induction}$ of at least about 60 g/mL is achieved in at least about 80% of the patients. In some embodiments, the $C_{6\text{-}wks,\ induction}$ of at least about 60 µg/mL is achieved in at least about 85% of the patients. In some embodiments, the $C_{6\text{-}wks,\ induction}$ of at least about 60 µg/mL is achieved in at least about 90% of the patients. In some embodiments, the $C_{6\text{-}wks,\ induction}$ of at least about 60 g/mL is achieved in at least about 95% of the patients. In some embodiments, the $C_{6\text{-}wks,\ induction}$ of at least about 60 µg/mL is achieved in at least about 99% of the patients.

Provided herein is a method of achieving $C_{avgW0\text{-}W12}$ of from 60 µg/mL to 70 µg/mL or greater for an α4β7 binding antibody in a subject in need thereof, the method comprising administering to the subject in need thereof a first dosage amount of at least 600 mg of the α4β7 binding antibody, wherein the α4β7 binding antibody comprises a heavy chain consisting of an amino acid sequence according to SEQ ID NO: 1; and a light chain consisting of an amino acid sequence according to SEQ ID NO: 3. In some embodiments, the α4β7 binding antibody consists of a heavy chain consisting of an amino acid sequence according to SEQ ID NO: 1; and a light chain consisting of an amino acid sequence according to SEQ ID NO: 3

In some embodiments, administration results in a $C_{avgW0\text{-}W12}$ of at least 60 µg/mL. In some embodiments, administration results in a $C_{avgW0\text{-}W12}$ of about 65 µg/mL.

In some embodiments, administration comprises administering to the subject in need thereof the first dosage amount of at least 600 mg of the α4β7 binding antibody and a second dosage amount of at least 300 mg of the α4β7 binding antibody at least two weeks after administration of the first dosage amount of the α4β7 binding antibody.

In some embodiments, the method comprises administering the first dosage amount of at least 600 mg intravenously and the second dosage amount of at least 300 mg of the α4β7 binding antibody subcutaneously.

In some embodiments, the method comprises the first dosage amount of at least 600 mg subcutaneously and the second dosage amount of at least 300 mg of the α4β7 binding antibody subcutaneously.

In some embodiments, the method further comprises comprising administering to the subject in need thereof one or more dosage amount of at least 300 mg of the α4β7 binding antibody at least four weeks after administration of the second dosage amount of the α4β7 binding antibody. In some embodiments, the one or more dosage amount of the α4β7 binding antibody is administered subcutaneously.

In some embodiments, the method comprises administering to the subject in need thereof at least 600 mg of the α4β7 binding antibody every twenty-six weeks after administration of the second dosage amount of the α4β7 binding antibody.

Provided herein is a method of achieving $C_{avgW0\text{-}W6}$ of from 65 µg/mL to 75 µg/mL or greater for an α4β7 binding antibody in a subject in need thereof, the method comprising administering to the subject in need thereof a first dosage amount of at least 600 mg of the α4β7 binding antibody, wherein the α4β7 binding antibody comprises a heavy chain consisting of an amino acid sequence according to SEQ ID NO: 1; and a light chain consisting of an amino acid sequence according to SEQ ID NO: 3. In some embodiments, the α4β7 binding antibody consists of a heavy chain consisting of an amino acid sequence according to SEQ ID NO: 1; and a light chain consisting of an amino acid sequence according to SEQ ID NO: 3.

In some embodiments, administration results in a $C_{avgW0\text{-}W6}$ of about 70 µg/mL. In some embodiments, administration results in a $C_{avgW0\text{-}W12}$ of about 65 µg/mL.

In some embodiments, the administering comprises administering to the subject in need thereof a first dosage amount of at least 600 mg of the α4β7 binding antibody and a second dosage amount of at least 300 mg of the α4β7 binding antibody at least two weeks after administration of the first dosage amount of at least 600 mg of the α4β7 binding antibody.

In some embodiments, the method comprises administering the first dosage amount of the α4β7 binding antibody intravenously and the second dosage amount of the α4β7 binding antibody subcutaneously.

In some embodiments, the method comprises administering the first dosage amount and the second dosage amount of the α4β7 binding antibody subcutaneously.

In some embodiments, the method further comprises administering to the subject in need thereof one or more additional dosage amount of at least 300 mg of the α4β7 binding antibody at least four weeks after administration of the second dosage amount of the α4β7 binding antibody.

In some embodiments, the method comprises administering the one or more additional dosage amount of the α4β7 binding antibody subcutaneously.

In some embodiments, the method further comprises administering to the subject in need thereof at least 600 mg of the α4β7 binding antibody every twenty-six weeks after administration of second dosage amount of the α4β7 binding antibody.

In some embodiments, the administration of the one or more dosage amount of the α4β7 binding antibody results in $C_{avg}$ of from 40 µg/mL to 50 µg/mL or greater. In some embodiments, the administration of the one or more dose of the α4β7 binding antibody results in $C_{avg}$ of about 45 µg/mL.

Provided herein is a method of achieving $C_{trough}$ of 35 µg/mL or greater for an α4β7 binding antibody in a subject in need thereof six weeks following administration of the α4β7 binding antibody to the subject, the method comprising administering to the subject in need thereof at least 600 mg of the α4β7 binding antibody, wherein the α4β7 binding antibody comprises a heavy chain consisting of an amino acid sequence according to SEQ ID NO: 1; and a light chain consisting of an amino acid sequence according to SEQ ID NO: 3. In some embodiments, the α4β7 binding antibody consists of a heavy chain consisting of an amino acid sequence according to SEQ ID NO: 1; and a light chain consisting of an amino acid sequence according to SEQ ID NO: 3.

In some embodiments, the administration of the at least 600 mg of the α4β7 binding antibody results in a serum $C_{avg W0-W12}$ of at least 60 µg/mL. In some embodiments, the administration of the at least 600 mg of the α4β7 binding antibody results in a serum $C_{avg W30-W40}$ of at least 30 µg/mL.

In some embodiments, the at least 600 mg of the α4β7 binding antibody is administered intravenously. In other embodiments, the at least 600 mg of the α4β7 binding antibody is administered subcutaneously.

In some embodiments, the method further comprises administering to the subject in need thereof at from about 120 to about 450 mg of the α4β7 binding antibody, wherein the administration of the from about 120 to about 450 mg of the α4β7 binding antibody results in a steady state $C_{trough}$ of at least 6 µg/mL. In some embodiments, the method further comprises administering to the subject in need thereof at least 120 mg of the α4β7 binding antibody, wherein the administration of the at least 120 mg of the α4β7 binding antibody results in a steady state $C_{trough}$ of at least 6 µg/mL. In some embodiments, the method further comprises administering to the subject in need thereof at least 300 mg of the α4β7 binding antibody, wherein the administration of the at least 300 mg of the α4β7 binding antibody results in a steady state $C_{trough}$ of at least 6 µg/mL.

In some embodiments, the method further comprises administering to the subject in need thereof at least 300 mg of the α4β7 binding antibody resulting in an average serum concentration of the α4β7 binding antibody above 35 µg/mL for ten weeks following the administration of the at least 300 mg of the α4β7 binding antibody. In some embodiments, the method results in a serum $C_{avg W0-W12}$ of at least 60 µg/mL. In some embodiments, the administration of the at least 300 mg of the α4β7 binding antibody results in a serum $C_{avg W30-W40}$ of at least 30 µg/mL.

In some embodiments, the method further comprises administering to the subject in need thereof at least 300 mg of the α4β7 binding antibody and results in an average serum concentration of the α4β7 binding antibody above 35 µg/mL for ten weeks following the administration of the at least 300 mg of the α4β7 binding antibody.

In some embodiments, the method further comprises administering subcutaneously to the subject in need thereof at least 300 mg of the α4β7 binding antibody four weeks after administration of last dosage amount of the α4β7 binding antibody.

In some embodiments, the method further comprises administering subcutaneously to the subject a maintenance dose of at least 600 mg of the α4β7 binding antibody every twenty-six weeks after administration of the last dose of the α4β7 binding antibody.

Provided herein are multidose regimen for use in treating a disease in a subject in need thereof comprising a first injectable liquid formulation comprising a total dosage amount of at least 500 mg of an α4β7 binding antibody; and a second injectable liquid formulation comprising a total dosage amount of at least 120 mg of the α4β7 binding antibody, wherein the α4β7 binding antibody comprises a heavy chain consisting of an amino acid sequence according to SEQ ID NO: 1, and a light chain consisting of an amino acid sequence according to SEQ ID NO: 3. In some embodiments, the α4β7 binding antibody consists of a heavy chain consisting of an amino acid sequence according to SEQ ID NO: 1; and a light chain consisting of an amino acid sequence according to SEQ ID NO: 3. In some embodiments, the second injectable liquid formulation comprises a total dosage amount of about 300 mg of the α4β7 binding antibody. In some embodiments, the first injectable liquid formulation is for intravenous administration. In some embodiments, the first injectable liquid formulation is a single dose or a multidose formulation. In some embodiments, the second injectable liquid formulation is for subcutaneous administration. In some embodiments, the second injectable liquid formulation is a single dose or a multidose formulation.

Provided herein are multidose regimen for use in treating a disease in a subject in need thereof comprising (a) a first injectable liquid formulation comprising a total dosage amount of at least 500 mg of a α4β7 binding antibody; and (b) a second injectable liquid formulation comprising a total dosage amount of at least 300 mg of the α4β7 binding antibody, wherein the α4β7 binding antibody comprises: (i) a heavy chain consisting of an amino acid sequence according to SEQ ID NO: 1, and (ii) a light chain consisting of an amino acid sequence according to SEQ ID NO: 3. In some embodiments, the α4β7 binding antibody consists of a heavy chain consisting of an amino acid sequence according to SEQ ID NO: 1; and a light chain consisting of an amino acid sequence according to SEQ ID NO: 3.

In some embodiments, the first injectable liquid formulation comprises a total dosage amount of about 600 mg of the α4β7 binding antibody. In some embodiments, the first injectable liquid formulation comprises a total dosage amount of about 1000 mg of the α4β7 binding antibody.

In some embodiments, the second injectable liquid formulation comprises a total dosage amount of about 300 mg of the α4β7 binding antibody.

In some embodiments, the first injectable liquid formulation is for intravenous administration. In some embodiments, the first injectable liquid formulation is a single dose or a multidose formulation. In some embodiments, the second injectable liquid formulation is for subcutaneous administration. In some embodiments, the second injectable liquid formulation is a single dose or a multidose formulation.

Provided herein is a dosing regimen for use in treating a disease in a subject in need thereof, the dosing regimen comprising a first formulation comprising a total dosage amount of at least about 5500 mg of an α4β7 binding antibody for administration to the subject; a second formulation comprising a total dosage amount of at least about 120 mg of the α4β7 binding antibody for subcutaneous administration to the subject after the first formulation, and thereafter as a maintenance dose at least eight weeks after administration of the second formulation, wherein the α4β7 binding antibody comprises a heavy chain consisting of an amino acid sequence according to SEQ ID NO: 1, and a light chain consisting of an amino acid sequence according to SEQ ID NO: 3. In some embodiments, the α4β7 binding antibody consists of a heavy chain consisting of an amino acid sequence according to SEQ ID NO: 1; and a light chain consisting of an amino acid sequence according to SEQ ID NO: 3. In some embodiments, the first injectable liquid formulation comprises a total dosage amount of from about 500 mg to about 1200 mg of the α4β7 binding antibody. In some embodiments, the first injectable liquid formulation comprises a total dosage amount of about 600 mg of the α4β7 binding antibody. In some embodiments, the first injectable liquid formulation comprises a total dosage amount of about 1000 mg of the α4β7 binding antibody. In some embodiments, the second injectable liquid formulation comprises a total dosage amount of about 120 mg to about 450 mg of the α4β7 binding antibody. In some embodiments, the second injectable liquid formulation comprises a total dosage amount of about 300 mg of the α4β7 binding antibody. In some embodiments, the second formulation is administered at least two weeks after the first formulation, and thereafter as a maintenance dose at least eight weeks after administration of the second formulation.

Provided herein is a dosing regimen for use in treating a disease in a subject in need thereof, the dosing regimen comprising: (a) a first formulation comprising a total dosage amount of at least about 600 mg of an α4β7 binding antibody for administration to the subject; (b) a second formulation comprising a total dosage amount of at least about 300 mg of the α4β7 binding antibody for subcutaneous administration to the subject at least two weeks after the first formulation, and thereafter as a maintenance dose at least eight weeks after administration of the second formulation, wherein the α4β7 binding antibody comprises: (i) a heavy chain consisting of an amino acid sequence according to SEQ ID NO: 1, and (ii) a light chain consisting of an amino acid sequence according to SEQ ID NO: 3. In some embodiments, the α4β7 binding antibody consists of a heavy chain consisting of an amino acid sequence according to SEQ ID NO: 1; and a light chain consisting of an amino acid sequence according to SEQ ID NO: 3.

In some embodiments, the first formulation is for subcutaneous administration. On other embodiments, the first formulation is for intravenous administration.

In some embodiments, the first formulation comprises a total dosage amount of about 600 mg of the α4β7 binding antibody. In some embodiments, the second formulation comprises a total dosage amount of about 300 mg of the α4β7 binding antibody.

In some embodiments, the first formulation dosing regimen comprises a single or multiple injections. In some embodiments, the second formulation dosing regimen comprises a single or multiple injections.

In some embodiments, the first formulation and the second formulation do not contain citrate. In some embodiments, the first formulation or second formulation or both formulations comprise one or more of: histidine; arginine or a salt thereof; ethylenediaminetetraacetic acid (EDTA); and polysorbate 80.

Provided herein is an injectable dosage form of an α4β7 binding antibody comprising: a heavy chain consisting of an amino acid sequence according to SEQ ID NO: 1; and a light chain consisting of an amino acid sequence according to SEQ ID NO: 3, wherein the α4β7 binding antibody has an average serum half-life greater than 6 days in cynomolgus monkeys. In some embodiments, the α4β7 binding antibody has an average serum half-life greater than 10 days in cynomolgus monkeys. In some embodiments, the α4β7 binding antibody consists of a heavy chain consisting of an amino acid sequence according to SEQ ID NO: 1; and a light chain consisting of an amino acid sequence according to SEQ ID NO: 3.

In some embodiments, the average serum half-life is about 17 days or greater in cynomolgus monkeys. In some embodiments, the average serum half-life is 22 days in cynomolgus monkeys.

In some embodiments, the injectable dosage form comprises at least about 100 mg/ml, at least about 150 mg/ml, at least about 180 mg/ml, or at least about 200 mg/ml of the α4β7 binding antibody. For example, the injectable dosage form comprises from at least about 100 mg/ml to at least 110 mg/ml, from at least about 110 mg/ml to at least 120 mg/ml, from at least about 120 mg/ml to at least 130 mg/ml, from at least about 130 mg/ml to at least 140 mg/ml, from at least about 140 mg/ml to at least 150 mg/ml, from at least about 150 mg/ml to at least 160 mg/ml, from at least about 160 mg/ml to at least 170 mg/ml, from at least about 170 mg/ml to at least 180 mg/ml, from at least about 180 mg/ml to at least 190 mg/ml, from at least about 190 mg/ml to at least 200 mg/ml, from at least about 200 mg/ml to at least 210 mg/ml or more of the α4β7 binding antibody.

In some embodiments, the injectable dosage form comprises about 600 mg of the α4β7 binding antibody. In other embodiments, the injectable dosage form comprises about 1000 mg of the α4β7 binding antibody.

In some embodiments, the injectable dosage form is an injectable liquid formulation. In some embodiments, the injectable liquid formulation does not comprise citrate. In some embodiments, the injectable liquid formulation comprises one or more of: histidine; arginine or a salt thereof; ethylenediaminetetraacetic acid (EDTA); and polysorbate 80.

Provided herein are methods of treating a disease in a subject in need thereof, the method comprising administering to the subject in need thereof (a) an effective amount of an induction dose of an α4β7 binding antibody, and (b) an effective amount of one or more maintenance doses of the α4β7 binding antibody, wherein the one or more maintenance doses are administered subcutaneously at least eight weeks apart. In some embodiments, the α4β7 binding antibody comprises: (i) a heavy chain consisting of an amino acid sequence according to SEQ ID NO: 1 or SEQ ID NO: 2; and (ii) a light chain consisting of an amino acid sequence according to SEQ ID NO: 3. In some embodiments, the α4β7 binding antibody consists of a heavy chain consisting of an amino acid sequence according to SEQ ID NO: 1; and a light chain consisting of an amino acid sequence according to SEQ ID NO: 3.

In some embodiments, the effective amount of each of the one or more maintenance doses of the α4β7 binding antibody is at least about 120 mg. In some embodiments, the effective amount of each of the one or more maintenance doses of the α4β7 binding antibody is at least about 300 mg. In some embodiments, the effective amount of the induction dose of the α4β7 binding antibody is about 600 mg. In some embodiments, the effective amount of the induction dose of the α4β7 binding antibody is about 1000 mg. In some embodiments, the effective amount of the induction dose of the α4β7 binding antibody is administered subcutaneously. In some embodiments, the effective amount of the induction dose of the α4β7 binding antibody is administered intravenously. In some embodiments, the one or more maintenance doses are administered subcutaneously about 12 weeks apart. In some embodiments, the one or more maintenance doses are administered subcutaneously about 26 weeks apart. In some embodiments, the induction dose comprises a dosage amount of the α4β7 binding antibody that is about 2 or more times higher than a dosage amount of each of the one or more maintenance doses.

In some embodiments, the administration of the α4β7 binding antibody follows a biphasic decline in serum concentration. In some embodiments, repeated dosing of α4β7 binding antibody does not have a significant influence on clearance (CL) and steady-state volume of distribution (Vss). In some embodiments, pharmacokinetic is not impacted by disease state of the patient.

In some embodiments, the α4β7 binding antibody provided herein and the α4β7 binding antibody in the regimen, injectable dosage form, method provided herein has one or more of the following characteristics:
(a) an average serum half-life greater than about 6 days in cynomolgus monkeys,
(b) an average serum half-life of 22 days in cynomolgus monkeys,
(c) a melting temperature TmOnset greater than about 55° C.,
(d) a melting temperature TmOnset greater than 56.2° C.,
(e) a proportion of G0F from about 55.1% to about 60.4%,
(f) a proportion of G1F from about 16.6% to about 18.8%,
(g) a proportion of Man5 from about 7.3% to about 8.8%,
(h) does not induce T cell activation markers CD25 or CD69,
(i) does not result in release of cytokines at least 6 hours after the administration, wherein the cytokines comprise one or more of IL-6, IL-8, IL-1β, IFNγ, IL-4, IL-17, IL-2, IL-23p70 and TNF,
(j) does not induce complement-dependent cytotoxicity (CDC) in primary human PBMCs and in α4β7-expressing human β-lymphoid cell,
(k) does not induce antibody dependent cellular cytotoxicity (ADCC) in human NK cells, and
(l) does not impact suppressive activity of regulatory T cells expressing α4β7 integrin, wherein the suppressive activity is measured by presence of elevated CD71, CD25, Ki67, granzyme B, or OX40.

Described herein, in certain embodiments, are methods of treating a gastrointestinal inflammatory disease in a patient in need thereof. As used herein, the term "gastrointestinal inflammatory disease" refers to a disease of the gastrointestinal tract that involves inflammatory pathways. For example, the gastrointestinal inflammatory disease includes, but is not limited to, inflammatory bowel disease, ulcerative colitis (with or without exposure to anti-tumor necrosis factor (anti-TNF), Crohn's disease (including fistulizing Crohn's Disease), chronic pouchitis, collagenous gastritis, microscopic or collagenous colitis, colitis (including immune mediated colitis), sclerosing cholangitis (including in subjects with underlying inflammatory bowel disease, celiac enteritis, ileitis. In other aspects of the disclosure, provided herein are methods of treating Intestinal Acute Graft Versus Host Disease (aGVHD) (e.g. in subjects undergoing allogeneic hematopoietic stem cell transplantation (Allo-HSCT)), steroid-refractory acute intestinal graft-versus-host disease (GvHD) (e.g. in subjects who have undergone Allo-HSCT), Type 1 diabetes (TID) (e.g. with or without anti-TNF pre-treatment), immune checkpoint inhibitor-related colitis in subjects with genitourinary cancer or melanoma.

In some embodiments, the disease is a gastrointestinal inflammatory disease. In some embodiments, the disease is an inflammatory bowel disease. In some embodiments, the inflammatory bowel disease is Crohn's disease. In some embodiments, the inflammatory bowel disease is ulcerative colitis.

In some embodiments, the subject in need thereof has moderately to severely active ulcerative colitis. The Mayo score is a commonly used disease activity index in UC. The complete Mayo score is composed of four parts: rectal bleeding, stool frequency, physician assessment, and endoscopy appearance, each part being rated from 0 to 3, giving a total score of 0 to 12. In some embodiments, the subject in need thereof has a Mayo score 6 to 12 with endoscopic sub score ≥2. In some embodiments, administration of the α4β7 binding antibody results in clinical response defined as a reduction in complete Mayo score of 3 or more points and 30% from baseline, (or a partial Mayo score reduction of 2 or more points and 25% or greater from baseline, if the complete Mayo score was not performed at the visit) with an accompanying decrease in rectal bleeding subscore of 1 or 0. In some embodiments, administration of the α4β7 binding antibody results in clinical remission, for example results in a complete Mayo score of 2 or less points and no individual subscore greater than 1 point. Alternatively, a modified or adapted Mayo score can be used for inclusion and for the clinical remission endpoint for UC. Clinical remission by the modified or adapted Mayo score is: stool frequency subscore 0 or 1 and not greater than baseline, rectal bleeding subscore of 0, and endoscopic subscore 0 or 1 without friability.

In some embodiments, the subject in need thereof has moderately to severely active Crohn's disease. The Crohn's disease activity index (CDAI) is a commonly used disease activity index in Crohn's disease (CD) and is calculated from eight independent variables. Crohn's disease "clinical remission" refers to a CDAI score of 150 points or less. The American College of Gastroenterology and the European Crohn's and Colitis Organization define CDAI<150, 250-220, 220-450, and >450 as reflecting remission, mild disease activity, moderate disease activity, and severe disease activity, respectively. In some embodiments, administration of the α4β7 binding antibody results in clinical response defined as a ≥100-point decrease in the CDAI score from baseline. In some embodiments, administration of the α4β7 binding antibody results in clinical remission defined as a CDAI score of 150 points or less.

Described herein, in certain embodiments, are methods of treating an inflammatory bowel disease in a patient in need thereof, the method comprising subcutaneously or intravenously administering to the patient an effective amount of an α4β7 binding antibody comprising: a) a heavy chain comprising an amino acid sequence according to SEQ ID NO: 1 or SEQ ID NO: 2; and b) a light chain comprising an amino acid sequence according to SEQ ID NO: 3.

In some embodiments, the inflammatory bowel disease is Crohn's disease or ulcerative colitis. In some embodiments, the inflammatory bowel disease is ulcerative colitis.

Described herein, in certain embodiments, are methods of treating an inflammatory bowel disease in a patient in need thereof, the method comprising subcutaneously or intravenously administering to the patient an effective amount of an α4β7 binding antibody comprising: a) a heavy chain comprising an amino acid sequence according to SEQ ID NO: 1 or SEQ ID NO: 2; and b) a light chain comprising an amino acid sequence according to SEQ ID NO: 3. In some embodiments, the 4β7 binding antibody is a long acting engineered α4β7 binding antibody, consisting of a heavy chain consisting of an amino acid sequence according to SEQ ID NO: 1, and a light chain consisting of an amino acid sequence according to SEQ ID NO: 3.

In some embodiments, the α4β7 binding antibody is administered at a dose of about 75 mg to about 150 mg. In some embodiments, the α4β7 binding antibody is administered at a dose of about 150 mg to about 300 mg. In some embodiments, the α4β7 binding antibody is administered at a dose of about 250 mg to about 750 mg. In some embodiments, the α4β7 binding antibody is administered at a dose of about 300 mg to about 700 mg. In some embodiments, the α4β7 binding antibody is administered at a dose of about 700 mg to about 900 mg. In some embodiments, the α4β7 binding antibody is administered at a dose of about 300 mg to about 600 mg. In some embodiments, the α4β7 binding antibody is administered at a dose of about 300 mg to about 500 mg. In some embodiments, the α4β7 binding antibody is administered at a dose of about 300 mg to about 400 mg. In some embodiments, the α4β7 binding antibody is administered at a dose of about 400 mg to about 700 mg. In some embodiments, the α4β7 binding antibody is administered at a dose of about 400 mg to about 600 mg. In some embodiments, the α4β7 binding antibody is administered at a dose of about 300 mg to about 500 mg. In some embodiments, the α4β7 binding antibody is administered at a dose of about 500 mg to about 700 mg. In some embodiments, the α4β7 binding antibody is administered at a dose of about 700 mg to about 900 mg. In some embodiments, the α4β7 binding antibody is administered at a dose of about 500 mg to about 600 mg. In some embodiments, the α4β7 binding antibody is administered at a dose of about 600 mg to about 700 mg. In some embodiments, the α4β7 binding antibody is administered at a dose of about 75 mg, about 100 mg, about 125 mg, about 150 mg, about 175 mg, about 200 mg, about 225 mg, about 250 mg, about 275 mg, or about 300 mg, about 350 mg, about 400 mg, about 450 mg, about 500 mg, about 550 mg, about 600 mg, about 650 mg, about 700 mg, about 750 mg, about 800 mg, about 850 mg, about 900 mg. In some embodiments, the α4β7 binding antibody is administered at a dose of about 300 mg.

In some embodiments, administration of the α4β7 binding antibody is intravenous, intratumoral, intramuscular, subcutaneous, intralesional, intraintestinal, intracolonic, intrarectal, intrapouch, or intraperitoneal. In some embodiments, administration of the α4β7 binding antibody is through a parenteral route such as intravenous, intramuscular, subcutaneous, intraarterial, or intraperitoneal administration. In some embodiments, administration of the α4β7 binding antibody is intravenous or subcutaneous. In some embodiments, administration of the α4β7 binding antibody is intravenous. In some embodiments, administration of the α4β7 binding antibody is subcutaneous.

Administration of the α4β7 binding antibody can occur at various intervals. In some embodiments, the α4β7 binding antibody is administered to the patient at least once at an interval more than 8 weeks. In some embodiments, the interval is about 8 to about 12 weeks. In some embodiments, the interval is about 8 to about 16 weeks. In some embodiments, the interval is about 8 to about 20 weeks. In some embodiments, the interval is about 8 to about 24 weeks. In some embodiments, the interval is about 12 to about 26 weeks. In some embodiments, the interval is about 12 to about 22 weeks. In some embodiments, the interval is about 12 to about 18 weeks. In some embodiments, the interval is about 12 to about 14 weeks. In some embodiments, the interval is about 16 to about 26 weeks. In some embodiments, the interval is about 16 to about 22 weeks. In some embodiments, the interval is about 16 to about 18 weeks. In some embodiments, the interval is about 20 to about 26 weeks. In some embodiments, the interval is about 20 to about 22 weeks. In some embodiments, the interval is about 22 to about 26 weeks. In some embodiments, the interval is about 24 to about 26 weeks. In some embodiments, the interval is about 12 weeks. In some embodiments, the interval is about 14 weeks. In some embodiments, the interval is about 13 weeks. In some embodiments, the interval is about 16 weeks. In some embodiments, the interval is about 17 weeks. In some embodiments, the interval is about 18 weeks. In some embodiments, the interval is about 19 weeks. In some embodiments, the interval is about 20 weeks. In some embodiments, the interval is about 21 weeks. In some embodiments, the interval is about 22 weeks. In some embodiments, the interval is about 23 weeks. In some embodiments, the interval is about 24 weeks. In some embodiments, the interval is about 25 weeks. In some embodiments, the interval is about 26 weeks. In an embodiment, the dose is sufficient for annual (Q52) dosing.

Described herein, in certain embodiments, are methods of treating a disease or disorder in a patient in need thereof comprising subcutaneously administering to the patient about 108 mg or about 300 mg of an α4β7 binding antibody every four or six weeks, wherein the α4β7 binding antibody comprises a heavy chain comprising an amino acid sequence according to SEQ ID NO: 4 and a light chain comprising an amino acid sequence according to SEQ ID NO: 5; and wherein no intervening subcutaneous administration of the α4β7 binding antibody occurs during the four or six weeks. In some embodiments, the α4β7 binding antibody is administered at a dose of about 100 mg, about 125 mg, about 150 mg, about 175 mg, about 200 mg, about 225 mg, about 250 mg, about 275 mg, or about 300 mg. In some embodiments, the α4β7 binding antibody is administered every one week, two weeks, three weeks, four weeks, five weeks, six week, 7 weeks, 8 weeks, 10 weeks, 12 weeks, 14 weeks, 16 weeks, 20 weeks, 22 weeks, 24 weeks, 26 weeks, or more than 26 weeks.

In some embodiments, the induction dose comprises from about 400 mg to about 1000 mg of the α4β7 binding antibody and wherein the maintenance dose of from about 150 to about 300 mg of the α4β7 binding antibody. In some embodiments, the induction dose comprises about 600 mg of the α4β7 binding antibody and wherein the maintenance dose of about 300 mg of the α4β7 binding antibody. In some embodiments, the induction dose comprises about 1000 mg of the α4β7 binding antibody and wherein the maintenance dose of about 300 mg of the α4β7 binding antibody. In some embodiments, the induction dose comprises about 400 mg of the α4β7 binding antibody and wherein the maintenance dose of about 200 mg of the α4β7 binding antibody. In some embodiments, the induction dose comprises about 600 mg of the α4β7 binding antibody and wherein the maintenance dose of about 600 mg of the α4β7 binding antibody.

In some embodiments, the method comprises administering subcutaneously to the subject an induction dose of about 600 mg of the α4β7 binding antibody at week 0 and administering subcutaneously to the subject a maintenance dose of about 600 mg of the α4β7 binding antibody at week 26.

In some embodiments, upon administration of the one or more induction dose(s) an average serum or plasma concentration at least about 35 μg/mL of the α4β7 binding antibody is achieved in the patient during an induction period. In some embodiments, upon administration of the one or more maintenance dose(s) a serum or plasma concentration at least about 6 μg/mL, at least about 10 μg/mL, of the α4β7 binding antibody is achieved in the patient in the patient for at least 2 weeks or more.

Pharmaceutical Compositions

The present disclosure also features pharmaceutical compositions that contain a therapeutically effective amount of the α4β7 binding antibodies described herein. The composition can be formulated for use in a variety of drug delivery systems. One or more physiologically acceptable excipients or carriers can also be included in the composition for proper formulation. Suitable formulations for use in the present disclosure are found in Remington's Pharmaceutical Sciences, Mack Publishing Company, Philadelphia, Pa., 17th ed., 1985. For a brief review of methods for drug delivery, see, e.g., Langer (Science 249:1527-1533, 1990).

In some embodiments, the pharmaceutical composition is a liquid composition. In some embodiments, the pharmaceutical composition is formulated for subcutaneous administration. In some embodiments, the pharmaceutical composition is formulated for intravenous administration. In some embodiments, the liquid composition is a colorless to brown; in some embodiments, the liquid composition is clear to opalescent. In some embodiments, the liquid composition contains at least 150 mg/ml, or at least 180 mg/ml, or at least 200 mg/ml of an α4β7 binding antibody. In some embodiments, the liquid composition contains from about 150 mg/ml to about 160 mg/ml, from about 160 mg/ml to about 170 mg/ml, from about 170 mg/ml to about 10 mg/ml, from about 180 mg/ml to about 190 mg/ml, from about 190 mg/ml to about 200 mg/ml or more of a α4β7 binding antibody.

In some embodiments, a pharmaceutical composition may contain formulation materials for modifying, maintaining or preserving, for example, the pH, osmolarity, viscosity, clarity, color, isotonicity, odor, sterility, stability, rate of dissolution or release, adsorption or penetration of the composition. In such embodiments, suitable formulation materials include, but are not limited to, amino acids or salt thereof (such as glycine, glutamine, asparagine, arginine (e.g., arginine-HCl), histidine, or lysine); antimicrobials; antioxidants (such as ascorbic acid, sodium sulfite or sodium hydrogensulfite); buffers (such as borate, bicarbonate, Tris-HCl, citrates, phosphates or other organic acids); bulking agents (such as mannitol or glycine); chelating agents (such as ethylenediamine tetraacetic acid (EDTA), pentetic acid (DTPA));

complexing agents (such as caffeine, polyvinylpyrrolidone, beta-cyclodextrin or hydroxypropyl-beta-cyclodextrin); fillers; monosaccharides; disaccharides; and other carbohydrates (such as glucose, mannose or dextrins); proteins (such as serum albumin, gelatin or immunoglobulins); coloring, flavoring and diluting agents; emulsifying agents; hydrophilic polymers (such as polyvinylpyrrolidone); low molecular weight polypeptides; salt-forming counterions (such as sodium); preservatives (such as benzalkonium chloride, benzoic acid, salicylic acid, thimerosal, phenethyl alcohol, methylparaben, propylparaben, chlorhexidine, sorbic acid or hydrogen peroxide); solvents (such as glycerin, propylene glycol or polyethylene glycol); sugar alcohols (such as mannitol or sorbitol); suspending agents; surfactants or wetting agents (such as pluronics, PEG, sorbitan esters, polysorbates such as polysorbate 20, polysorbate 80, triton, tromethamine, lecithin, cholesterol, tyloxapal); stability enhancing agents (such as sucrose or sorbitol); tonicity enhancing agents (such as alkali metal halides, preferably sodium or potassium chloride, mannitol sorbitol); delivery vehicles; diluents; excipients and/or pharmaceutical adjuvants (see, Remington's Pharmaceutical Sciences, 18th ed. (Mack Publishing Company, 1990)

In some embodiments, a pharmaceutical composition is citrate-free. In some embodiments, a pharmaceutical composition may contain nanoparticles, e.g., polymeric nanoparticles, liposomes, or micelles.

In some embodiments, a pharmaceutical composition may contain a sustained- or controlled-delivery formulation. Techniques for formulating sustained- or controlled-delivery means, such as liposome carriers, bio-erodible microparticles or porous beads and depot injections, are also known to those skilled in the art. Sustained-release preparations may include, e.g., porous polymeric microparticles or semipermeable polymer matrices in the form of shaped articles, e.g., films, or microcapsules. Sustained release matrices may include polyesters, hydrogels, polylactides, copolymers of L-glutamic acid and gamma ethyl-L-glutamate, poly (2-hydroxyethyl-methacrylate), ethylene vinyl acetate, or poly-D (-)-3-hydroxybutyric acid. Sustained release compositions may also include liposomes that can be prepared by any of several methods known in the art.

Pharmaceutical compositions containing an α4β7 binding antibody disclosed herein can be presented in a dosage unit form and can be prepared by any suitable method. A pharmaceutical composition should be formulated to be compatible with its intended route of administration. Examples of routes of administration are intravenous (IV), subcutaneous (SC), intradermal, inhalation, transdermal, topical, transmucosal, intrathecal and rectal administration. In some embodiments, the α4β7 binding antibody disclosed herein is administered by intravenously. In some embodiments, the α4β7 binding antibody disclosed herein is administered intravenously or subcutaneously. In specific embodiments, the α4β7 binding antibody disclosed herein is administered subcutaneously.

Aspects of the disclosure relate to injectable dosage forms of α4β7 binding antibody. In some embodiments, the α4β7 binding antibody comprises a heavy chain consisting of an amino acid sequence according to SEQ ID NO: 1, and a light chain consisting of an amino acid sequence according to SEQ ID NO: 3. In some embodiments, the α4β7 binding antibody consists of a heavy chain consisting of an amino acid sequence according to SEQ ID NO: 1, and a light chain consisting of an amino acid sequence according to SEQ ID NO: 3. In some embodiments, the injectable dosage form is a liquid formulation. In some embodiments, the liquid formulation comprises one or more of histidine, arginine or a salt thereof, EDTA and polysorbate 80. In some embodiments, the injectable liquid formulation does not comprise citrate.

Described herein, in certain embodiments, are subcutaneous dosages form comprising at least about 150 mg of an α4β7 binding antibody comprising: a) a heavy chain comprising an amino acid sequence according to SEQ ID NO: 1 or SEQ ID NO: 2; and b) a light chain comprising an amino acid sequence according to SEQ ID NO: 3. In some embodiments, the subcutaneous dosages form comprising at least about 300 mg of an α4β7 binding antibody comprising: a) a heavy chain comprising an amino acid sequence according to SEQ ID NO: 1 or SEQ ID NO: 2; and b) a light chain comprising an amino acid sequence according to SEQ ID NO: 3.

In some embodiments, provided herein are subcutaneous dosage forms comprising at least about 150 mg of an α4β7 binding antibody comprising: a) a heavy chain comprising an amino acid sequence according to SEQ ID NO: 1; and b) a light chain comprising an amino acid sequence according to SEQ ID NO: 3. In some embodiments, provided herein are subcutaneous dosage forms comprising at least about 150 mg of an α4β7 binding antibody comprising: a) a heavy chain consisting an amino acid sequence according to SEQ ID NO: 1; and b) a light chain comprising an amino acid sequence according to SEQ ID NO: 3.

In some embodiments, provided herein are subcutaneous dosage forms comprising at least about 300 mg of an α4β7 binding antibody comprising: a) a heavy chain comprising an amino acid sequence according to SEQ ID NO: 1; and b) a light chain comprising an amino acid sequence according to SEQ ID NO: 3. In some embodiments, provided herein are subcutaneous dosage forms comprising at least about 300 mg of an α4β7 binding antibody comprising: a) a heavy chain consisting an amino acid sequence according to SEQ ID NO: 1; and b) a light chain comprising an amino acid sequence according to SEQ ID NO: 3.

Useful formulations can be prepared by methods known in the pharmaceutical art. For example, see *Remington's Pharmaceutical Sciences,* 18th ed. (Mack Publishing Company, 1990). Formulation components suitable for parenteral administration include a sterile diluent such as water for injection, saline solution, fixed oils, polyethylene glycols, glycerin, propylene glycol or other synthetic solvents; antibacterial agents such as benzyl alcohol or methyl parabens; antioxidants such as ascorbic acid or sodium bisulfite; chelating agents such as EDTA; buffers such as acetates, citrates or phosphates; and agents for the adjustment of tonicity such as sodium chloride or dextrose. In some embodiments, the formulation for parenteral administration is citrate-free.

For intravenous or subcutaneous administration, suitable carriers include physiological saline, bacteriostatic water, Cremophor ELTM (BASF, Parsippany, NJ) or phosphate buffered saline (PBS). The carrier should be stable under the conditions of manufacture and storage, and should be preserved against microorganisms. The carrier can be a solvent or dispersion medium containing, for example, water, ethanol, polyol (for example, glycerol, propylene glycol, and liquid polyethylene glycol), and suitable mixtures thereof.

An intravenous or subcutaneous drug delivery formulation may be contained in a syringe, pen, or bag. In some embodiments, the bag is connected to a channel comprising a tube and/or a needle. In some embodiments, the formulation is a lyophilized formulation or a liquid formulation. In some embodiments, the formulation is a liquid formulation. Various devices can be used to deliver liquid formulations by subcutaneous route of administration, including on-body infusion devices, autoinjector devices, prefilled syringes, and syringes. Generally, administration time depends on volume and device, and can range from seconds to minutes.

These compositions may be sterilized by conventional sterilization techniques, or may be sterile filtered. The resulting aqueous solutions may be packaged for use as-is, or lyophilized, the lyophilized preparation being combined with a sterile aqueous carrier prior to administration.

A polyol, which acts as a tonicifier and may stabilize the α4β7 binding antibody, may also be included in the formulation. The polyol is added to the formulation in an amount which may vary with respect to the desired isotonicity of the formulation. In some embodiments, the aqueous formulation is isotonic. The amount of polyol added may also be altered with respect to the molecular weight of the polyol. For example, a lower amount of a monosaccharide (e.g., mannitol) is added, compared to a disaccharide (such as trehalose). In some embodiments, the polyol which is used in the formulation as a tonicity agent is mannitol.

A detergent or surfactant may also be added to the formulation. Exemplary detergents include nonionic detergents such as polysorbates (e.g., polysorbates 20, 80 etc.) or poloxamers (e.g., poloxamer 188). The amount of detergent added is such that it reduces aggregation of the formulated antibody and/or minimizes the formation of particulates in the formulation and/or reduces adsorption. In some embodiments, the formulation may include a surfactant which is a polysorbate. In some embodiments, the formulation may contain the detergent polysorbate 80 or Tween 80. Tween 80 is a term used to describe polyoxyethylene (20) sorbitanmonooleate (see Fiedler, Lexikon der Hifsstoffe, Editio Cantor Verlag Aulendorf, 4th edi., 1996).

In embodiments, the protein product of the present disclosure is formulated as a liquid formulation. In some embodiments, the liquid formulation is prepared in combination with a sugar at stabilizing levels. In some embodiments, the liquid formulation is prepared in an aqueous carrier. In some embodiments, a stabilizer is added in an amount no greater than that which may result in a viscosity undesirable or unsuitable for intravenous administration. In some embodiments, the sugar is disaccharides, e.g., sucrose. In some embodiments, the liquid formulation may also include one or more of a buffering agent, a surfactant, and a preservative.

In some embodiments, the pH of the liquid formulation is set by addition of a pharmaceutically acceptable acid and/or base. In some embodiments, the pharmaceutically acceptable acid is hydrochloric acid. In some embodiments, the base is sodium hydroxide. In some embodiments, the pH of the liquid formulation is from about to about 3.5 to 9, 5.5 to 6.5, for example 6.0. In some embodiments, the pH of the liquid formulation is about 6.

The aqueous carrier of interest herein is one which is pharmaceutically acceptable (safe and non-toxic for administration to a human) and is useful for the preparation of a liquid formulation. Illustrative carriers include sterile water for injection (SWFI), bacteriostatic water for injection (BWFI), a pH buffered solution (e.g., phosphate-buffered saline), sterile saline solution, Ringer's solution or dextrose solution.

A preservative may be optionally added to the formulations herein to reduce bacterial action. The addition of a preservative may, for example, facilitate the production of a multi-use (multiple-dose) formulation.

The α4β7 binding antibody may be lyophilized to produce a lyophilized formulation including the proteins and a lyoprotectant. The lyoprotectant may be sugar, e.g., disaccharides. In some embodiments, the lyoprotectant is sucrose or maltose. The lyophilized formulation may also include one or more of a buffering agent, a surfactant, a bulking agent, and/or a preservative.

The amount of sucrose or maltose useful for stabilization of the lyophilized drug product may be in a weight ratio of at least 1:2 protein to sucrose or maltose. In some embodiments, the protein to sucrose or maltose weight ratio is of from 1:2 to 1:5. In some embodiments, the pH of the formulation, prior to lyophilization, is set by addition of a pharmaceutically acceptable acid and/or base. In some embodiments, the pharmaceutically acceptable acid is hydrochloric acid. In some embodiments, the pharmaceutically acceptable base is sodium hydroxide.

In some embodiments, the α4β7 binding antibody is administered at a dose of about 75 mg to about 150 mg. In some embodiments, the α4β7 binding antibody is administered at a dose of about 250 mg to about 750 mg. In some embodiments, the α4β7 binding antibody is administered at a dose of about 300 mg to about 700 mg. In some embodiments, the α4β7 binding antibody is administered at a dose of about 300 mg to about 600 mg. In some embodiments, the α4β7 binding antibody is administered at a dose of about 700 mg to about 900 mg. In some embodiments, the α4β7 binding antibody is administered at a dose of about 600 mg to about 1200 mg. In some embodiments, the α4β7 binding antibody is administered at a dose of about 300 mg to about 500 mg. In some embodiments, the α4β7 binding antibody is administered at a dose of about 300 mg to about 400 mg. In some embodiments, the α4β7 binding antibody is administered at a dose of about 400 mg to about 700 mg. In some embodiments, the α4β7 binding antibody is administered at a dose of about 400 mg to about 600 mg. In some embodiments, the α4β7 binding antibody is administered at a dose of about 300 mg to about 500 mg. In some embodiments, the α4β7 binding antibody is administered at a dose of about 500 mg to about 700 mg. In some embodiments, the α4β7 binding antibody is administered at a dose of about 500 mg to about 600 mg. In some embodiments, the α4β7 binding antibody is administered at a dose of about 600 mg to about 700 mg. In some embodiments, the α4β7 binding antibody is administered at a dose of about 75 mg, about 100 mg, about 125 mg, about 150 mg, about 175 mg, about 200 mg, about 225 mg, about 250 mg, about 275 mg, or about 300 mg, about 350 mg, about 400 mg, about 450 mg, about 500 mg, about 550 mg, about 600 mg, about 650 mg, about 700 mg, about 750 mg, about 800 mg, about 850 mg, about 900 mg or more. In some embodiments, the α4β7 binding antibody is administered at a dose of about 300 mg. Actual dosage levels of the active ingredients in the pharmaceutical compositions of this disclosure may be about 250 mg, 350 mg, 400 mg, 450 mg, 500 mg, 550 mg, 600 mg, 650 mg, 700 mg 750 mg, 800 mg, 850 mg, 900 mg, 950 mg, 1000 mg, 1050 mg, 1100 mg, 1150 mg, or 1200 mg so as to obtain an amount of the active ingredient which is effective to achieve the desired therapeutic response for a particular patient, composition, and mode of administration, without being toxic to the patient.

The specific dose can be a uniform dose for each patient of about 150 mg, of about 200 mg, of about 250 mg, about 300 mg, about 350 mg, about 400 mg, about 450 mg, about 500 mg, about 550 mg, about 600 mg, about 650 mg, about 700 mg, about 750 mg, about 800 mg, about 850 mg, about 900 mg, about 1000 mg, about 1100 mg, about 1200 mg or more of α4β7 binding antibody. Alternatively, a patient's dose can be tailored to the approximate body weight or surface area of the patient. Other factors in determining the appropriate dosage can include the disease or condition to be treated or prevented, the severity of the disease, the route of administration, and the age, sex and medical condition of the patient. Further refinement of the calculations necessary to determine the appropriate dosage for treatment is routinely made by those skilled in the art, especially in light of the dosage information and assays disclosed herein. The dosage can also be determined through the use of known assays for determining dosages used in conjunction with appropriate dose-response data. An individual patient's dosage can be adjusted as the progress of the disease is monitored. Blood levels of the targetable construct or complex in a patient can be measured to see if the dosage needs to be adjusted to reach or maintain an effective concentration. Pharmacogenomics may be used to determine which targetable constructs and/or complexes, and dosages thereof, are most likely to be effective for a given individual (Schmitz et al., *Clinica Chimica Acta* 308:43-53, 2001; Steimer et al., *Clinica Chimica Acta* 308:33-41, 2001).

Kits

Provided herein is a kit for treating a disease in a subject in need thereof comprising: (a) an injectable liquid formulation comprising an α4β7 binding antibody, wherein the α4β7 binding antibody comprises a heavy chain consisting of an amino acid sequence according to SEQ ID NO: 1, and a light chain consisting of an amino acid sequence according to SEQ ID NO: 3, and (b) instructions to administer from about 500 mg to about 1200 mg of the α4β7 binding antibody, instructions to administer from about 120 mg to about 450 mg of the α4β7 binding antibody at least two weeks after the administration of the about 500 mg to about 1200 mg of the α4β7 binding antibody, and instructions to administer from about 120 mg to about 450 mg of the α4β7 binding antibody at least four weeks thereafter. In some embodiments, the α4β7 binding antibody comprises a heavy chain consisting of an amino acid sequence according to SEQ ID NO: 1, and a light chain consisting of an amino acid sequence according to SEQ ID NO: 3.

Provided herein is a kit for treating a disease in a subject in need thereof comprising: (a) an injectable liquid formulation comprising an α4β7 binding antibody, wherein the α4β7 binding antibody comprises a heavy chain consisting of an amino acid sequence according to SEQ ID NO: 1, and a light chain consisting of an amino acid sequence according to SEQ ID NO: 3, and (b) instructions to administer at least 600 mg of the α4β7 binding antibody, at least 300 mg of the α4β7 binding antibody at least two weeks after the administration of the 600 mg of the α4β7 binding antibody, and at least 300 mg of the α4β7 binding antibody at least four weeks thereafter. In some embodiments, the α4β7 binding antibody comprises a heavy chain consisting of an amino acid sequence according to SEQ ID NO: 1, and a light chain consisting of an amino acid sequence according to SEQ ID NO: 3.

Provided herein is a kit for treating a disease in a subject in need thereof comprising: (a) an injectable subcutaneous liquid formulation comprising an α4β7 binding antibody, wherein the α4β7 binding antibody comprises a heavy chain consisting of an amino acid sequence according to SEQ ID NO: 1, and a light chain consisting of an amino acid sequence according to SEQ ID NO: 3, and (b) instructions to administer subcutaneously at least 600 mg of α4β7 binding antibody, at least 300 mg of the α4β7 binding antibody at least two weeks after the administration of the 600 mg of α4β7 binding antibody, and at least 300 mg of α4β7 binding antibody at least four weeks thereafter. In some embodiments, the α4β7 binding antibody comprises a heavy chain consisting of an amino acid sequence according to SEQ ID NO: 1, and a light chain consisting of an amino acid sequence according to SEQ ID NO: 3.

Methods of Preparation

The α4β7 binding antibodies described above can be made using recombinant DNA technology well known to a skilled person in the art. For example, one or more isolated polynucleotides encoding the α4β7 binding antibody can be ligated to other appropriate nucleotide sequences, including, for example, constant region coding sequences, and expression control sequences, to produce conventional gene expression constructs (i.e., expression vectors) encoding the desired α4β7 binding antibodies. Production of defined gene constructs is within routine skill in the art.

Nucleic acids encoding desired α4β7 binding antibodies can be incorporated (ligated) into expression vectors, which can be introduced into host cells through conventional transfection or transformation techniques. Exemplary host cells are *E. coli* cells, Chinese hamster ovary (CHO) cells, human embryonic kidney 293 (HEK 293) cells, HeLa cells, baby hamster kidney (BHK) cells, monkey kidney cells (COS), human hepatocellular carcinoma cells (e.g., Hep G2), and myeloma cells that do not otherwise produce IgG protein. Transformed host cells can be grown under conditions that permit the host cells to express the genes that encode α4β7 binding antibodies. In some embodiments, the nucleic acid comprises a sequence as set forth in SEQ ID NOs: 12-17.

Specific expression and purification conditions will vary depending upon the expression system employed. For example, if a gene is to be expressed in *E. coli*, it is first cloned into an expression vector by positioning the engineered gene downstream from a suitable bacterial promoter, e.g., Trp or Tac, and a prokaryotic signal sequence. The expressed protein may be secreted. The expressed protein may accumulate in refractile or inclusion bodies, which can be harvested after disruption of the cells by French press or sonication. The refractile bodies then are solubilized, and the protein may be refolded and/or cleaved by methods known in the art.

If the engineered gene is to be expressed in eukaryotic host cells, e.g., CHO cells, it is first inserted into an expression vector containing a suitable eukaryotic promoter, a secretion signal, a poly A sequence, and a stop codon. Optionally, the vector or gene construct may contain enhancers and introns. In embodiments involving fusion proteins comprising an α4β7 binding antibody or portion thereof, the expression vector optionally contains sequences encoding all or part of a constant region, enabling an entire, or a part of, a heavy or light chain to be expressed. The gene construct can be introduced into eukaryotic host cells using conventional techniques.

In some embodiments, in order to express an α4β7 binding antibody, an N-terminal signal sequence is included in the protein construct. Exemplary N-terminal signal sequences include signal sequences from interleukin-2, CD-5, IgG kappa light chain, trypsinogen, serum albumin, and prolactin.

After transfection, single clones can be isolated for cell bank generation using methods known in the art, such as limited dilution, ELISA, FACS, microscopy, or Clonepix. Clones can be cultured under conditions suitable for bioreactor scale-up and maintained expression of the α4β7 binding antibodies.

The α4β7 binding antibodies can be isolated and purified using methods known in the art including centrifugation, depth filtration, cell lysis, homogenization, freeze-thawing, affinity purification, gel filtration, ion exchange chromatography, hydrophobic interaction exchange chromatography, and mixed-mode chromatography.

ADDITIONAL EMBODIMENTS

Described herein, in certain embodiments, are subcutaneous dosages form comprising an effective amount of an α4β7 binding antibody comprising: a) a heavy chain comprising an amino acid sequence according to SEQ ID NO: 1 or SEQ ID NO: 2; and b) a light chain comprising an amino acid sequence according to SEQ ID NO: 3. In some embodiments, the effective amount achieves a serum or plasma average concentration of about 35 μg/mL and a trough serum or plasma concentration of at least about 6 μg/mL, e.g., about 10 μg/mL. In some embodiments, the heavy chain comprises an amino acid sequence according to SEQ ID NO: 1 and the light chain comprises an amino acid sequence according to SEQ ID NO: 3. In some embodiments, the heavy chain comprises an amino acid sequence according to SEQ ID NO: 2 and the light chain comprises an amino acid sequence according to SEQ ID NO: 3. In some embodiments, the subcutaneous dosage forms comprise from about 75 mg to about 900 mg or more of the α4β7 binding antibody. In some embodiments, the subcutaneous dosage forms comprise about 75 mg, 100 mg, 150 mg, 200 mg, 350 mg, 400 mg, 450 mg, 500 mg, 550 mg, 600 mg, 650 mg, 700 mg, 750 mg, 800 mg, 850 mg, 900 mg, 1000 mg, 1100 mg, 1200 mg or more of the α4β7 binding antibody. In some embodiments, the subcutaneous dosage forms comprise about 300 mg to about 1200 mg for an induction dose and about 150 mg to 350 mg for a maintenance dose of the α4β7 binding antibody.

Described herein, in certain embodiments, are methods of administering one or more of the dosage described herein. More particularly, the methods of administering one or more of the dosage forms described herein provide for dosing no more frequently than every eight weeks (Q8 dosing), or no more frequently than every twelve weeks (Q12 dosing), or no more frequently than every sixteen weeks (Q16 dosing), and in some embodiments no more frequently than twice per year (Q26 dosing) for maintenance therapy after one to three doses for induction therapy. In some embodiments, the dose is sufficient for annual (Q52) dosing. The methods of administering may further include an induction dose containing 2 or more times the dose of an α4β7 binding antibody of the disclosure. The methods may be by intravenous (IV) or subcutaneous (SC) administration, or both (an IV induction dose or doses and SC maintenance dose); a particular advantage of the disclosure is that is provides for subcutaneous administration of both the induction and maintenance doses.

Described herein, in certain embodiments, are methods of treating an inflammatory bowel disease in a patient in need thereof, the method comprising subcutaneously or intravenously administering to the patient an effective amount of an α4β7 binding antibody comprising: a) a heavy chain comprising an amino acid sequence according to SEQ ID NO: 1 or SEQ ID NO: 2; and b) a light chain comprising an amino acid sequence according to SEQ ID NO: 3. In some embodiments, the inflammatory bowel disease is Crohn's disease or ulcerative colitis. In some embodiments, the inflammatory bowel disease is ulcerative colitis. In some embodiments, the heavy chain comprises an amino acid sequence according to SEQ ID NO: 1 and the light chain comprises an amino acid sequence according to SEQ ID NO: 3. In some embodiments, the heavy chain comprises an amino acid sequence according to SEQ ID NO: 2 and the light chain comprises an amino acid sequence according to SEQ ID NO: 3. In some embodiments, administration of the α4β7 binding antibody is subcutaneous. In some embodiments, administration of the α4β7 binding antibody is intravenous. In some embodiments, the α4β7 binding antibody is administered at a dose of from about 100 mg to about 900 mg. In some embodiments, the α4β7 binding antibody is administered at a dose of from about 100 mg to about 600 mg. In some embodiments, the α4β7 binding antibody is administered at a dose of from about 100 mg to about 300 mg. In some embodiments, the α4β7 binding antibody is administered at a dose of about 300 mg. In some embodiments, the α4β7 binding antibody is administered at a dose of about 350 mg, 400 mg, 450 mg, 500 mg, 550 mg, 600 mg, 650 mg, 700 mg, 750 mg, 800 mg, 850 mg, 900 mg, 1000 mg, 1100 mg, 1200 mg or more.

Described herein, in certain embodiments, are methods of treating a disease or disorder in a patient in need thereof, the method comprising administering to the patient at least once at an interval more than 8 weeks, an effective amount of an α4β7 binding antibody comprising: a) a heavy chain comprising an amino acid sequence according to SEQ ID NO: 1 or SEQ ID NO: 2; and b) a light chain comprising an amino acid sequence according to SEQ ID NO: 3. In some embodiments, the interval is about 12 to about 26 weeks. In some embodiments, the interval is about 12 weeks. In some embodiments, the interval is about 16 weeks. In some embodiments, the interval is about 26 weeks. In some embodiments, the disease or disorder is an inflammatory bowel disease. In some embodiments, the inflammatory bowel disease is Crohn's disease or ulcerative colitis. In some embodiments, the inflammatory bowel disease is ulcerative colitis. In some embodiments, the heavy chain comprises an amino acid sequence according to SEQ ID NO: 1 and the light chain comprises an amino acid sequence according to SEQ ID NO: 3. In some embodiments, the heavy chain comprises an amino acid sequence according to SEQ ID NO: 2 and the light chain comprises an amino acid sequence according to SEQ ID NO: 3. In some embodiments, administration of the α4β7 binding antibody is subcutaneous. In some embodiments, administration of the α4β7 binding antibody is intravenous. In some embodiments, the α4β7 binding antibody is administered at a dose of about 300 mg. In some embodiments, the α4β7 binding antibody is administered at a dose of about 350 mg, 400 mg, 450 mg, 500 mg, 550 mg, 600 mg, 650 mg, 700 mg, 750 mg, 800 mg, 850 mg, 900 mg, 1000 mg, 1100 mg, 1200 mg or more. In some embodiments, the disease or disorder is an inflammatory bowel disease and administration of the α4β7 binding antibody is at an induction dose of about 600 mg, either by intravenous or subcutaneous administration, and a maintenance dose of about 300 mg and is subcutaneous.

Described herein, in certain embodiments, are methods of treating a disease or disorder in a patient in need thereof comprising administering to the patient about 108 mg or about 300 mg of an α4β7 binding antibody every four or six weeks, wherein the α4β7 binding antibody comprises a heavy chain comprising an amino acid sequence according to SEQ ID NO: 4 and a light chain comprising an amino acid sequence according to SEQ ID NO: 5; and wherein no intervening subcutaneous administration of the α4β7 binding antibody occurs during the four or six weeks.

Described herein, in certain embodiments, are methods of treating a disease or disorder in a patient in need thereof comprising administering to the patient about 108 mg or about 300 mg of an α4β7 binding antibody, wherein the α4β7 binding antibody comprises a heavy chain comprising an amino acid sequence according to SEQ ID NO: 1 or SEQ ID NO: 2 and a light chain comprising an amino acid sequence according to SEQ ID NO: 3; and wherein a serum or plasma concentration of the α4β7 binding antibody of at least about 35 μg/mL is achieved in the patient for at least 2 weeks or more upon the administration.

Described herein, in certain embodiments, are methods of treating a disease or disorder in a patient in need thereof comprising subcutaneously administering to the patient an induction dose of about 150 mg to about 1200 mg, for example about 300 mg to about 1000 mg, of an α4β7 binding antibody, wherein the α4β7 binding antibody comprises a heavy chain comprising an amino acid sequence according to SEQ ID NO: 1 or SEQ ID NO: 2 and a light chain comprising an amino acid sequence according to SEQ ID NO: 3; and wherein a serum or plasma concentration of the α4β7 binding antibody of at least about 35 μg/mL is achieved in the patient for at least 2 weeks or more upon the administration and a trough serum or plasma concentration is at least about 6 μg/mL, for example 10 μg/mL.

Described herein, in certain embodiments, are methods of treating a disease or disorder in a patient in need thereof comprising subcutaneously administering to the patient about 108 mg or about 300 mg of an α4β7 binding antibody, wherein the α4β7 binding antibody comprises a heavy chain comprising an amino acid sequence according to SEQ ID NO: 1 or SEQ ID NO: 2 and a light chain comprising an amino acid sequence according to SEQ ID NO: 3; and wherein a maintenance $C_{trough}$ of the α4β7 binding antibody of at least about 6 μg/mL, e.g., about 10 μg/mL, is achieved in the patient upon the administration. In a further embodiment, the dose and administration frequency provide for a $C_{trough}$ of the α4β7 binding antibody of at least about 6 μg/mL, e.g., about 10 μg/mL, in the patient perpetually upon the administration, and the dosing is no more frequent than every 4 weeks, or alternatively every 8 weeks, or alternatively every 12 weeks, or alternatively every 16 weeks, or alternatively every 26 weeks.

In one embodiment, a single or more than one induction dose is administered, followed by maintenance doses. An induction dose can be administered intravenously or subcutaneously. The induction dose may be higher than a maintenance dose or more frequent than a maintenance dose, e.g., in case potentially by a factor of 2. Aspects of the disclosure contemplate one, two, three, or more induction doses. In one example, the induction doses are 600 mg/mL at week 0 and 300 mg/mL at week 2, with maintenance doses of 300 mg/mL every 12 weeks after the second induction dose.

Aspects of the disclosure relate to isolated nucleic acids, expression vector comprising the nucleic acid sequences or recombinant host cell comprising the nucleic acid sequences encoding the heavy chain and/or light chain of the α4β7 binding antibodies described herein. In some embodiments, the nucleic acid sequence encodes SEQ ID NO: 1. In some embodiments, the nucleic acid sequence encodes SEQ ID NO: 3.

Aspects of the disclosure relate to an α4β7 binding antibody comprising a heavy chain consisting of an amino acid sequence according to SEQ ID NO: 1; and a light chain comprising an amino acid sequence according to SEQ ID NO: 3. In some embodiments, the α4β7 binding antibody comprises a heavy chain consisting of an amino acid sequence according to SEQ ID NO: 1; and a light chain consisting of an amino acid sequence according to SEQ ID NO: 3.

Aspects of the disclosure relate to an α4β7 binding antibody comprising a heavy chain and a light chain, wherein the heavy chain consists of an amino acid sequence according to SEQ ID NO: 1. In some embodiments, the light chain consists of an amino acid sequence according to SEQ ID NO: 3.

According to aspects of the disclosure, the α4β7 binding antibody has an increased half-life as compared to an α4β7 binding antibody comprising a heavy chain sequence consisting of SEQ ID NO: 4. In some embodiments, the α4β7 binding antibody has a half-life of from 42 days to 56 days or more in humans.

Aspects of the disclosure relate to a pharmaceutical composition comprising an α4β7 binding antibody and a pharmaceutically acceptable carrier, the α4β7 binding antibody comprising a heavy chain consisting of an amino acid sequence according to SEQ ID NO: 1; and a light chain comprising an amino acid sequence according to SEQ ID NO: 3. In some embodiments, pharmaceutical composition comprises an α4β7 binding antibody and a pharmaceutically acceptable carrier, the α4β7 binding antibody comprising a heavy chain consisting of an amino acid sequence according to SEQ ID NO: 1; and a light chain consisting of an amino acid sequence according to SEQ ID NO: 3. In some embodiments, the pharmaceutical composition is citrate free.

Aspects of the disclosure relate to a subcutaneous dosage form comprising at least about 150 mg of an α4β7 binding antibody comprising a heavy chain consisting of an amino acid sequence according to SEQ ID NO: 1; and a light chain comprising an amino acid sequence according to SEQ ID NO: 3. In some embodiments, the subcutaneous dosage form comprises at least about 150 mg of an α4β7 binding antibody comprising a heavy chain consisting of an amino acid sequence according to SEQ ID NO: 1; and a light chain consisting of an amino acid sequence according to SEQ ID NO: 3. In some embodiments, the dosage form is citrate free. In some embodiments, the subcutaneous dosage comprises from about 150 mg to about 900 mg of the α4β7 binding antibody.

Methods for treating inflammatory bowel disease in a subject in need thereof are provided. In some embodiments, the method comprises administering subcutaneously to the subject one or more of the dosage forms of aspects the disclosure. In some embodiments, the inflammatory bowel disease is Crohn's disease or ulcerative colitis. In some embodiments, the inflammatory bowel disease is ulcerative colitis.

In some embodiments, a method of treating an inflammatory bowel disease in a subject in need thereof comprises administering subcutaneously to the subject an effective amount of an α4β7 binding antibody comprising a heavy chain and a light chain, wherein the heavy chain consists of an amino acid sequence according to SEQ ID NO: 1; and the light chain comprises the variable region of SEQ ID NO: 3.

In some embodiments, a method for treating inflammatory bowel disease in a subject in need thereof, the method comprising administering subcutaneously to the subject an effective amount of an α4β7 binding antibody comprising a heavy chain and a light chain, wherein the heavy chain consists of an amino acid sequence according to SEQ ID NO: 1; and the light chain consists of the variable region of SEQ ID NO: 3.

In some embodiments, the α4β7 binding antibody is administered at a dose of from about 150 mg to about 900 mg. In some embodiments, the method comprises administering to the subject the effective amount of an α4β7 binding antibody at an interval of more than 8 weeks, for example about 12 to about 26 weeks, about 12 weeks, about 16 weeks, about 26 weeks.

In some embodiments, the inflammatory bowel disease is Crohn's disease or ulcerative colitis. In some embodiments, the inflammatory bowel disease is ulcerative colitis.

In some embodiments, an average serum or plasma or serum concentration of the α4β7 binding antibody of at least about 35 μg/mL is achieved in the subject during an induction period.

In some embodiments, a maintenance $C_{trough}$ of the α4β7 binding antibody of at least about 6 μg/mL is achieved in the subject.

Aspects of the disclosure relate to a method for treating inflammatory bowel disease in a subject in need thereof, the method comprising (a) administering subcutaneously to the subject one or more induction dose comprising an effective amount of an α4β7 binding antibody, wherein the α4β7 binding antibody comprises a heavy chain comprising a heavy chain and a light chain, wherein the heavy chain consists of an amino acid sequence according to SEQ ID NO: 1; and the light chain consists of the variable region of SEQ ID NO: 3; (b) administering subcutaneously to the subject one or more maintenance dose comprising an effective amount of the α4β7 binding antibody.

In some embodiments, the one or more maintenance dose of the α4β7 binding antibody is administered at an interval of more than 8 weeks.

In some embodiments, the induction dose comprises an amount to the α4β7 binding antibody about 2 or more times higher than the maintenance dose.

In some embodiments, the induction dose comprises from about 400 mg to about 600 mg of the α4β7 binding antibody and wherein the maintenance dose of from about 150 to about 300 mg of the α4β7 binding antibody. In some embodiments, the induction dose comprises about 600 mg of the α4β7 binding antibody and wherein the maintenance dose of about 300 mg of the α4β7 binding antibody. In some embodiments, the induction dose comprises about 400 mg of the α4β7 binding antibody and wherein the maintenance dose of about 200 mg of the α4β7 binding antibody. In some embodiments, the induction dose comprises about 600 mg of the α4β7 binding antibody and wherein the maintenance dose of about 600 mg of the α4β7 binding antibody.

In some embodiments, the method comprises administering subcutaneously to the subject an induction dose of about 600 mg of the α4β7 binding antibody at week 0 and administering subcutaneously to the subject a maintenance dose of about 600 mg of the α4β7 binding antibody at week 26.

In some embodiments, upon administration of the one or more induction dose an average serum or plasma concentration at least about 35 μg/mL of the α4β7 binding antibody is achieved in the patient during an induction period. In some embodiments, upon administration of the one or more maintenance dose a serum or plasma concentration at least about 6 μg/mL of the α4β7 binding antibody is achieved in the patient in the patient for at least 2 weeks or more.

While the present disclosure provides for subcutaneous administration of the α4β7 binding antibody, it is also possible to administer the α4β7 binding antibody by the intravenous route, i.e., by infusion. It is further contemplated that induction or loading dose or doses may be administered by the subcutaneous (SC) or intravenous (IV) route of administration.

SPECIFIC EMBODIMENTS

Non-limiting specific embodiments are described below, each of which is considered to be within the present disclosure.

Embodiment 1. A multidose regimen comprising liquid formulations for use in treating a disease in a subject in need thereof comprising:
(a) a first injectable liquid formulation comprising a total dosage amount of at least 500 mg of a long acting α4β7 targeting molecule; and
(b) a second injectable liquid formulation comprising a total dosage amount of at least 300 mg of the long acting α4β7 targeting molecule, wherein the long acting α4β7 targeting molecule comprises:
(i) a heavy chain consisting of an amino acid sequence according to SEQ ID NO: 1, and
(ii) a light chain consisting of an amino acid sequence according to SEQ ID NO: 3.

Embodiment 2. The multidose regimen of Embodiment 1, wherein the first injectable liquid formulation comprises a total dosage amount of from about 500 mg to about 1200 mg of the long acting α4β7 targeting molecule.

Embodiment 3. The multidose regimen of Embodiment 1, wherein the first injectable liquid formulation comprises a total dosage amount of about 600 mg of the long acting α4β7 targeting molecule.

Embodiment 4. The multidose regimen of Embodiment 1, wherein the first injectable liquid formulation comprises a total dosage amount of about 1000 mg of the long acting α4β7 targeting molecule.

Embodiment 5. The multidose regimen of anyone of Embodiments 1-4, wherein the second injectable liquid formulation comprises a total dosage amount of from about 300 mg to about 450 mg of the long acting α4β7 targeting molecule.

Embodiment 6. The multidose regimen of anyone of Embodiments 1-4, wherein the second injectable liquid formulation comprises a total dosage amount of about 300 mg of the long acting α4β7 targeting molecule.

Embodiment 7. The multidose regimen of anyone of Embodiments 1-6, wherein the first injectable liquid formulation is for intravenous administration.

Embodiment 8. The multidose regimen of anyone of Embodiments 1-6, wherein the first injectable liquid formulation is for subcutaneous administration.

Embodiment 9. The multidose regimen of Embodiment 8, wherein the first injectable liquid formulation is a single dose or a multidose formulation.

Embodiment 10. The multidose regimen of anyone of Embodiments 1-9, wherein the second injectable liquid formulation is for subcutaneous administration.

Embodiment 11. The multidose regimen of Embodiment 10, wherein the second injectable liquid formulation is suitable for administration as a single injection or multiple injections.

Embodiment 12. The multidose regimen of any one of Embodiments 1-11, wherein the disease is a gastrointestinal inflammatory disease.

Embodiment 13. The multidose regimen of any one of Embodiments 1-11, wherein the disease is an inflammatory bowel disease.

Embodiment 14. The multidose regimen of Embodiment 13, wherein the inflammatory bowel disease is Crohn's disease.

Embodiment 15. The multidose regimen of Embodiment 13, wherein the inflammatory bowel disease is ulcerative colitis.

Embodiment 16. A dosing regimen for use in treating a disease in a subject in need thereof, the dosing regimen comprising:
(a) a first formulation comprising a total dosage amount of at least about 600 mg of a long acting α4β7 targeting molecule for administration to the subject;
(b) a second formulation comprising a total dosage amount of at least about 300 mg of the long acting α4β7 targeting molecule for subcutaneous administration to the subject at least two weeks after the first formulation, and thereafter as a maintenance dose at least eight weeks after administration of the second formulation, wherein the long acting α4β7 targeting molecule comprises:
(i) a heavy chain consisting of an amino acid sequence according to SEQ ID NO: 1, and
(ii) a light chain consisting of an amino acid sequence according to SEQ ID NO: 3.

Embodiment 17. The dosing regimen of Embodiment 16, wherein the first formulation is for subcutaneous administration.

Embodiment 18. The dosing regimen of Embodiment 16, wherein the first formulation is for intravenous administration.

Embodiment 19. The dosing regimen of any one of Embodiments 16-18, wherein the first formulation comprises a total dosage amount of from about 600 mg to about 1200 mg of the long acting α4β7 targeting molecule.

Embodiment 20. The dosing regimen of any one of Embodiments 16-18, wherein the first formulation comprises a total dosage amount of about 600 mg of the long acting α4β7 targeting molecule.

Embodiment 21. The dosing regimen of any one of Embodiments 16-20, wherein the second formulation comprises a total dosage amount of from about 300 mg to about 450 mg of the long acting α4β7 targeting molecule.

Embodiment 22. The dosing regimen of any one of Embodiments 16-20, wherein the second formulation comprises a total dosage amount of about 300 mg of the long acting α4β7 targeting molecule.

Embodiment 23. The dosing regimen of Embodiment 19 or Embodiment 20, wherein the first formulation is suitable for administration as a single injection or multiple injections.

Embodiment 24. The dosing regimen of any one of Embodiments 16-23, wherein the second formulation is a single dose or multidose injectable formulation.

Embodiment 25. The dosing regimen of any one of Embodiments 16-24, wherein the first formulation and the second formulation do not contain citrate.

Embodiment 26. The dosing regimen of Embodiment 25, wherein the first formulation or second formulation or both formulations comprise one or more of:

(a) histidine;
(b) arginine or a salt thereof;
(c) ethylenediaminetetraacetic acid (EDTA); and
(d) polysorbate 80.

Embodiment 27. The dosing regimen of any one of Embodiments 16-26, wherein the disease is a gastrointestinal inflammatory disease.

Embodiment 28. The dosing regimen of any one of Embodiments 16-26, wherein the disease is an inflammatory bowel disease.

Embodiment 29. The dosing regimen of Embodiment 28, wherein the inflammatory bowel disease is Crohn's disease.

Embodiment 30. The dosing regimen of Embodiment 28, wherein the inflammatory bowel disease is ulcerative colitis.

Embodiment 31. An injectable dosage form of an α4β7 binding antibody comprising:
a) a heavy chain consisting of an amino acid sequence according to SEQ ID NO: 1; and
a) a light chain consisting of an amino acid sequence according to SEQ ID NO, wherein the α4β7 binding antibody has an average serum half-life greater than 6 days in cynomolgus monkeys.

Embodiment 32. The injectable dosage form of Embodiment 31, wherein the average serum half-life is about 17 days or greater in cynomolgus monkeys.

Embodiment 33. The injectable dosage form of Embodiments 31 or 32 comprising at least 100 mg/ml of the long acting α4β7 targeting molecule.

Embodiment 34. The injectable dosage form of Embodiments 31 or 32 comprising at least 180 mg/ml of the α4β7 binding antibody.

Embodiment 35. The injectable dosage form of Embodiments 31 or 32 comprising at least 150 mg/ml of the long acting α4β7 targeting molecule.

Embodiment 36. The injectable dosage form of Embodiment 31 or Embodiment 32 comprising at least 200 mg/ml of the long acting α4β7 targeting molecule.

Embodiment 37. The injectable dosage form of any one of Embodiments 31-32, comprising from about 600 mg to about 1200 mg of the long acting α4β7 targeting molecule.

Embodiment 38. The injectable dosage form of any one of Embodiments 31-32, comprising about 600 mg of the long acting α4β7 targeting molecule.

Embodiment 39. The injectable dosage form of any one of Embodiments 31-32, comprising about 1000 mg of the long acting α4β7 targeting molecule.

Embodiment 40. The injectable dosage form of any one of Embodiments 31-39, wherein the injectable dosage form is an injectable liquid formulation.

Embodiment 41. The injectable dosage form of Embodiment 40, wherein the injectable liquid formulation does not comprise citrate.

Embodiment 42. The injectable dosage form of Embodiment 41, wherein the injectable liquid formulation comprises one or more of:
(a) histidine;
(b) arginine or a salt thereof;
(c) ethylenediaminetetraacetic acid (EDTA); and
(d) polysorbate 80.

Embodiment 43. The injectable liquid formulation of any one of Embodiments 1-30 or the Embodiments 40-42, wherein the injectable liquid formulation is a pharmaceutical composition.

Embodiment 44. A method of treating a disease in a patient in need thereof, the method comprising: administering to a subject in need thereof (a) an effective amount of an induction dose of a long acting α4β7 targeting molecule, and (b) an effective amount of one or more maintenance doses of the long acting α4β7 targeting molecule, wherein the one or more maintenance doses are administered subcutaneously at least eight weeks apart, wherein the long acting α4β7 targeting molecule comprises:
(i) a heavy chain consisting of an amino acid sequence according to SEQ ID NO: 1 or SEQ ID NO: 2; and (ii) a light chain consisting of an amino acid sequence according to SEQ ID NO: 3.

Embodiment 45. The method of Embodiment 44, wherein the disease is a gastrointestinal inflammatory disease.

Embodiment 46. The method of Embodiment 44, wherein the disease is an inflammatory bowel disease.

Embodiment 47. The method of Embodiment 45, wherein the inflammatory bowel disease is Crohn's disease.

Embodiment 48. The method of Embodiment 45, wherein the inflammatory bowel disease is ulcerative colitis.

Embodiment 49. The method of any one of Embodiments 44-48, wherein the effective amount of each of the one or more maintenance doses of the long acting α4β7 targeting molecule is at least about 300 mg.

Embodiment 50. The method of any one of Embodiments 44-48, wherein the effective amount of each of the one or more maintenance doses of the long acting α4β7 targeting molecule is from about 300 mg to about 450 mg.

Embodiment 51. The method of any one of Embodiments 44-48, wherein the effective amount of the induction dose of the long acting α4β7 targeting molecule is about 600 mg.

Embodiment 52. The method of any one of Embodiments 44-48, wherein the effective amount of the induction dose of the long acting α4β7 targeting molecule is about 1000 mg.

Embodiment 53. The method of any one of Embodiments 44-48, wherein the effective amount of the induction dose of the long acting α4β7 targeting molecule is from 600 mg to about 1200 mg.

Embodiment 54. The method of any one of Embodiments 51-53 comprising administering the effective amount of the induction dose in a single or multiple injections.

Embodiment 55. The method of any one of Embodiments 44-54, wherein the effective amount of the induction dose of the long acting α4β7 targeting molecule is administered subcutaneously.

Embodiment 56. The method of any one of Embodiments 44-54, wherein the effective amount of the induction dose of the long acting α4β7 targeting molecule is administered intravenously.

Embodiment 57. The method of any one of Embodiments 44-56, wherein the one or more maintenance doses are administered subcutaneously about 12 weeks apart.

Embodiment 58. The method of any one of Embodiments 44-56, wherein the one or more maintenance doses are administered subcutaneously about 26 weeks apart.

Embodiment 59. The method of any one of Embodiments 44-58, wherein the induction dose comprises a dosage amount of the long acting α4β7 targeting molecule that is about 2 or more times higher than a dosage amount of each of the one or more maintenance doses.

Embodiment 60. The method of any one of Embodiments 44-59, wherein:
(a) the long acting α4β7 targeting molecule follows a biphasic decline in serum concentration;
(b) repeated dosing of the long acting α4β7 targeting molecule does not have a significant influence on clearance (CL) and steady-state volume of distribution (Vss);
(c) pharmacokinetic is not impacted by disease state of the patient; or
(d) a combination thereof.

Embodiment 61. A method of achieving $C_{avgW0-W12}$ of from 60 μg/ml to 70 μg/ml or greater for a long acting 4β7 targeting molecule in a subject in need thereof, the method comprising administering to the subject in need thereof a first dosage amount of at least 600 mg of the α4β7 binding antibody, wherein the long acting α4β7 targeting molecule comprises:
(a) a heavy chain consisting of an amino acid sequence according to SEQ ID NO: 1; and
(b) a light chain consisting of an amino acid sequence according to SEQ ID NO: 3.

Embodiment 62. The method of Embodiment 61, wherein the administering results in a $C_{avgW0-W12}$ of about 65 μg/ml.

Embodiment 63. The method of Embodiment 62, wherein the administering comprises administering to the subject in need thereof the first dosage amount of at least 600 mg of the long acting α4β7 targeting molecule and a second dosage amount of at least 300 mg of the long acting α4β7 targeting molecule at least two weeks after administration of the first dosage amount of the long acting α4β7 targeting molecule.

Embodiment 64. The method of Embodiment 63, comprising administering the first dosage amount of at least 600 mg intravenously and the second dosage amount of at least 300 mg of the long acting α4β7 targeting molecule subcutaneously.

Embodiment 65. The method of Embodiment 63, comprising administering the first dosage amount of at least 600 mg subcutaneously and the second dosage amount of at least 300 mg of the long acting α4β7 targeting molecule subcutaneously.

Embodiment 66. The method of any one of Embodiments 61-65 further comprising administering to the subject in need thereof one or more dosage amount of at least 300 mg of the long acting α4β7 targeting molecule at least four weeks after administration of the second dosage amount of the long acting 4β7 targeting molecule.

Embodiment 67. The method of Embodiment 66 comprising administering the one or more dosage amount of the long acting α4β7 targeting molecule subcutaneously.

Embodiment 68. The method of any one of Embodiments 61-67 comprising administering to the subject in need thereof at least 600 mg of the long acting α4β7 targeting molecule every twenty-six weeks after administration of the second dosage amount of the long acting α4β7 targeting molecule.

Embodiment 69. A method of achieving $C_{avgW0-W6}$ of from 65 μg/ml to 75 μg/ml or greater for a long acting α4β7 targeting molecule in a subject in need thereof, the method comprising administering to the subject in need thereof a first dosage amount of at least 600 mg of the long acting α4β7 targeting molecule, wherein the long acting α4β7 targeting molecule comprises:
(a) a heavy chain consisting of an amino acid sequence according to SEQ ID NO: 1; and
(b) a light chain consisting of an amino acid sequence according to SEQ ID NO: 3.

Embodiment 70. The method of Embodiment 69, wherein the administering results in a $C_{avgW0-W6}$ of about 70 μg/ml.

Embodiment 71. The method of Embodiment 69, wherein the administering results in a $C_{avgW0-W6}$ of about 65 μg/ml.

Embodiment 72. The method of any one of Embodiments 69-71, wherein the administering comprises administering to the subject in need thereof a first dosage amount of at least 600 mg of the long acting α4β7 targeting molecule and a second dosage amount of at least 300 mg of long acting α4β7 targeting molecule at least two weeks after administration of the first dosage amount of at least 600 mg of the long acting α4β7 targeting molecule.

Embodiment 73. The method of Embodiment 72, comprising administering the first dosage amount of the long acting α4β7 targeting molecule intravenously and the second dosage amount of the long acting α4β7 targeting molecule subcutaneously.

Embodiment 74. The method of Embodiment 72, comprising administering the first dosage amount and the second dosage amount of the long acting α4β7 targeting molecule subcutaneously.

Embodiment 75. The method of any one of Embodiments 72-74 further comprising administering to the subject in need thereof one or more additional dosage amount of at least 300 mg of the long acting α4β7 targeting molecule at least four weeks after administration of the second dosage amount of the long acting α4β7 targeting molecule.

Embodiment 76. The method of Embodiment 75 comprising administering the one or more additional dosage amount of the long acting α4β7 targeting molecule subcutaneously.

Embodiment 77. The method of Embodiment 75 or Embodiment 68 further comprising administering to the subject in need thereof at least 600 mg of the long acting α4β7 targeting molecule every twenty-six weeks after administration of second dosage amount of the long acting α4β7 targeting molecule.

Embodiment 78. The method of any one of Embodiments 66-68 or 75-77, wherein the administration of the one or more dosage amount of the long acting α4β7 targeting molecule results in $C_{avg}$ of from 40 μg/ml to 50 μg/ml or greater.

Embodiment 79. The method of any one of Embodiments 66-68 or 75-77, wherein the administration of the one or more dose of the long acting α4β7 targeting molecule results in $C_{avg}$ of about 45 μg/ml.

Embodiment 80. A method of achieving $C_{trough}$ of 35 μg/ml or greater for a long acting α4β7 targeting molecule in a subject in need thereof six weeks following administration of the long acting α4β7 targeting molecule to the patient, the method comprising administering to the patient in need thereof at least 600 mg of the long acting α4β7 targeting molecule, wherein the long acting α4β7 targeting molecule comprises:
(a) a heavy chain consisting of an amino acid sequence according to SEQ ID NO: 1; and
(b) a light chain consisting of an amino acid sequence according to SEQ ID NO: 3.

Embodiment 81. The method of Embodiment 80, wherein the administration of the at least 600 mg of the long acting α4β7 targeting molecule results in a serum $C_{avgW0-W12}$ of at least 60 µg/ml.

Embodiment 82. The method of Embodiment 80, wherein the administration of the at least 600 mg of the long acting α4β7 targeting molecule results in a serum $C_{avgW30-W40}$ of at least 30 µg/ml.

Embodiment 83. The method of Embodiment 80, wherein the at least 600 mg of the long acting α4β7 targeting molecule is administered intravenously.

Embodiment 84. The method of Embodiment 80, wherein the at least 600 mg of the long acting α4β7 targeting molecule is administered subcutaneously.

Embodiment 85. The method of any one of Embodiments 80-84 further comprising administering to the subject in need thereof at least 300 mg of the long acting α4β7 targeting molecule, wherein the administration of the at least 300 mg of the long acting α4β7 targeting molecule results in a steady state $C_{trough}$ of at least 6 µg/ml.

Embodiment 86. The method of any one of Embodiments 80-84, further comprising administering to the subject in need thereof at least 300 mg of the long acting α4β7 targeting molecule results in an average serum concentration of the α4β7 binding antibody above 35 µg/ml for ten weeks following the administration of the at least 300 mg of the long acting α4β7 targeting molecule.

Embodiment 87. The method of any one of Embodiments 85-86 further comprising administering subcutaneously to the subject in need thereof at least 300 mg of long acting α4β7 targeting molecule four weeks after administration of last dosage amount of the long acting α4β7 targeting molecule.

Embodiment 88. The method of any one of Embodiments 85-86 further comprising administering subcutaneously to the patient a maintenance dose of at least 600 mg of the long acting α4β7 targeting molecule every twenty-six weeks after administration of the last dose of the α4β7 binding antibody.

Embodiment 89. A long acting α4β7 targeting molecule comprising:
(a) a heavy chain consisting of an amino acid sequence according to SEQ ID NO: 1, and
(b) a light chain consisting of an amino acid sequence according to SEQ ID NO: 3.

Embodiment 90. An isolated nucleic acid encoding the heavy chain and/or light chain of the long acting α4β7 targeting molecule of Embodiment 89.

Embodiment 91. The isolated nucleic acid of Embodiment 90 encoding SEQ ID NO: 1.

Embodiment 92. The isolated nucleic acid of Embodiment 90 encoding SEQ ID NO: 3.

Embodiment 93. A recombinant host cell comprising the isolated nucleic acid of any one of Embodiments 90-92, or an expression vector comprising the isolated nucleic acid of any one of Embodiments 90-92.

Embodiment 95. A kit for treating a disease in a subject in need thereof comprising:
(a) an injectable liquid formulation comprising a long acting α4β7 targeting molecule, wherein the long acting α4β7 targeting molecule comprises:
(i) a heavy chain consisting of an amino acid sequence according to SEQ ID NO: 1, and
(ii) a light chain consisting of an amino acid sequence according to SEQ ID NO: 3, and
(b) instructions to administer at least 600 mg of the long acting 487 targeting molecule, at least 300 mg of the long acting α4β7 targeting molecule at least two weeks after the administration of the 600 mg of the long acting α4β7 targeting molecule, and at least 300 mg of the long acting α4β7 targeting molecule at least four weeks thereafter.

Embodiment 96. A kit for treating a disease in a subject in need thereof comprising:
(a) an injectable subcutaneous liquid formulation comprising a long acting α4β7 targeting molecule, wherein the long acting α4β7 targeting molecule comprises:
(i) a heavy chain consisting of an amino acid sequence according to SEQ ID NO: 1, and
(ii) a light chain consisting of an amino acid sequence according to SEQ ID NO: 3, and
(b) instructions to administer subcutaneously at least 600 mg of the long acting α4β7 targeting molecule, at least 300 mg of the long acting α4β7 targeting molecule at least two weeks after the administration of the 600 mg of the long acting α4β7 targeting molecule, and at least 300 mg of the long acting α4β7 targeting molecule at least four weeks thereafter.

Embodiment 97. The kit of Embodiment 95 or Embodiment 96, wherein the disease is a gastrointestinal inflammatory disease.

Embodiment 98. The kit of Embodiment 95 or Embodiment 96, wherein the disease is an inflammatory bowel disease, optionally Crohn's disease or ulcerative colitis.

Embodiment 99. The long acting α4β7 targeting molecule of Embodiment 89, the long acting α4β7 targeting molecule of the regimen of any one of Embodiments 1-30, long acting α4β7 targeting molecule of the injectable dosage form of any one of Embodiments 31-42, the long acting α4β7 targeting molecule of the method of any one of Embodiments 44-88, the long acting α4β7 targeting molecule of the kit of any one of Embodiments 95-98, wherein the long acting α4β7 targeting molecule comprises one or more of the following characteristics:
i. an average serum half-life greater than about 6 days in cynomolgus monkeys,
ii. an average serum half-life of about 17 days or greater in cynomolgus monkeys,
iii. a melting temperature TmOnset greater than about 55° C.,
iv. a melting temperature TmOnset greater than 56.2° C.,
v. does not induce T cell activation markers CD25 or CD69,
vi. does not result in release of cytokines at least 6 hours after the administration, wherein the cytokines comprise one or more of IL-6, IL-8, IL-1B, IFNγ, IL-4, IL-17, IL-2, IL-23p70 and TNF,
vii. does not induce complement-dependent cytotoxicity (CDC) in primary human PBMCs and in α4β7-expressing human β-lymphoid cell,
viii. does not induce antibody dependent cellular cytotoxicity (ADCC) in human NK cells,
ix. does not impact suppressive activity of regulatory T cells expressing α4β7 integrin, wherein the suppressive activity is measured by presence of elevated CD71, CD25, Ki67, granzyme B, or OX40,
x. a proportion of G0F from about 55.1% to about 60.4%,
xi. a proportion of G1F from about 16.6% to about 18.8%, xii. a proportion of Man5 from about 7.3% to about 8.8%, Embodiment 100. A subcutaneous dosage form comprising at least about 300 mg of an α4β7 binding antibody comprising:
  a) a heavy chain comprising an amino acid sequence according to SEQ ID NO: 1 or SEQ ID NO: 2; and
  b) a light chain comprising an amino acid sequence according to SEQ ID NO: 3.

Embodiment 101. The dosage form of Embodiment 100, wherein the heavy chain comprises an amino acid sequence according to SEQ ID NO: 1 and the light chain comprises an amino acid sequence according to SEQ ID NO: 3.

Embodiment 102. The dosage form of Embodiment 100, wherein the heavy chain comprises an amino acid sequence according to SEQ ID NO: 2 and the light chain comprises an amino acid sequence according to SEQ ID NO: 3.

Embodiment 103. The dosage form of any one of Embodiments 100-102, comprising about 350 mg, 400 mg, 450 mg, 500 mg, 550 mg, 600 mg, 650 mg, or 700 mg of the α4β7 binding antibody.

Embodiment 104. A method of administering one or more of the dosage forms of any one of Embodiments 100-103.

Embodiment 105. A method of treating an inflammatory bowel disease in a patient in need thereof, the method comprising subcutaneously or intravenously administering to the patient an effective amount of an α4β7 binding antibody comprising:
  a) a heavy chain comprising an amino acid sequence according to SEQ ID NO: 1 or SEQ ID NO: 2; and
  b) a light chain comprising an amino acid sequence according to SEQ ID NO: 3.

Embodiment 106. The method of Embodiment 105, wherein the inflammatory bowel disease is Crohn's disease or ulcerative colitis.

Embodiment 107. The method of Embodiment 105, wherein the inflammatory bowel disease is ulcerative colitis.

Embodiment 108. The method of any one of Embodiments 105-107, wherein the heavy chain comprises an amino acid sequence according to SEQ ID NO: 1 and the light chain comprises an amino acid sequence according to SEQ ID NO: 3.

Embodiment 109. The method of any one of Embodiments 105-108, wherein the heavy chain comprises an amino acid sequence according to SEQ ID NO: 2 and the light chain comprises an amino acid sequence according to SEQ ID NO: 3.

Embodiment 110. The method of any one of claims Embodiments 105-109, wherein administration of the α4β7 binding antibody is subcutaneous.

Embodiment 111. The method of any one of Embodiments 105-110, wherein administration of the α4β7 binding antibody is intravenous.

Embodiment 112. The method of any one of Embodiments 105-111, wherein the α4β7 binding antibody is administered at a dose of about 300 mg.

Embodiment 113. The method of any one of Embodiments 105-112, wherein the α4β7 binding antibody is administered at a dose of about 350 mg, 400 mg, 450 mg, 500 mg, 550 mg, 600 mg, 650 mg, or 700 mg.

Embodiment 114. A method of treating a disease or disorder in a patient in need thereof, the method comprising administering to the patient at least once at an interval more than 8 weeks, an effective amount of an α4β7 binding antibody comprising:
  a) a heavy chain comprising an amino acid sequence according to SEQ ID NO: 1 or SEQ ID NO: 2; and
  b) a light chain comprising an amino acid sequence according to SEQ ID NO: 3.

Embodiment 115. The method of Embodiment 114, wherein the interval is about 12 to about 26 weeks.

Embodiment 116. The method of Embodiment 115, wherein the interval is about 12 weeks.

Embodiment 117. The method of Embodiment 115, wherein the interval is about 16 weeks.

Embodiment 118. The method of Embodiment 115, wherein the interval is about 26 weeks.

Embodiment 119. The method of Embodiment 115, wherein the disease or disorder is an inflammatory bowel disease.

Embodiment 120. The method of Embodiment 119, wherein the inflammatory bowel disease is Crohn's disease or ulcerative colitis.

Embodiment 121. The method of Embodiment 119, wherein the inflammatory bowel disease is ulcerative colitis.

Embodiment 122. The method of any one of Embodiments 115-121, wherein the heavy chain comprises an amino acid sequence according to SEQ ID NO: 1 and the light chain comprises an amino acid sequence according to SEQ ID NO: 3.

Embodiment 123. The method of any one of Embodiments 115-121, wherein the heavy chain comprises an amino acid sequence according to SEQ ID NO: 2 and the light chain comprises an amino acid sequence according to SEQ ID NO: 3.

Embodiment 124. The method of any one of Embodiments 115-123, wherein administration of the α4β7 binding antibody is subcutaneous.

Embodiment 125. The method of any one of Embodiments 115-123, wherein administration of the α4β7 binding antibody is intravenous.

Embodiment 126. The method of any one of Embodiments 115-125, wherein the α4β7 binding antibody is administered at a dose of about 300 mg.

Embodiment 127. The method of any one of Embodiments 115-125, wherein the α4β7 binding antibody is administered at a dose of about 350 mg, 400 mg, 450 mg, 500 mg, 550 mg, 600 mg, 650 mg, or 700 mg.

Embodiment 128. The method of any one of Embodiments 115-127, wherein the disease or disorder is an inflammatory bowel disease and administration of the α4β7 binding antibody is at a dose of about 300 mg and is subcutaneous.

Embodiment 129. A method of treating a disease or disorder in a patient in need thereof comprising subcutaneously administering to the patient about 108 mg or about 300 mg of an α4β7 binding antibody every four or six weeks,
  wherein the α4β7 binding antibody comprises a heavy chain comprising an amino acid sequence according to SEQ ID NO: 4 and a light chain comprising an amino acid sequence according to SEQ ID NO: 5; and
  wherein no intervening subcutaneous administration of the α4β7 binding antibody occurs during the four or six weeks.

Embodiment 130. A method of treating a disease or disorder in a patient in need thereof comprising subcutaneously administering to the patient about 108 mg or about 300 mg of an α4β7 binding antibody,
  wherein the α4β7 binding antibody comprises a heavy chain comprising an amino acid sequence according to SEQ ID NO: 1 or SEQ ID NO: 2 and a light chain comprising an amino acid sequence according to SEQ ID NO: 3; and
  wherein a plasma concentration of the α4β7 binding antibody of at least about 35 μg/mL is achieved in the patient for at least 2 weeks or more upon the administration.

Embodiment 131. A method of treating a disease or disorder in a patient in need thereof comprising subcutaneously administering to the patient about 108 mg or about 300 mg of an α4β7 binding antibody,
  wherein the α4β7 binding antibody comprises a heavy chain comprising an amino acid sequence according to SEQ ID NO: 1 or SEQ ID NO: 2 and a light chain comprising an amino acid sequence according to SEQ ID NO: 3; and
  wherein a $C_{trough}$ of the α4β7 binding antibody of at least about 6 μg/mL is achieved in the patient for at least 2 weeks or more upon the administration.

Embodiment 132. The method of any one of Embodiments 130-131, wherein the disorder is inflammatory bowel disease.

Embodiment 133. The method of any one of Embodiments 130-131, wherein the disorder is Crohn's disease or ulcerative colitis.

Embodiment 134. An isolated nucleic acid, wherein the nucleic acid encodes the heavy chain and/or light chain of the α4β7 binding antibody of any one of Embodiments 100-134.

Embodiment 135. The isolated nucleic acid of Embodiment 134, wherein the nucleic acid sequence encodes SEQ ID NO: 1.

Embodiment 136. The isolated nucleic acid of Embodiment 134, wherein the nucleic acid encodes SEQ ID NO: 3.

Embodiment 137. A recombinant host cell comprising the nucleic acid sequences of any one of Embodiments 135-136 or an expression vector comprising the nucleic acid sequences of any one of Embodiments 135-136.

Embodiment 138. An α4β7 binding antibody comprising:
  a) a heavy chain consisting of an amino acid sequence according to SEQ ID NO: 1; and
  b) a light chain comprising an amino acid sequence according to SEQ ID NO: 3.

Embodiment 139. An α4β7 binding antibody comprising:
  a) a heavy chain consisting of an amino acid sequence according to SEQ ID NO: 1; and
  b) a light chain consisting of an amino acid sequence according to SEQ ID NO: 3.

Embodiment 140. An α4β7 binding antibody comprising a heavy chain and a light chain, wherein the heavy chain consists of an amino acid sequence according to SEQ ID NO: 1.

Embodiment 141. The α4β7 binding antibody of Embodiment 140, wherein the light chain consists of an amino acid sequence according to SEQ ID NO: 3.

Embodiment 142. The α4β7 binding antibody of any one of Embodiments 138-141, wherein the α4β7 binding antibody has an increased half-life as compared to an α4β7 binding antibody comprising a heavy chain sequence consisting of SEQ ID NO: 4.

Embodiment 143. The α4β7 binding antibody of any one of Embodiments 138-142, wherein the α4β7 binding antibody has a half-life of from 42 days to 56 days or more in humans.

Embodiment 144. A pharmaceutical composition comprising an α4β7 binding antibody and a pharmaceutically acceptable carrier, the α4β7 binding antibody comprising:
  a) a heavy chain consisting of an amino acid sequence according to SEQ ID NO: 1; and
  b) a light chain comprising an amino acid sequence according to SEQ ID NO: 3.

Embodiment 145. A pharmaceutical composition comprising an α4β7 binding antibody and a pharmaceutically acceptable carrier, the α4β7 binding antibody comprising:
  a) a heavy chain consisting of an amino acid sequence according to SEQ ID NO: 1; and
  b) a light chain consisting of an amino acid sequence according to SEQ ID NO: 3.

Embodiment 146. The pharmaceutical composition of any one of Embodiment 144-145, wherein the composition is citrate free.

Embodiment 147. A subcutaneous dosage form comprising at least about 150 mg of an α4β7 binding antibody comprising:
  a) a heavy chain consisting of an amino acid sequence according to SEQ ID NO: 1; and
  b) a light chain comprising an amino acid sequence according to SEQ ID NO: 3.

Embodiment 148. A subcutaneous dosage form comprising at least about 150 mg of an α4β7 binding antibody comprising:
  a) a heavy chain consisting of an amino acid sequence according to SEQ ID NO: 1; and
  b) a light chain consisting of an amino acid sequence according to SEQ ID NO: 3.

Embodiment 149. The subcutaneous dosage form of Embodiment 147 or Embodiment 148, wherein the dosage form is citrate free.

Embodiment 150. The subcutaneous dosage form of Embodiment 147, Embodiment 148, or Embodiment 149, comprising from about 150 mg to about 900 mg of the α4β7 binding antibody.

Embodiment 151. A method for treating inflammatory bowel disease in a subject in need thereof, the method comprising administering subcutaneously to the subject one or more of the dosage forms of any one of Embodiments 147-150.

Embodiment 152. The method of Embodiment 151, wherein the inflammatory bowel disease is Crohn's disease or ulcerative colitis.

Embodiment 153. The method of Embodiment 151, wherein the inflammatory bowel disease is ulcerative colitis.

Embodiment 154. A method of treating an inflammatory bowel disease in a subject in need thereof, the method comprising administering subcutaneously to the subject an effective amount of an α4β7 binding antibody comprising a heavy chain and a light chain, wherein the heavy chain consists of an amino acid sequence according to SEQ ID NO: 1; and the light chain comprises the variable region of SEQ ID NO: 3.

Embodiment 155. A method for treating inflammatory bowel disease in a subject in need thereof, the method comprising administering subcutaneously to the subject an effective amount of an α4β7 binding antibody comprising a heavy chain and a light chain, wherein the heavy chain consists of an amino acid sequence according to SEQ ID NO: 1; and the light chain consists of the variable region of SEQ ID NO: 3.

Embodiment 156. The method of Embodiment 154 or Embodiment 155, wherein the α4β7 binding antibody is administered at a dose of from about 150 mg to about 900 mg.

Embodiment 157. The method of Embodiment 154 or Embodiment 155, comprising administering to the subject the effective amount of an α4β7 binding antibody at an interval of more than 8 weeks.

Embodiment 158. The method of Embodiment 157, wherein the interval is about 12 to about 26 weeks.

Embodiment 159. The method of Embodiment 157, wherein the interval is about 12 weeks.

Embodiment 160. The method of Embodiment 157, wherein the interval is about 16 weeks.

Embodiment 161. The method of Embodiment 157, wherein the interval is about 26 weeks.

Embodiment 162. The method of Embodiment 157, wherein the inflammatory bowel disease is Crohn's disease or ulcerative colitis.

Embodiment 163. The method of Embodiment 157, wherein the inflammatory bowel disease is ulcerative colitis.

Embodiment 164. The method of Embodiment 155 or Embodiment 156, wherein an average plasma or serum concentration of the α4β7 binding antibody of at least about 35 µg/mL is achieved in the subject during an induction period.

Embodiment 165. The method of Embodiment 154 or Embodiment 155, wherein a maintenance $C_{trough}$ of the α4β7 binding antibody of at least about 6 µg/mL is achieved in the subject upon the administration.

Embodiment 166. A method for treating inflammatory bowel disease in a subject in need thereof, the method comprising (a) administering subcutaneously to the subject one or more induction dose comprising an effective amount of an α4β7 binding antibody, wherein the α4β7 binding antibody comprises a heavy chain comprising a heavy chain and a light chain, wherein the heavy chain consists of an amino acid sequence according to SEQ ID NO: 1; and the light chain consists of the variable region of SEQ ID NO: 3; (b) administering subcutaneously to the subject one or more maintenance dose comprising an effective amount of the α4β7 binding antibody.

Embodiment 167. The method of Embodiment 166, wherein the induction dose comprises an amount to the α4β7 binding antibody about 2 or more times higher than the maintenance dose.

Embodiment 168. The method of Embodiment 166, wherein the induction dose comprises from about 400 mg to about 600 mg of the α4β7 binding antibody and wherein the maintenance dose of from about 150 to about 300 mg of the α4β7 binding antibody.

Embodiment 169. The method of Embodiment 166, wherein the induction dose comprises about 600 mg of the α4β7 binding antibody and wherein the maintenance dose of about 300 mg of the α4β7 binding antibody.

Embodiment 170. The method of Embodiment 166, wherein the induction dose comprises about 400 mg of the α4β7 binding antibody and wherein the maintenance dose of about 200 mg of the α4β7 binding antibody.

Embodiment 171. The method of Embodiment 166, wherein the induction dose comprises about 600 mg of the α4β7 binding antibody and wherein the maintenance dose of about 600 mg of the α4β7 binding antibody.

Embodiment 172. The method of any one of Embodiments 166-171, wherein upon administration of the one or more induction dose an average serum or plasma concentration at least about 35 µg/mL of the α4β7 binding antibody is achieved in the patient during an induction period.

Embodiment 173. The method of any one of Embodiments 166-171, wherein upon administration of the one or more maintenance dose a serum or plasma concentration at least about 6 µg/mL of the α4β7 binding antibody is achieved in the patient in the patient for at least 2 weeks or more.

Embodiment 174. The method of any one of Embodiments 166-171, wherein the one or more maintenance dose of the α4β7 binding antibody is administered at an interval of more than 8 weeks.

EXAMPLES

The disclosure now being generally described, will be more readily understood by reference to the following examples, which are included merely for purposes of illustration of certain aspects and embodiments of the present disclosure, and is not intended to limit the disclosure.

Example 1: α4β7 Binding Antibodies Efficacy

This Example describes the efficacy of the α4β7 binding antibodies described herein.

Figure 1B:
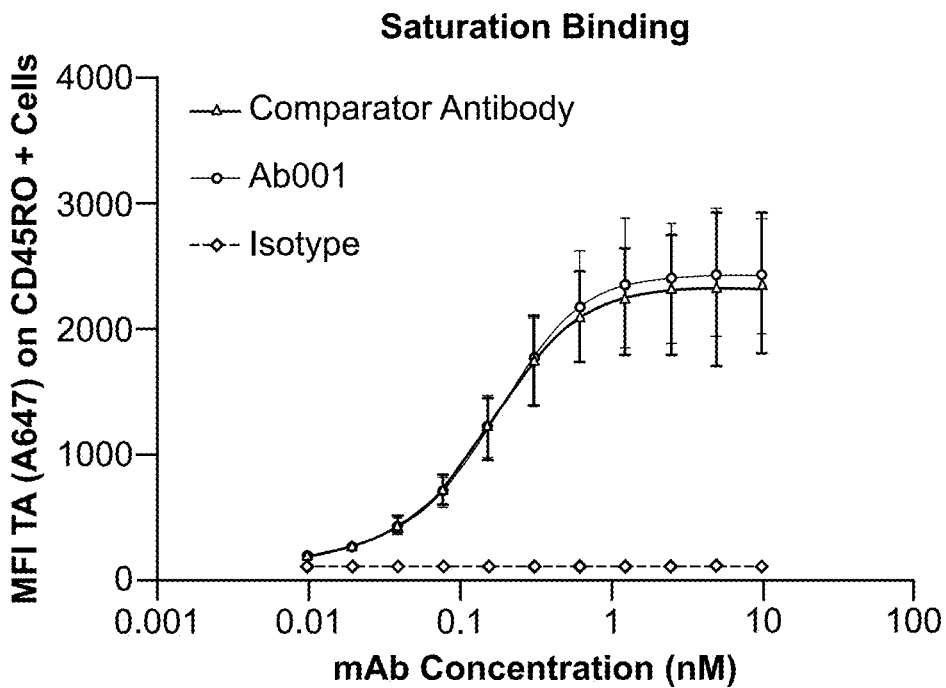
FIG. 1B and FIG. 1C depict binding of the α4β7 binding antibody Ab001 and a comparator antibody to α4β7-expressing peripheral blood mononuclear cells.
Figure 1C:
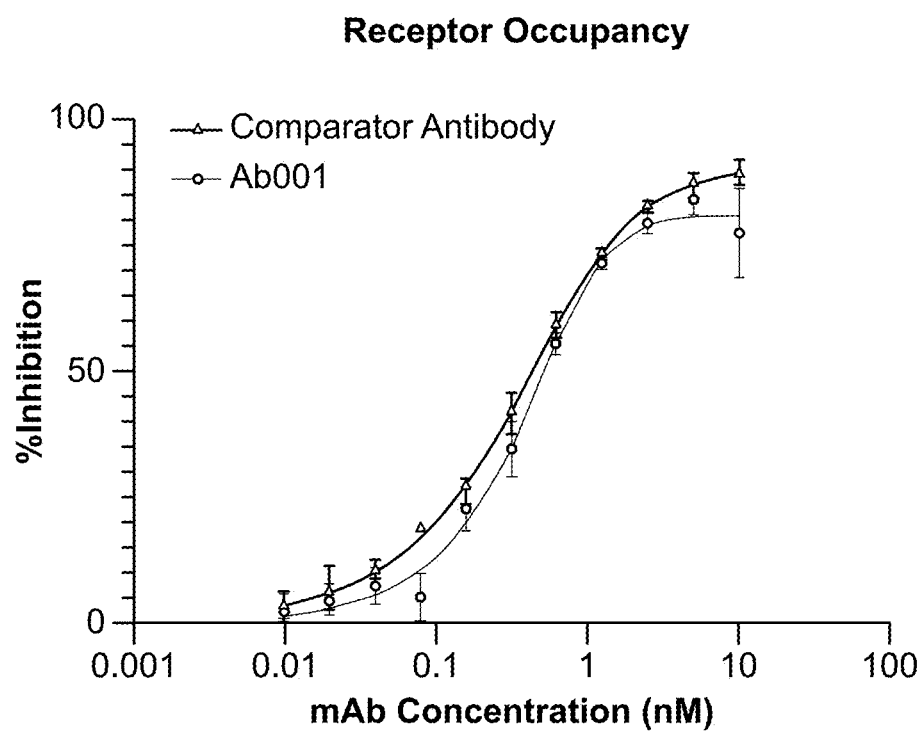

PBMCs contain cell types that express α4β7 integrin and CD4+ helper T cells are associated with inflammatory bowel diseases. The ability of α4β7 binding antibody described herein (i.e., α4β7 binding antibody Ab001 comprising a heavy chain comprising a sequence according to SEQ ID NO: 1 and a light chain comprising a sequence according to SEQ ID NO: 3) to bind PBMCs was analyzed. Cell binding to PBMCs isolated from three human donors was determined by staining with either comparator antibody (solid line; filled shapes) or Ab001 (dashed line; open shapes) at various increasing concentrations (FIG. 1A and FIG. 1B). FIG. 1C shows the receptor occupancy on α4β7-expressing peripheral blood mononuclear cells. The comparator antibody described in this Example and the remaining Examples comprises a heavy chain comprising a sequence according to SEQ ID NO: 4 and a light chain comprising a sequence according to SEQ ID NO: 5. A basic immunophenotyping T-cell panel indicated that both the comparator antibody and α4β7 binding antibody exhibit binding on the memory T-helper CD3+CD4+CD45RO+ population. $EC_{50}$ values for the comparator antibody and α4β7 binding antibody is seen in (Table 2A) and $EC_{50}$ values for both antibodies correspond well with what has previously been reported for binding to the same population: $EC_{50}$~0.3 nM.

TABLE 2A

EC50 data for binding to PBMCs

|  | Comparator Antibody $EC_{50}$ (nM) | α4β7 binding antibody (Ab001) $EC_{50}$ (nM) |
|---|---|---|
| Donor 1 | 0.22 | 0.21 |
| Donor 2 | 0.27 | 0.30 |
| Donor 3 | 0.24 | 0.22 |

The $IC_{50}$ values for competitive inhibition were determined by titrating unlabeled Ab001 into samples equilibrated with $EC_{50}$ concentrations of fluorescently labeled Ab001. Ab001 and Comparator Antibody Receptor Occupancy ($IC_{50}$) on CD4+, CD20+, and CD45RO+ Cells from Human and Monkey Donors are shown in Table 2B.

TABLE 2B

Receptor Occupancy by Cell Type

Figure 2A:
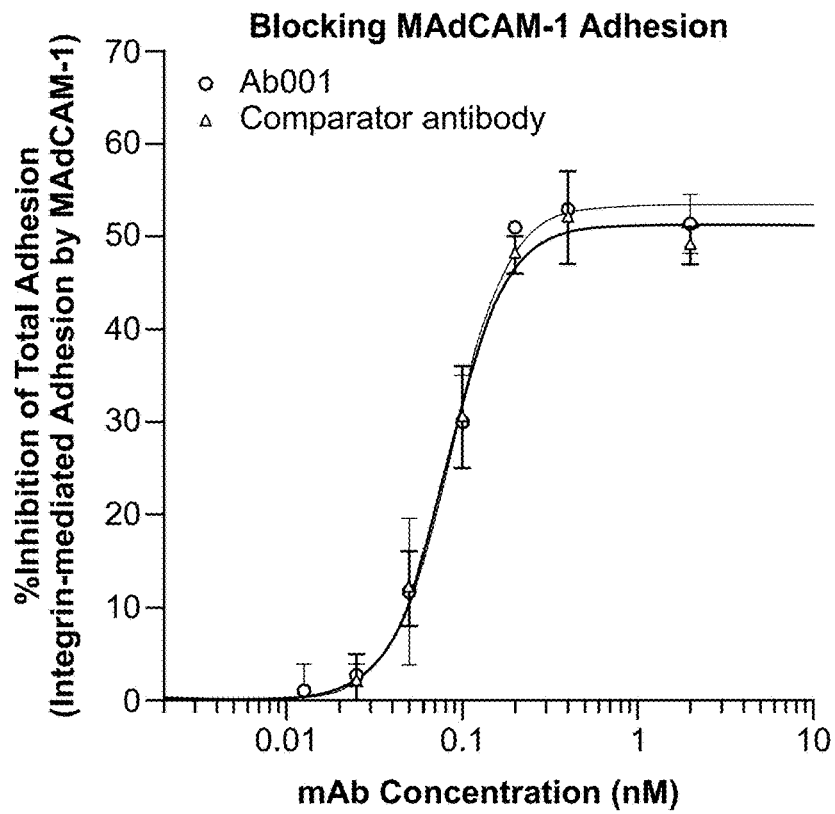
FIGS. 2A and 2B depict blocking of MAdCAM-1 and VCAM-1 adhesion by an α4β7 binding antibody Ab001 (i.e., α4β7 binding antibody comprising a heavy chain consisting of a sequence according to SEQ ID NO: 1 and a light chain consisting of a sequence according to SEQ ID NO: 3).
Figure 2B:
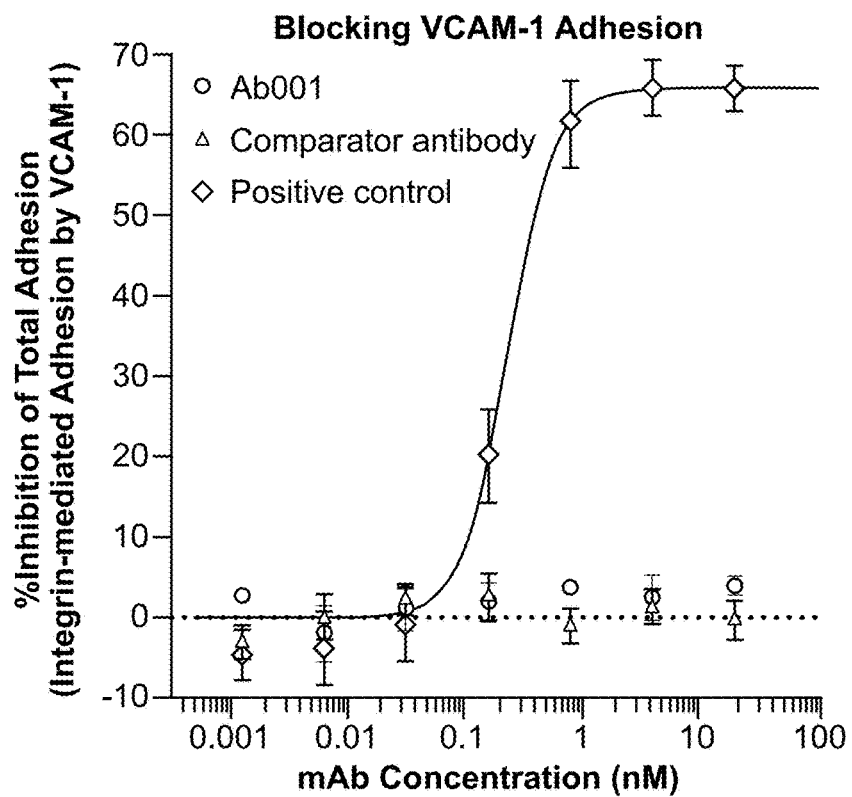

| Cell Type | Attribute | Human whole blood | | Human PBMCs | | Monkey PBMCs | |
|---|---|---|---|---|---|---|---|
| | | Ab001 | Comparator Antibody | Ab001 | Comparator Antibody | Ab001 | Comparator Antibody |
| CD4 + $T_h$ Cells | IC 50 (nM, range, n = 3 donors) | 0.41-0.64 | 0.40-0.46 | 0.37-0.39 | 0.35-0.40 | 0.49-0.54 | 0.48-0.60 |
| | Maximum inhibition (%, range, n = 3 donors) | 85-97% | 86-97% | 68-84% | 88-91% | 86-88% | 88-93% |
| CD20 + B Cells | $IC_{50}$ (nM, range, n = 3 donors) | 0.44-0.60 | 0.40-0.49 | 0.35-0.38 | 0.36-0.38 | 0.46-0.50 | 0.42-0.66 |
| | Maximum inhibition (%, range, n = 3 donors) | 85-98% | 83-98% | 68-83% | 90-91% | 76-83% | 80-85% |
| CD45RO + Memory T Cells | $IC_{50}$ (nM, range, n = 1 donor) | 0.41-0.64 | 0.40-0.47 | 0.37-0.40 | 0.31-0.44 | 0.53 | 0.58 |
| | Maximum inhibition (%, range, n = 1 donor) | 86-97% | 87-97% | 67-84% | 84-89% | 89% | 93% |
| All cell types | $IC_{50}$ (nM, mean, n = 7) | 0.53 ± 0.08 | 0.44 ± 0.03 | 0.38 ± 0.02 | 0.38 ± 0.03 | 0.50 ± 0.03 | 0.56 ± 0.08 |
| All cell types | Maximum inhibition (%, mean, n = 7) | 90 ± 5% | 90 ± 5% | 81 ± 3% | 90 ± 1% | 84% ± 4% | 87% ± 5% |

α4β7 integrin is a ligand for mucosal addressin cell adhesion molecule 1 (MAdCAM1) and the interaction of these two molecules leads to gut homing of lymphocytes. Blocking this interaction is a therapeutic target for inflammatory bowel diseases including ulcerative colitis and Crohn's disease. α4β7-mediated adhesion of MAdCAM-1 was tracked in cells treated with various increasing concentrations of α4β7 binding antibody Ab001 or comparator antibody to determine percent inhibition of total adhesion of MAdCAM-1 (FIG. 2A). α4β7 binding antibody Ab001 preformed as effectively as the comparator antibody. α4β1 integrin is a related integrin that is a ligand for VCAM-1 that mediates homing of lymphocytes to vascular endothelium. Importantly, in a similar assay tracking VCAM-1 adhesion the α4β7 binding antibody Ab001 did not block VCAM-1 adhesion. As a positive control an antibody that can target α4β1 integrin did inhibit VCAM-1 adhesion (FIG. 2B). α4β7 binding antibody Ab001 was evaluated in human whole blood assays designed to detect effects on cytokine release and T cell activation. In whole blood assays from three human donors, α4β7 binding antibody Ab001 did not induce T cell activation markers CD25 or CD69 as measured by FACS. Furthermore, no release of cytokines (Luminex assays of IL-6, IL-8, IL-1B, IFNγ, IL-4, IL-17, IL-2, IL-23p70 and TNF) was observed at time points taken 6 hours or 24 hours after addition of α4β7 binding antibody Ab001 (400 µg/mL) to the samples. In contrast, the above markers were induced when human whole blood was incubated with lipopolysaccharide (LPS) or phytohemagglutinin (PHA), known mitogens that target T and B cells and activate cytokine release.

The ability of α4β7 binding antibody Ab001 to induce CDC was evaluated in primary human PBMCs and in the α4β7-expressing human B-lymphoid cell line RPMI-8866. PBMCs were incubated (4 hr) with (i) α4β7 binding antibody Ab001, (ii) comparator antibody, (iii) OKT3 (known to induce CDC in T cells), and (iv) an IgG1 isotype negative control antibody at a series of concentrations up to 10 µg/mL. RPMI-8866 cells were incubated (4 hr) with (i) α4β7 binding antibody Ab001, (ii) comparator antibody, (iii) rituximab (known to induce CDC in B cells), and (iv) the same IgG1 isotype negative control antibody as in the PBMC cell assay. In both the PBMC and RPMI-8866 assays, cell viability was measured and complement-induced specific death (%) was reported versus test antibody concentration for all experimental conditions. Ab001, like the comparator antibody, did not induce CDC in either PBMCs or RPMI-8866 cells.

α4β7 binding antibody Ab001 was evaluated for its ability to induce ADCC in human NK cells. Primary human NK cells were isolated and used as effector cells along with an α4β7 expressing human B-lymphoid cell line (RPMI-8866) used as the target cell population. Effector NK cells and RPMI-8866 cells together were incubated (3 hr) with (i) α4β7 binding antibody Ab001, (ii) comparator antibody, (iii) rituximab (known to induce ADCC), and (iv) an IgG1 isotype negative control antibody at a series of concentrations from 300 μg/mL to 10 μg/mL. Cell viability was measured and ADCC-induced specific death (%) was reported versus test antibody concentration for all experimental conditions. Neither α4β7 binding antibody Ab001 nor the comparator antibody induced NK cell-mediated ADCC in RPMI-8866 cells. α4β7 binding antibody Ab001 showed similar cell death ranges as comparator antibody.

The ability of α4β7 binding antibody Ab001 to impact the normal activity of regulatory T cells (Treg) was tested using human PBMCs. Regulatory T cells expressing α4β7 integrin were isolated by FACS and co-cultured with CD8+ T responder cells in the presence or absence of test antibodies and a T cell stimulation reagent. Markers of T cell activation (CD71, CD25, Ki67, granzyme B, or OX40) were measured. α4β7 binding antibody Ab001 did not impact Treg suppressive activity at concentrations more than 10-fold above its known EC50. As Treg cell numbers increased from a ratio of 0:16 (None) to 8:16 Treg: CD8+, stimulated CD8+ cells were suppressed based on one marker of T cell activation (CD25+). Similar results were observed when treated with α4β7 binding antibody Ab001, media alone, the IgG1 isotype negative control, and the comparator antibody. Similar results were also seen for Treg suppressive activity when measured by the markers CD71, Ki67, granzyme B, and OX40.

The ability of α4β7 binding antibody Ab001 to bind and induce internalization of α4β7 integrin was measured using CD4+ memory T Cells. Human memory CD4+ T cells were exposed to fluorescently labeled test antibodies, including α4β7 binding antibody Ab001-A647 and the comparator antibody, at concentrations ranging from 0 nM to 100 nM, then incubated (24 hr) at temperatures that either allow (37° C.) or restrict (4° C.) receptor internalization. Cells were then washed with either buffer (FACS), or a gentle acid (0.5 M NaCl+0.2 M acetic acid), the latter to remove membrane-bound antibodies and associated fluorescence signal. Cells incubated with A647-labeled Ab001 under internalization conditions (37° C.) retained greater fluorescence after acid wash than cells stained and incubated under conditions when internalization was restricted (4° C.). This indicated that α4β7 integrin was internalized after binding to fluorescently comparator antibody.

The ability for functional α4β7 to be rapidly expressed after antibody-induced internalization was determined by incubating α4β7 binding antibody Ab001 or the comparator antibody (24 hr at 37° C.) at concentrations of 0 nM (control), 0.11 nM, 0.33 nM, or 1.0 nM with human PBMCs. After incubation, to allow internalization, cells were washed twice with PBS to remove unbound, unlabeled test antibodies. The cells were then resuspended in suitable media (RPMI 1640+10% fetal bovine serum), incubated for 96 hr with fluorescently-labeled α4β7 binding antibody Ab001 or comparator antibody and monitored for fluorescence at 0 hr, 24 hr, and 96 hr. The results were similar for both α4β7 binding antibody Ab001 and comparator antibody, demonstrating that functional α4β7 could be re-expressed on lymphocytes within 24 to 96 hours of antibody-induced internalization.

Figure 3:
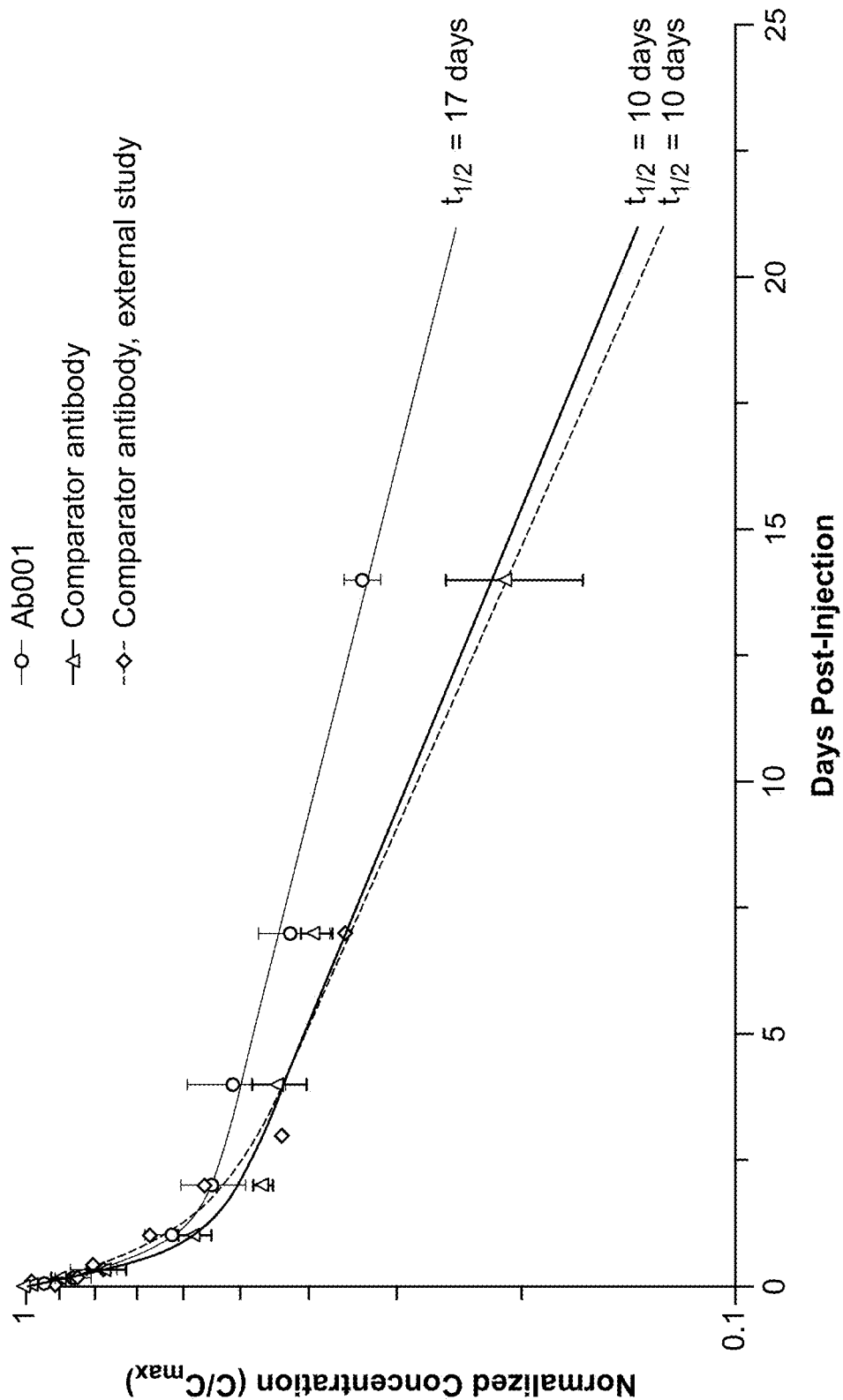
FIG. 3 depicts the half-life of an α4β7 binding antibody Ab001 in non-human primates (NHPs). NHPs were intravenously injected with either an α4β7 binding antibody or comparator antibody and monitored out to 21 days post-injection. Normalized concentration of α4β7 binding antibody or comparator antibody was calculated at each timepoint and used to determine the B-elimination half-life. Also plotted is data from an external study of the comparator antibody (dashed line) illustrating comparable results.

Using non-human primates (NHPs) the half-life of Ab001 was studied. NHPs were intravenously injected with comparator antibody or Ab001 and normalized concentration of each protein was calculated at multiple timepoints out to 21 days post injection (FIG. 3). Data from an external study using the comparator antibody was also plotted ($t_{1/2} \approx 10$ days). The β-elimination half-life of α4β7 binding antibody Ab001 ($t_{1/2} \approx 17$ days) was 70% longer than observed for the comparator antibody. YTE modification used for the α4β7 binding antibody Ab001 described herein typically increases mAb half-life by 2-4× versus wild-type in both NHP and human. Human mAb half-life is at least ~2×NHP half-life. Therefore the human half-life based on initial allometric scaling based on these data is projected to be 43-56 days.

In additional experiments, half-life extension was evaluated via pharmacokinetic analysis in Tg276 transgenic mice (hemizygous for human FcRn) following a single intravenous bolus dose of the α4β7 binding antibody Ab001 (10 mg/kg, 5 mg/kg, 1 mg/kg) and in cynomolgus monkeys following a single bolus dose of the α4β7 binding antibody Ab001 (150 mg/kg), given by either intravenous (IV) and subcutaneous (SC) administration. PK simulations in humans were based on allometric scaling of the α4β7 binding antibody Ab001 clearance observed in cynomolgus monkey and conducted in MATLAB.

In Tg276 mice, the half-life of the α4β7 binding antibody Ab001 was 10-11 days across all dose cohorts compared to approximately 3 days for the comparator antibody. In cynomolgus monkeys, the half-life of the α4β7 binding antibody Ab001 was 19-23 days following a single IV or SC infusion, a significant increase over the reported half-life of 10 days for the comparator antibody in cynomolgus monkeys. Based on allometric scaling of the clearance of the α4β7 binding antibody Ab001 observed in this study, predictive simulations of the α4β7 binding antibody Ab001 PK in humans suggested that Q8W-Q12W SC dosing at 300 mg would be able to achieve a $C_{6\text{-}wks,\ induction} \geq 35$ μg/mL and $C_{trough,\ ss} \geq 6$ μg/mL for simulated patients.

Example 2: Subcutaneous Dose Regimens for α4β7 Binding Antibodies

Pharmacokinetic (PK)-pharmacodynamic (PD) modeling and simulation was conducted to determine dose and regimens of subcutaneous doses that maintain certain serum concentrations above a specific level at a given time during the regimen or at steady state. Achieving these thresholds has been demonstrated to be an important metric for patients to achieve clinical remission in ulcerative colitis. Specifically, maintaining a trough concentration $C_{trough} \geq 35$ μg/mL after 6 weeks post-induction is associated with significantly higher rates of remission in ulcerative colitis.

A two compartment linear model with parameters for central volume of distribution (Vc), peripheral volume of distribution (Vp), clearance from the central volume (Cl), first-order absorption rate constant from a subcutaneous depot into the central volume (ka), and subcutaneous bioavailability relative to the intravenous administration was used to identify dosing regimens. Given the expectation of the α4β7 binding antibodies disclosed herein to have a longer serum half-life than normal IgG, the effective human half-life used in these models was 53 days.

In order to achieve higher clinical remission overall, dosing regimens where >95% of patients achieved a minimum concentration of ≥35 μg/mL at 6 weeks (Table 3) or $C_{trough}$ of ≥6 μg/mL at steady state (Table 4) were identified. The model was further refined by adding the effect of covariates including body weight and serum albumin.

To simulate the serum concentrations of the α4β7 binding antibodies over time with specified dosing regimens in a large population of diverse patients, 1000 patients were uniquely assigned a body weight and serum albumin concentration. These two covariates were assigned independently and randomly chosen using a cumulative distribution function (CDF) of body weights and a separate CDF for serum albumin concentration. To derive each CDF, the percentiles for body weight and serum albumin concentration reported in a clinical trial of a comparator antibody were used to fit a generalized extreme value distribution to allow for a variety of probability distribution behaviors that could be expected in a real-world clinical trial. Body weights values were log-transformed while serum albumin concentration values were used directly.

TABLE 3

Minimum induction regimens allowing for >95% of patients to achieve a serum concentration of ≥35 μg/mL at 6 weeks

| Strategy | IV (Dose/Time) | Minimum x Dose (mg) | SC (Dose/Time) | Minimum y Dose (mg) |
|---|---|---|---|---|
| Strategy 1 | x W0 | 550 | None | N/A |
| Strategy 2 | 300 mg W0, x W2 | 200 | None | N/A |
| Strategy 3 | 600 mg W0, x W2 | 0 | None | N/A |
| Strategy 4 | None | N/A | y W0 | 620 |
| Strategy 5 | None | N/A | 300 mg W0, y W2 | 280 |
| Strategy 6 | None | NA | 600 mg W0, y W2 | 100 |
| Strategy 7 | None | N/A | 300 mg W0, y W1, W2, W3 | 150 |

TABLE 4

Minimum maintenance regimens allowing for >90% of patients to achieve a serum $C_{trough}$ of ≥6 μg/mL at steady-state

| Frequency | Route | Dose (mg) |
|---|---|---|
| Every 4 weeks | IV | 40 |
|  | SQ | 45 |
| Every 8 weeks | IV | 110 |
|  | SQ | 120 |
| Every 12 weeks | IV | 220 |
|  | SQ | 275 |
| Every 26 weeks | IV | 1800 |
|  | SQ | 2000 |

Example 3: Dose Responses of α4β7 Binding Antibodies

This Example describes the dose responses of the α4β7 binding antibodies described herein.

Figure 4:
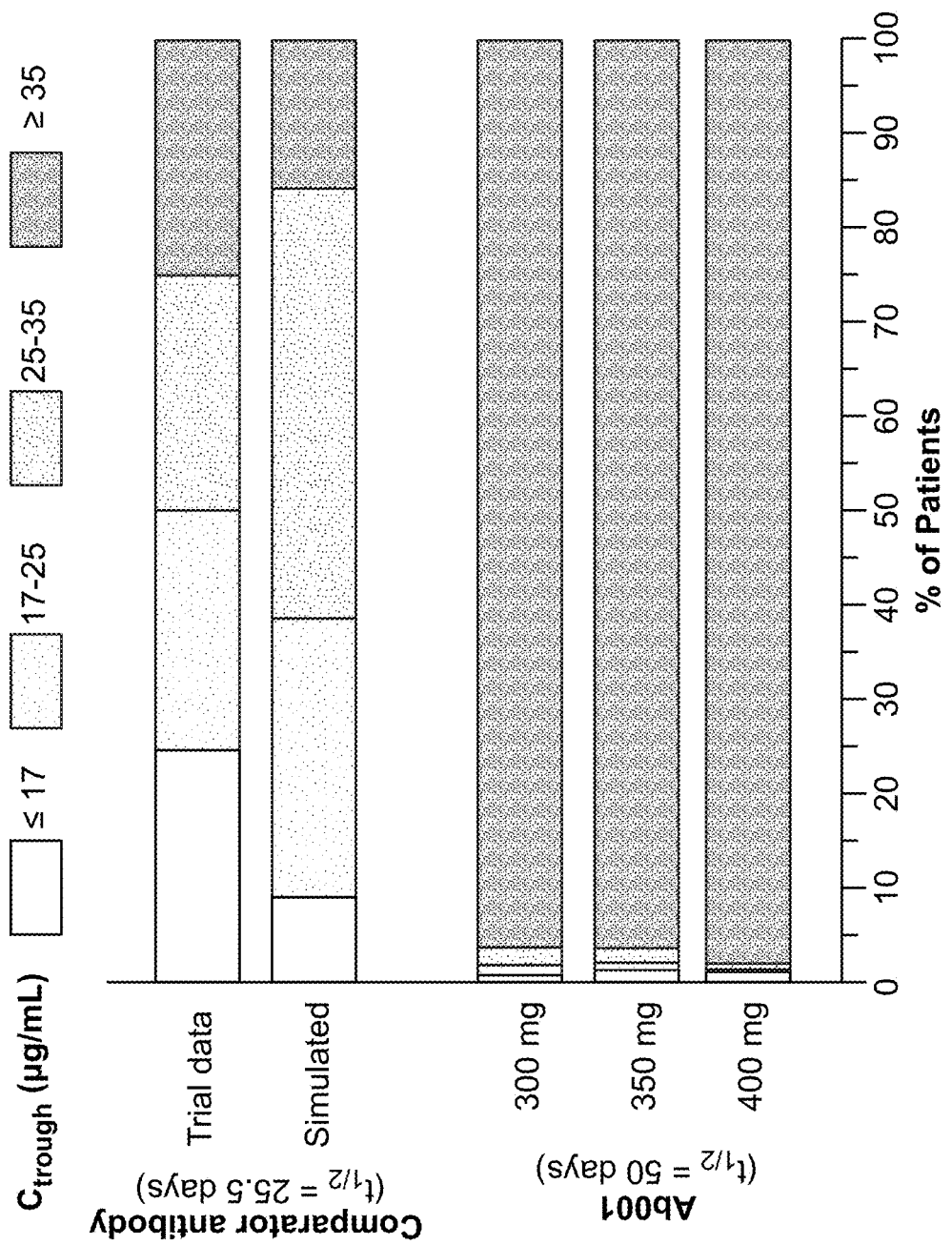
FIG. 4 depicts simulated maintenance of trough concentrations at 6 weeks post-induction by IV associated with higher rates of remission in ulcerative colitis. The percentage of patients with $C_{trough}$ values ≤17, 17-25, 25-35, and ≥35 μg/mL were plotted in a stacked bar chart for patients treated with a comparator antibody during a clinical trial at 6 weeks post-induction. Also shown are the percentage of patients with $C_{trough}$ values from a simulated trial of 1000 patients treated with the comparator antibody, and an α4β7 binding antibody described herein (e.g., Ab001) at doses of 300 mg, 350 mg, and 400 mg.

A simulated trial of 1000 patients was simulated using induction scenarios with an α4β7 binding antibody with YTE modifications such as α4β7 binding antibody Ab001 at intravenous doses of 300 mg, 350 mg, and 400 mg to determine the $C_{trough}$ values at 6 weeks post-induction (FIG. 4). Data generated in a clinical trial of a comparator antibody dosed intravenously at 300 mg is also shown. The comparator antibody was also run through the same simulation. A human half-life of 25.5 days was used for the comparator antibody and a human half-life of 50 days was used for Ab001 in these simulations. At most, 25% of patients dosed with the comparator antibody met the $C_{trough}$≥35 μg/ml threshold at 6 weeks post-induction. In comparison, the vast majority of simulated patients dosed with all concentrations of Ab001 tested maintained a $C_{trough}$≥35 μg/ml.

Figure 5:
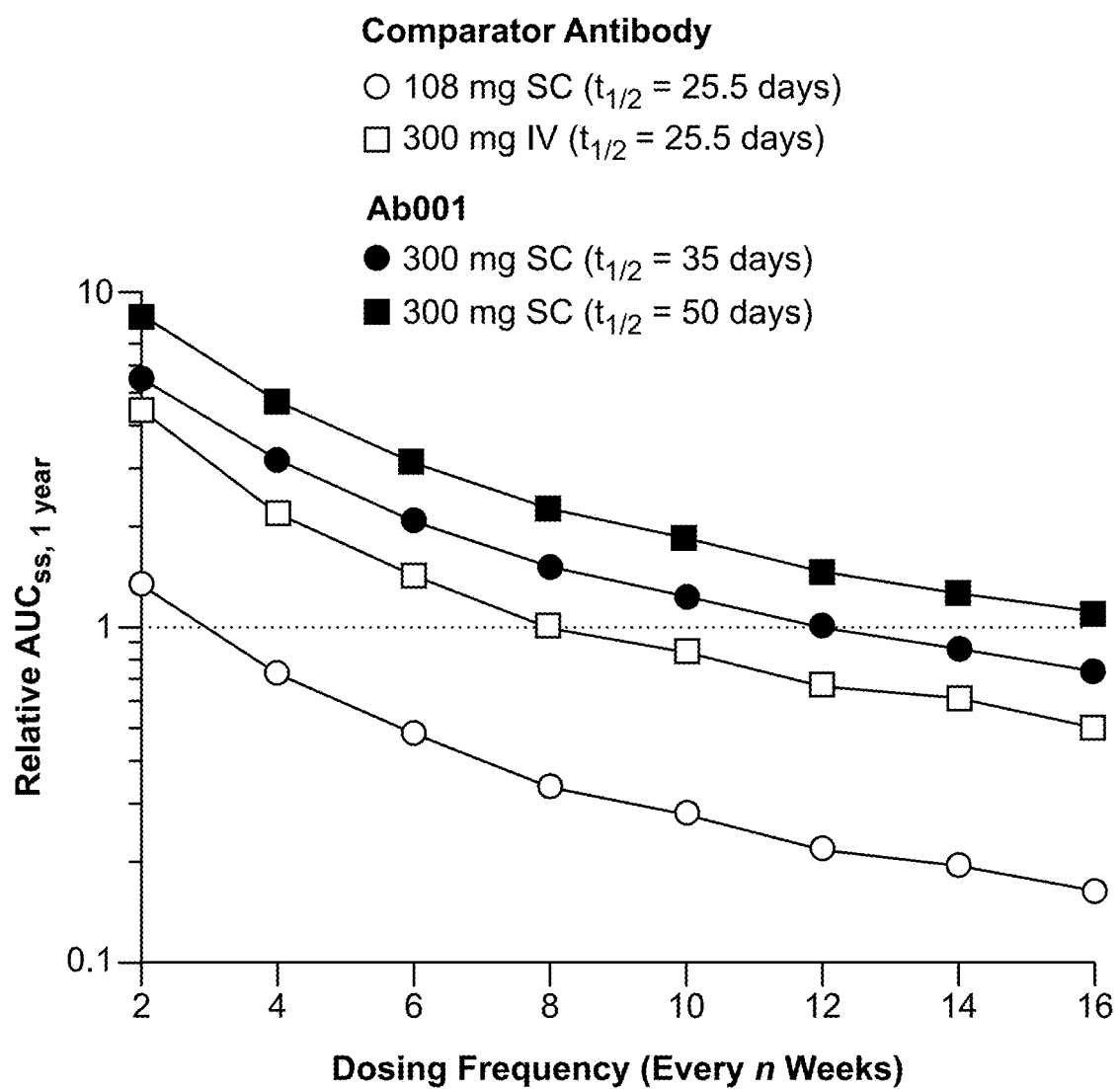
FIG. 5 depicts quarterly maintenance dosing of α4β7 binding antibody to maintain clinically relevant AUC levels. Relative $AUC_{ss, 1\ year}$ values were calculated using simulated trial of 1000 patients for an α4β7 binding antibody described herein (e.g., Ab001) with a half-life of 35 or 50 days and compared to clinical trial data for intravenously (IV) and subcutaneously (SC) dosed comparator antibody. Relative $AUC_{ss, 1\ year}$ values were calculated for a quarterly dosing frequency ranging from 2 weeks (Q2W) to 16 weeks (Q16W).

The best in class efficacy maintenance dosing of the comparator antibody is based on area under the curve at steady state ($AUC_{ss}$) data of Q8W IV maintenance dosing at 300 mg (FIG. 5). When dosed subcutaneously the comparator antibody can only be dosed at 108 mg Q2W without dropping below the clinically relevant AUC. In contrast, Ab001 is predicted to maintain clinically relevant AUC with quarterly maintenance subcutaneous dosing. These data were generated using a human half-life of 35 and 50 days for Ab001 and plotted with the comparator antibody data (FIG. 5). Depending on human half-life, this could be achieved even as infrequently as Q16W.

Figure 6:
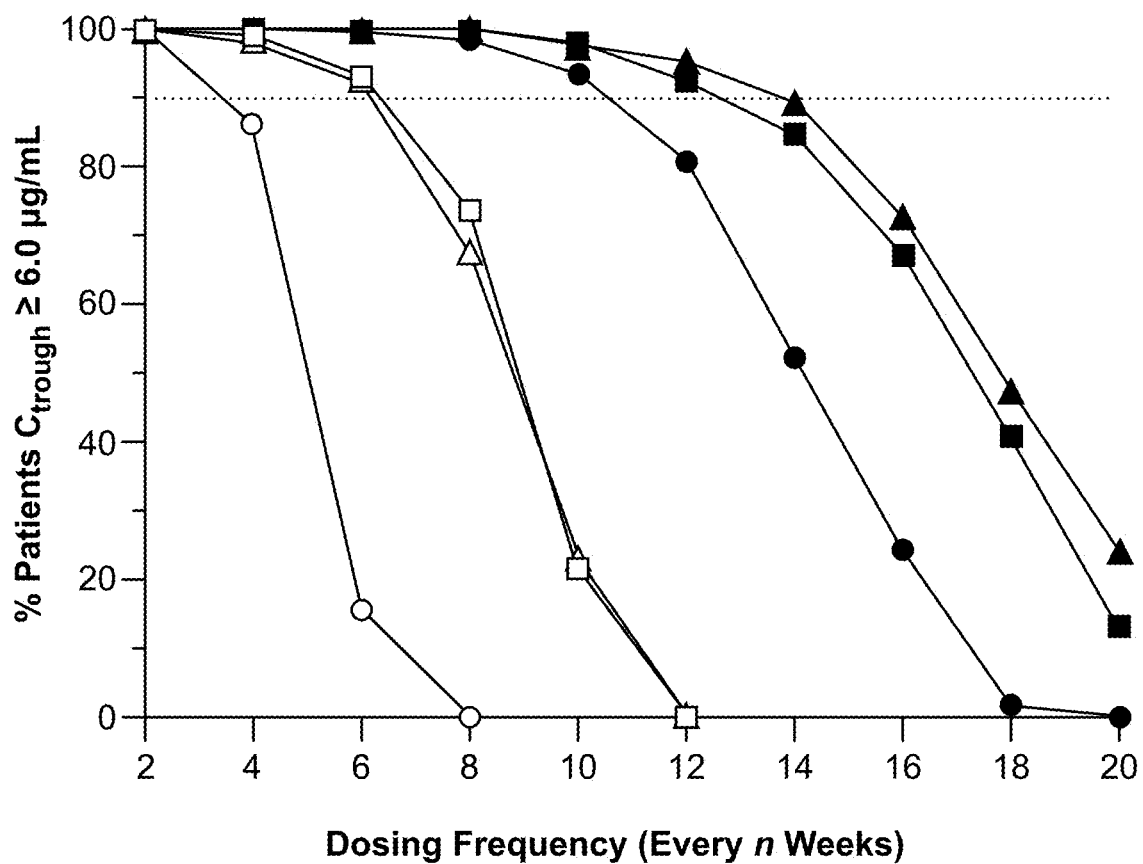
FIG. 6 depicts data from patients maintaining clinically relevant $C_{trough}$ values during maintenance dosing. In a simulated trial of 1000 patients, the percent of patients with a $C_{trough} \geq 6$ μg/ml was calculated for patients treated with comparator antibody dosed intravenously (IV; 300 mg dose) and subcutaneously (SC; 108 mg or 320 mg dose) and patients subcutaneously dosed with 300 mg of an α4β7 binding antibody described herein (e.g., Ab001) with a half-life of 43, 53 or 56 days. The percentage of patients with $C_{trough} \geq 6$ μg/ml were plotted for a dosing frequency ranging from Q2W to Q20W.

A post-hoc analysis of the comparator antibody trial data suggests a conservative target of $C_{trough}$≥6 μg/mL during treatment maintains long-term efficacy. Best-in-class 300 mg IV Q8W dosing of the comparator antibody showed 75% of patients had $C_{trough}$≥6 μg/mL. The comparator antibody dosed subcutaneously at 108 mg with a half-life of 25.5 days, dosed IV at 300 mg with a half-life of 25.5 days, and Ab001 dosed subcutaneously at 300 mg with a half-life of 43, 53, or 56 days was used to simulate a trial of 1000 patients (FIG. 6). Similar to clinical results, 65% of simulated patients with Q8W IV achieve $C_{trough}$≥6 μg/mL (65% is marked with a dashed line). Ab001 with a minimum 43-day half-life enables Q12W SC dosing. This matches the simulated comparator antibody IV Q8W dosing. Ab001 with a 50-day half-life at Q12W SC dosing results in more than 90% of patient with $C_{trough}$≥6 μg/mL. Dosing frequencies that maintained a clinically relevant $AUC_{ss}$ in FIG. 5 are indicated with stars.

Taken together, these data indicate Ab001 with a half-life of at least 35 days can be dosed subcutaneously with a Q12W frequency and maintain both a clinically relevant $C_{trough}$ and $AUC_{ss}$.

Example 4: Binding Affinity of α4β7 Binding Antibodies

This Example describes the binding affinity of the α4β7 binding α4β7 binding antibody Ab001.

Briefly, binding affinity of the α4β7 binding α4β7 binding antibody Ab001 to α4β7 was determined by Kinetic Exclusion Assay (KinExA) and flow cytometry, and functional activity was determined by inhibition of MAdCAM-mediated cellular adhesion.

The α4β7 binding α4β7 binding antibody Ab001 binds specifically to α4β7 and not to the related integrins α4β1 and αEβ7. In cellular assays, Ab001 binds α4β7 on the surface of RPMI-8866 cells with an affinity matching that of a comparator antibody, but it does not bind to Ramos cells expressing α4β1. The α4β7 binding α4β7 binding antibody Ab001 demonstrates high affinity for α4β7, with a $K_D$ of 836 pM determined by KinExA. Functionally, the α4β7 binding α4β7 binding antibody Ab001 potently inhibits MAdCAM-1-mediated cellular adhesion with an $IC_{50}$ comparable to that of a comparator antibody but has no inhibitory activity for VCAM-1-mediated cell adhesion.

Example 5: Simulation of Serum Concentrations of the α4β7 Binding Antibody

Figure 7A:
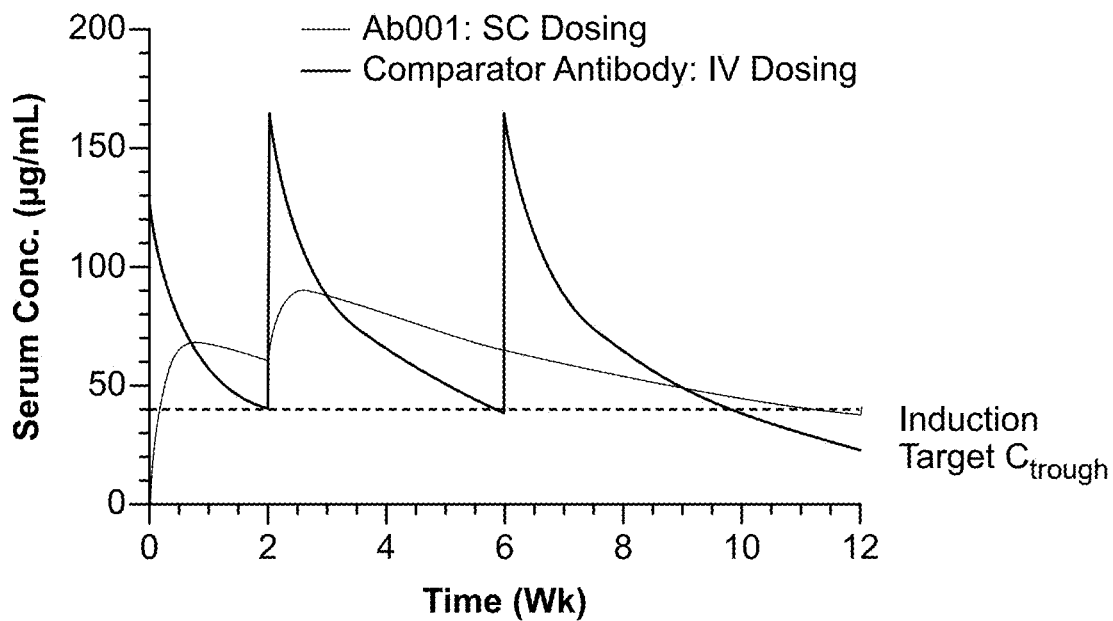
FIGS. 7A and 7B depict simulation of serum concentrations of the α4β7 binding antibody described herein (e.g., Ab001) and a comparator antibody.

A simulation was performed using induction scenarios as follows: (1) with an α4β7 binding α4β7 binding antibody described herein such as Ab001 at subcutaneous doses of 600 mg at week 0 (W0) and 300 mg at week 2 (W2) to determine the average serum concentration during the induction period of 12 weeks; (2) with the comparator antibody at intravenous dose of 300 mg at week 0, week 2 and week 6; and (3) with the comparator antibody at intravenous dose of 300 mg at week 0 and week 2, and a subcutaneous dose of 108 mg Q2W starting at week 6. FIG. 7A shows that $C_{avgW0-12}$ of Ab001 is greater than $C_{avgW0-12}$ of comparator antibody. FIG. 7C shows that $C_{avgW0-12}$ of Ab001 is greater than $C_{avgW0-12}$ of comparator antibody. Simulated patients with Q12W SC achieve a $C_{trough} \geq 36$ μg/mL which was higher than $C_{trough}$ of simulated patients with IV administration of the comparator antibody and which was higher than $C_{trough}$ of simulated patients with IV/SC administration of the comparator antibody. In addition, simulated patients with Q12W SC achieve maintain the $C_{trough} \geq 36$ μg/mL during the induction period.

Figure 7B:
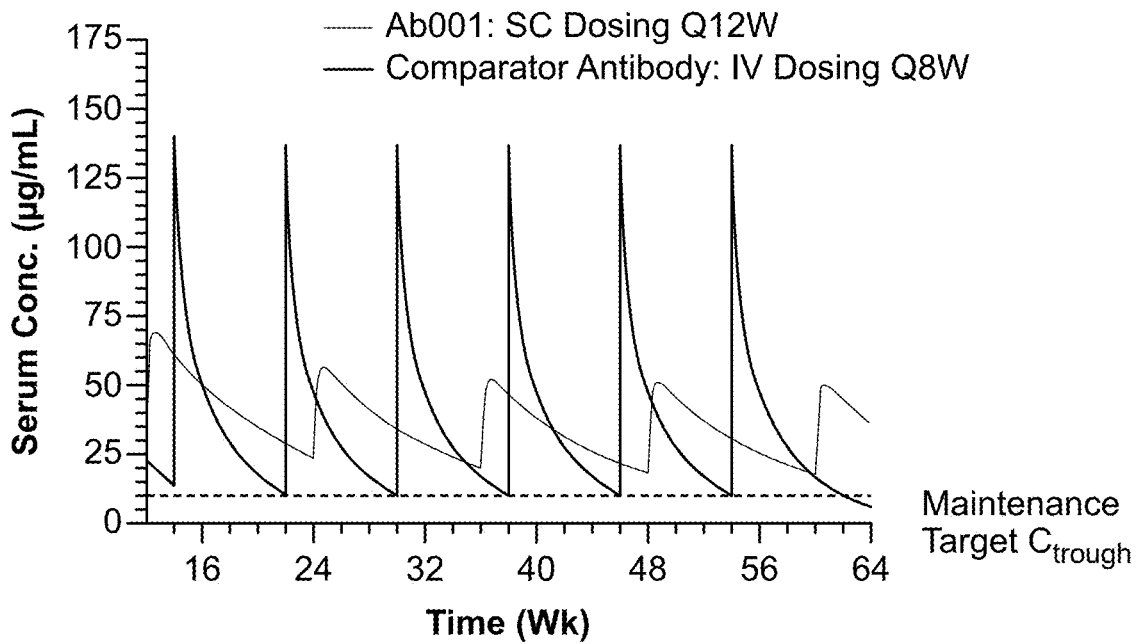
Figure 7C:
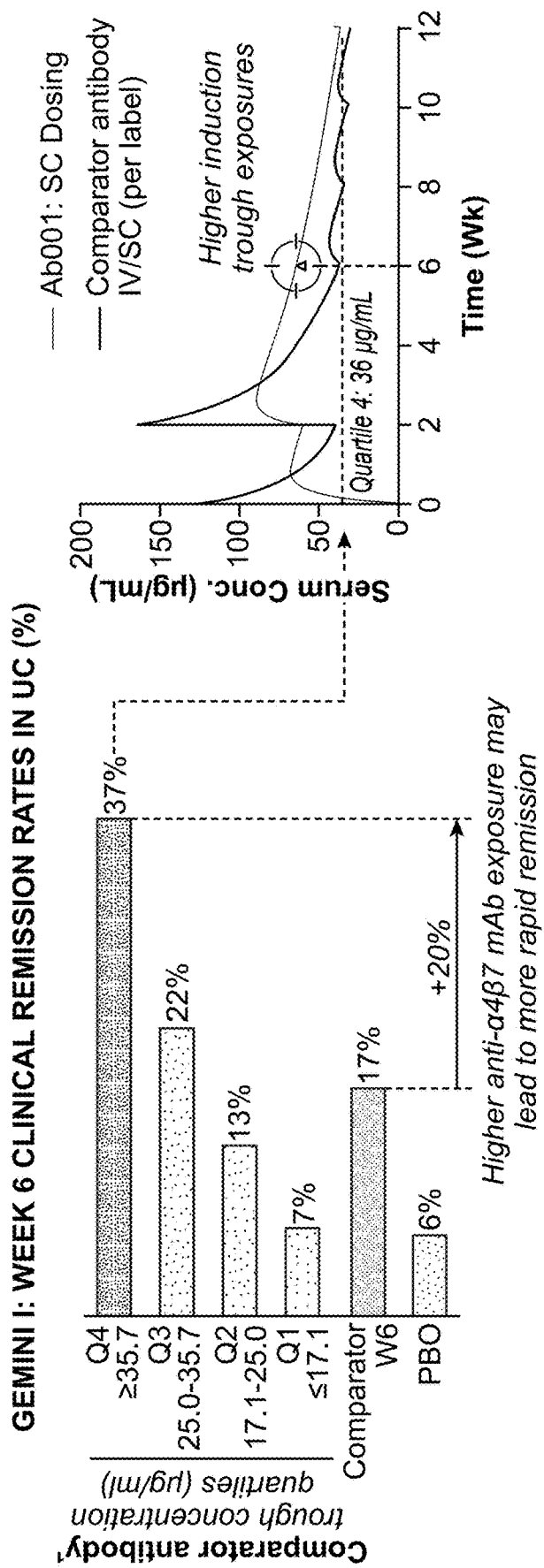
FIG. 7C (left) is a graph showing week 6 clinical remission rates in ulcerative colitis (%) (left)

FIG. 7B depicts serum concentrations based on 300 mg Q8W IV dosing of comparator antibody and 300 mg Q12W SC dosing of the α4β7 binding antibody described herein such as Ab001 based on the half-life of the antibodies. FIG. 7B shows that Q12W SC dosing of the α4β7 binding antibody described herein such as Ab001 results in a maintenance target $C_{trough} \geq 6$ μg/mL.

Figure 7D:
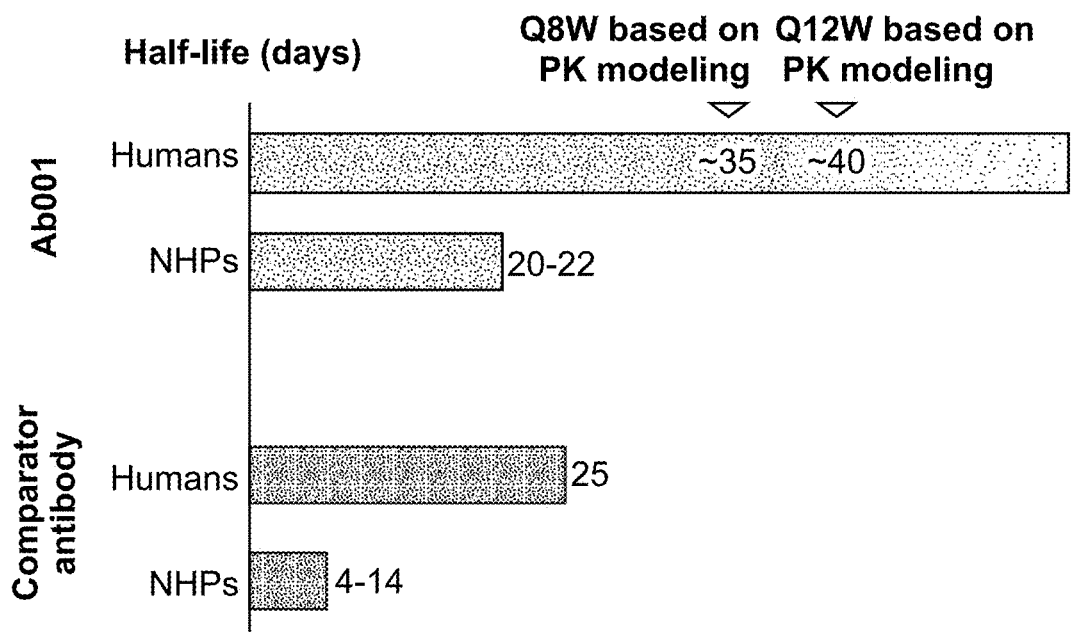
FIG. 7D is a graph showing human half-life predictions by NHP allometric scaling.
Figure 7E:
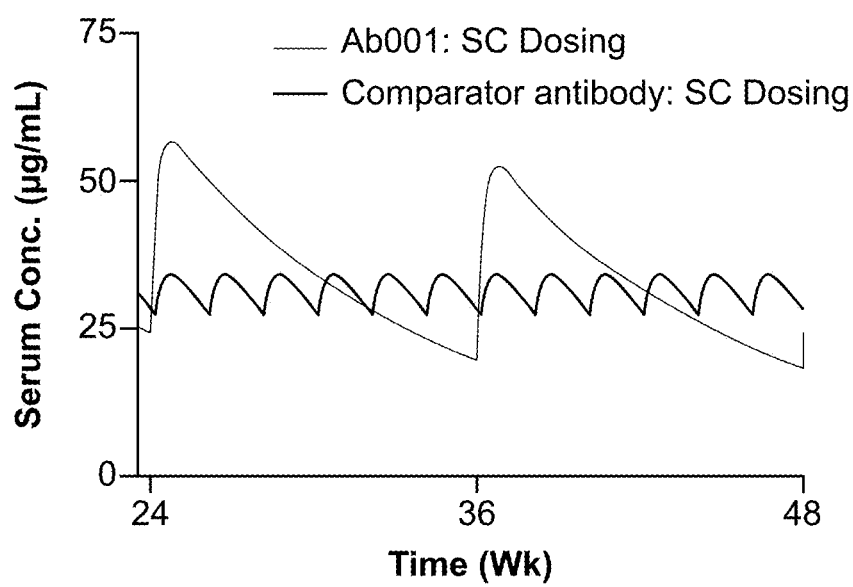
FIG. 7E depicts maintenance simulation of serum concentrations of the α4β7 binding antibody described herein (e.g., Ab001, 300 mg Q12W) and a comparator antibody (108 mg Q2W) when administered subcutaneously (300 mg Q12W for Ab001, 108 mg Q2W for comparator antibody).

FIG. 7D and FIG. 7E show that simulated patients with Q12W SC achieve an effective minimum average serum or plasma concentration of the α4β7 binding antibody described herein such as Ab001.

Figure 7F:
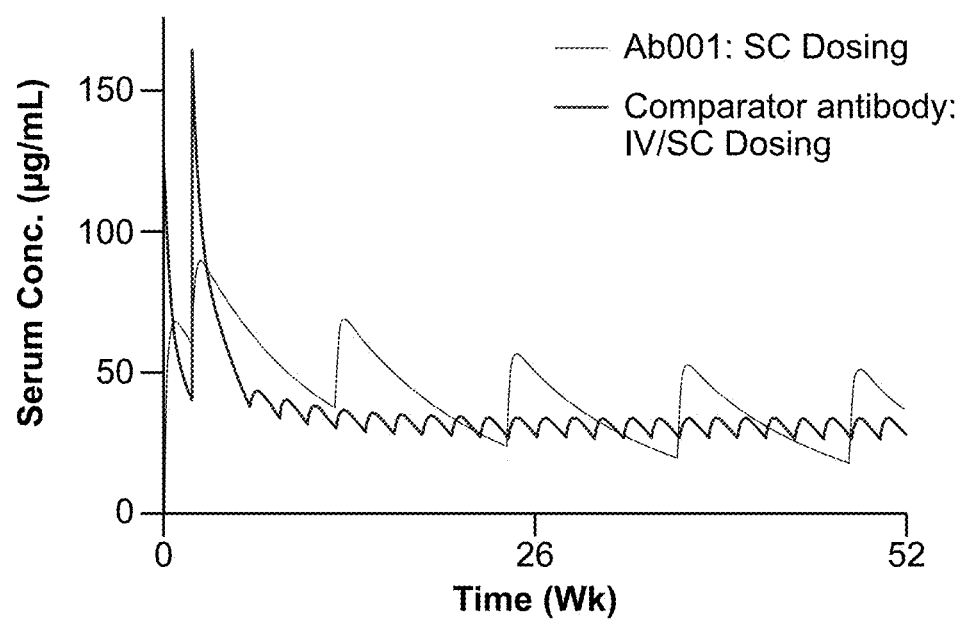
FIG. 7F show depicts simulation of serum concentrations of the α4β7 binding antibody described herein (e.g., Ab001, SC dosing, 4-6 injections per year for maintenance) and a comparator antibody (IV/SC dosing, 26 injections per year for maintenance).

FIG. 7F depicts serum concentrations based on dosing of comparator antibody at intravenous dose of 300 mg at week 0 and week 2, and a subcutaneous dose of 108 mg Q2W starting at week 6 (26 injections per year for maintenance), and based on dosing of the α4β7 binding antibody described herein such as Ab001 at subcutaneous doses of 300 mg Q12W (4-6 injections per year for maintenance), based on the half-life of the antibodies. FIG. 7F shows that the α4β7 binding antibody described herein such as Ab001 has a superior steady state profile for patients.

Example 6: PK Simulation of Serum Concentrations of the α4β7 Binding Antibody

Figure 8A:
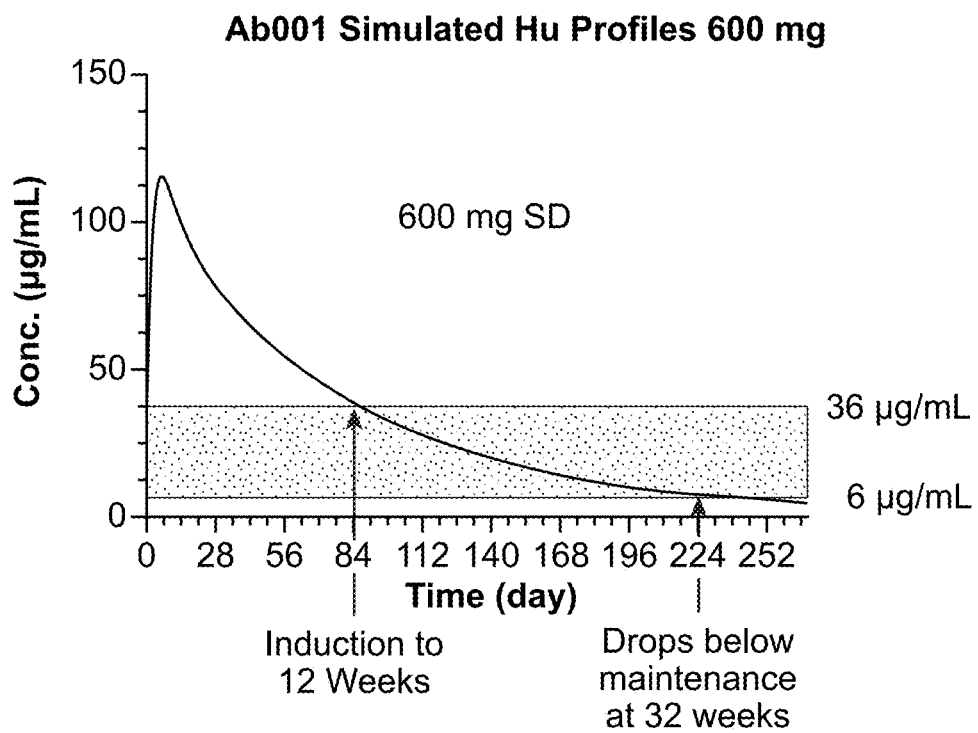
FIGS. 8A-8C are graphs showing human PK simulation (Simulated Using 75 mg/kg NHP-SC Dose (n=6, M/F)).
Figure 8B:
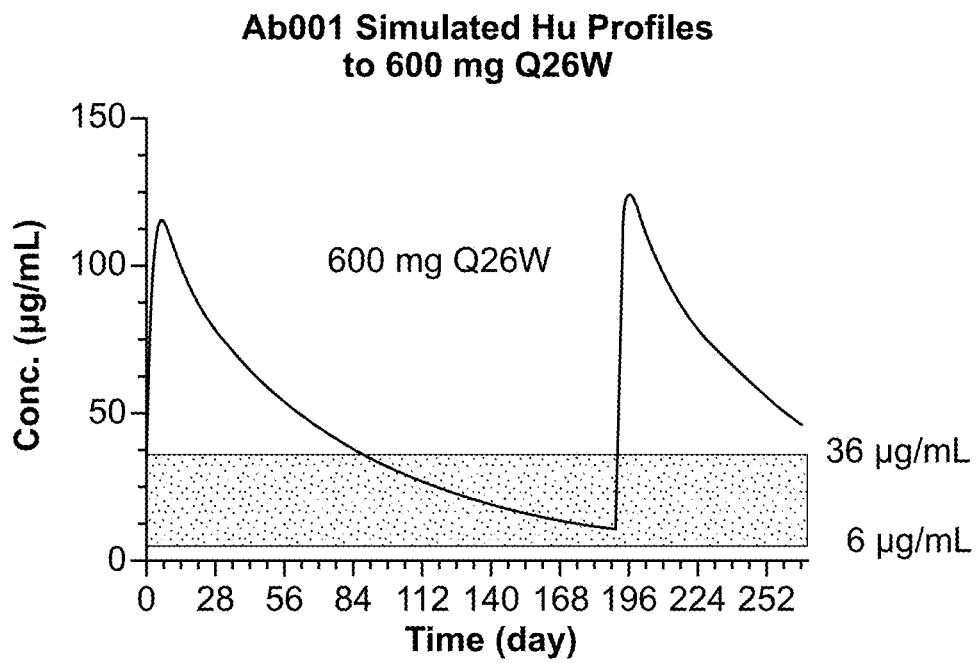
Figure 8C:
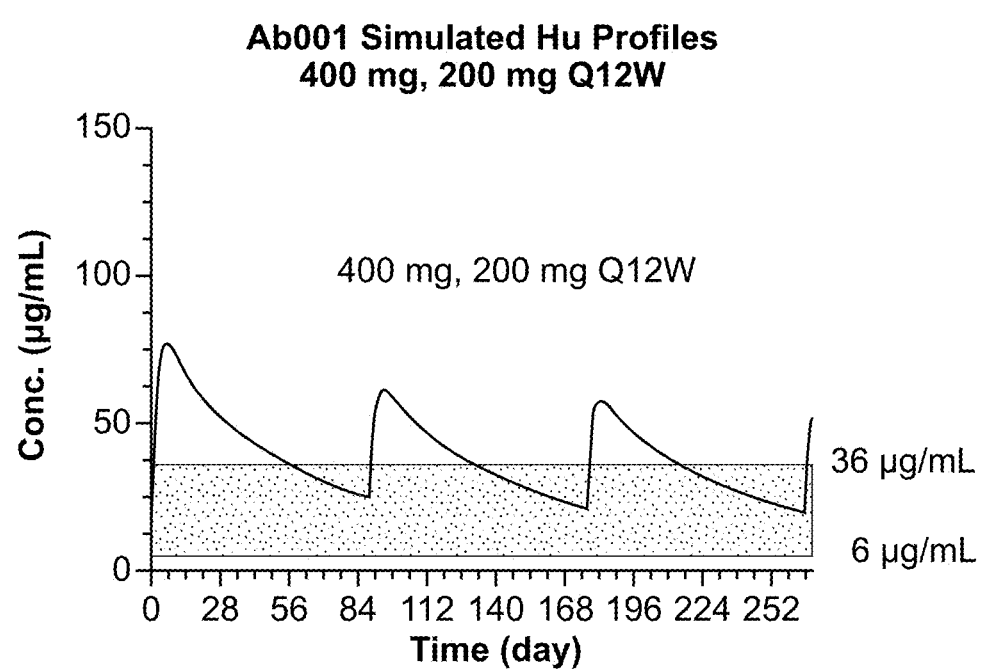
Figure 9:
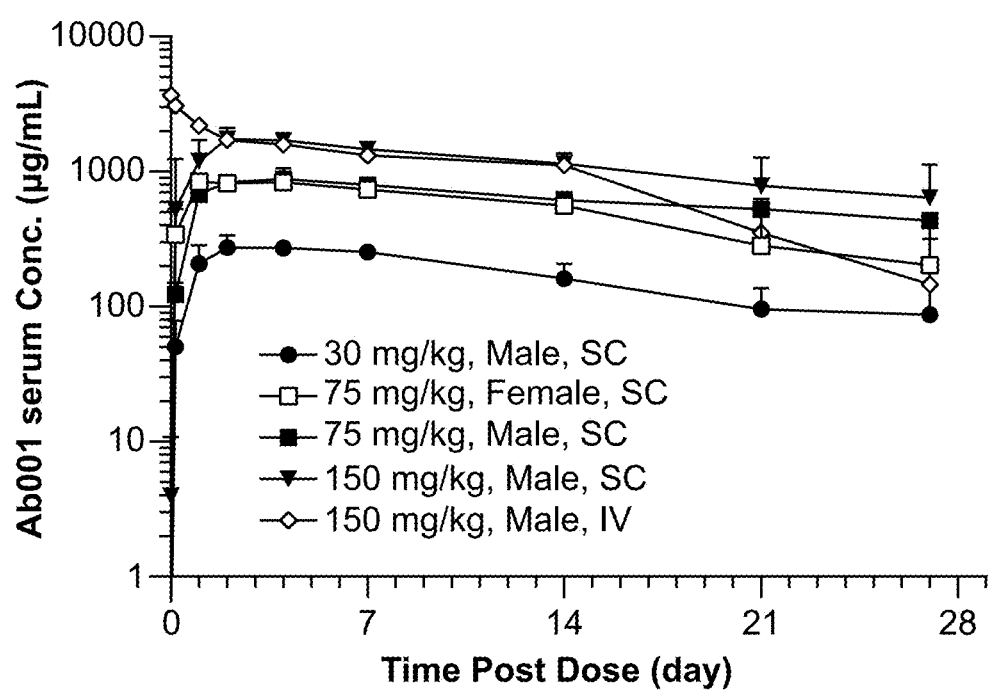
FIG. 9 is a graph showing serum concentration time profiles following subcutaneous and intravenous single-dose administration of α4β7 binding antibody Ab001 in male and female monkeys. The male and female monkeys were administered a single subcutaneous dose of either 30 mg/kg, 75 mg/kg or 150 mg/kg of Ab001, or a single intravenous dose of 150 mg/kg of Ab001.

FIGS. 8A-8C are graphs showing human PK simulation (Simulated Using 75 mg/kg NHP-SC Dose (n=6, M/F)). FIG. 8A is a graph showing the α4β7 binding antibody described herein such as Ab001 simulated human profiles at 600 mg. FIG. 8B is a graph showing α4β7 binding antibody described herein such as Ab001 simulated human profiles 600 mg Q26W. FIG. 8C is a graph showing α4β7 binding antibody described herein such as Ab001 simulated human profiles 400 mg, 200 mg, Q12W.

FIG. 8A shows that a single 600 mg dose remains above the induction threshold concentration for 12 weeks and drops below the maintenance concentration at 32 weeks.

FIG. 8B shows that simulation dosing of 600 mg α4β7 binding antibody described herein such as Ab001 Q26W (Q6M) maintains induction and maintenance concentration.

FIG. 8C shows that simulation dosing of 400 mg, 200 mg α4β7 binding antibody described herein such as Ab001 Q12W maintains induction and maintenance concentration.

Example 7: Summary of Key Binding Characteristics, Preclinical In Vitro and In Vivo Studies for the α4β7 Binding Antibody Ab001

TABLE 5

Study Summary

| Study Name | Study Description and Methods | Key Results and Conclusions |
|---|---|---|
| Functional Characterization of the α4β7 binding antibody Ab001 on α4β7 & α4β1 | Test system: α4β7-positive RPMI-8866 cells, α4β1-positive Ramos cells α4β7 and α4β1 double positive HuT-78 cells; fluorescence-activated cell sorting (FACS) Concentration range: 5 pM-100 nM 3 cell lines; 6 concentrations; three replicates | the α4β7 binding antibody Ab001 potency, α4β7: $EC_{50} = 0.15$ nM<br>the α4β7 binding antibody Ab001 potency, α4β1: $EC_{50}$ = NB<br>the α4β7 binding antibody Ab001 potency, α4β7, α4β1: $EC_{50} = 0.25$ nM<br>Comparator antibody potency, α4β7: $EC_{50} = 0.14$ nM<br>Comparator antibody potency, α4β1: $EC_{50}$ = NB<br>Comparator antibody potency, α4β1, α4β7: $EC_{50} = 0.24$ nM<br>The α4β7 binding antibody Ab001 exhibits functional, high-potency binding to α4β7 but not to α4β1. Natalizumab was included in this study as a positive control for functional α4β1 binding. |
| Binding Potencies and Receptor Occupancy of the α4β7 binding antibody Ab001 | Test system: Receptor Occupancy ($IC_{50}$) on CD4+, CD20+, and CD45RO+ Cells from Human Donors PBMCs and Monkey Donors PBMCs; titration of unlabeled Ab001 into samples equilibrated with EC50 concentrations of fluorescently labeled Ab001 | the α4β7 binding antibody Ab001; Human whole blood: $IC_{50}$ for all cell types = 0.53 nM<br>the α4β7 binding antibody Ab001; Human PBMCs: $IC_{50}$ for all cell types = 0.38 nM<br>the α4β7 binding antibody Ab001; Monkey PBMCs: $IC_{50}$ for all cell types = 0.50 nM<br>Comparator antibody; Human whole blood: $IC_{50}$ for all cell types = 0.44 nM<br>Comparator antibody; Human PBMCs: $IC_{50}$ for all cell types = 0.38 nM<br>Comparator antibody; Monkey PBMCs: $IC_{50}$ for all cell types = 0.56 nM |
| Determination of $K_D$ against α4β7, α4β1, and αEβ7 by SPR or KinExA | Test system: KinExA and surface plasmon resonance Concentration range: Varied by target n = 5 concentrations | The α4β7 binding antibody Ab001 $K_D$ v. α4β7 = 836 pM<br>The α4β7 binding antibody Ab001 $K_D$ v. α4β1 = NB<br>The α4β7 binding antibody Ab001 $K_D$ v. αEβ7 = NB |

TABLE 5-continued

Study Summary

| Study Name | Study Description and Methods | Key Results and Conclusions |
|---|---|---|
| Species Cross-reactivity and Binding Affinity Determination | Test system: SPR with multiple cycle kinetics | Comparator antibody $K_D$ v. $\alpha 4\beta 7$ = 562 pM<br>Comparator antibody $K_D$ v. $\alpha 4\beta 1$ = NB<br>Comparator antibody $K_D$ v. $\alpha E\beta 7$ = NB<br>Natalizumab was included in this study as a positive control for functional $\alpha 4\beta 1$ binding.<br>the $\alpha 4\beta 7$ binding antibody Ab001 Cyno-$\alpha 4\beta 7$ $K_D$ = 2.72 nM<br>the $\alpha 4\beta 7$ binding antibody Ab001 Dog-$\alpha 4\beta 7$ $K_D$ = 4.81 nM<br>the $\alpha 4\beta 7$ binding antibody Ab001 Rabbit-$\alpha 4\beta 7$ $K_D$ = 6.26 nM<br>the $\alpha 4\beta 7$ binding antibody Ab001 Rat-$\alpha 4\beta 7$ $K_D$ = NB<br>the $\alpha 4\beta 7$ binding antibody Ab001 Mouse-$\alpha 4\beta 7$ $K_D$ = NB<br>the $\alpha 4\beta 7$ binding antibody Ab001 Human-$\alpha 4\beta 7$ $K_D$ = 4.65 nM<br>Comparator antibody Cyno-$\alpha 4\beta 7$ $K_D$ = 1.2 nM<br>Comparator antibody Dog-$\alpha 4\beta 7$ $K_D$ = 1.77 nM<br>Comparator antibody Rabbit-$\alpha 4\beta 7$ $K_D$ = 5.34 nM<br>Comparator antibody Rat-$\alpha 4\beta 7$ $K_D$ = NB<br>Comparator antibody Mouse-$\alpha 4\beta 7$ $K_D$ = NB<br>Comparator antibody Human-$\alpha 4\beta 7$ $K_D$ = 4.16 nM |
| Binding of Ab001 to Cells Isolated from Human, Rabbit, Mouse, and Rat PBMCs | Test system: binding to CD4$^+$ T cells, CD4$^+$CD45RO+ (human only), and either CD20$^+$ B cells or IgG$^+$ cells from cryopreserved PBMCs from human, mouse, rat, and rabbit, using flow cytometry | In human PBMCs, a dose-dependent increase in Ab001 binding was observed in CD4$^+$ T cells, CD4$^+$ CD45RO$^+$ memory T cells, and CD20$^+$ B cells. In rabbits, a dose-dependent increase in Ab001 binding was observed in a subset of PBMCs. No binding above background was observed in cells isolated from either mice or rats. The results were comparable to those of comparator antibody. |
| Binding of Ab001 to Human Monocytes, B Cells, NK Cells, and T cell Subtypes | Test system: binding to primary human monocytes, B cells, T cells (naïve, TEMRA, effector memory cells (EM), central memory cells (CM) and a human B-lymphoid cell line expressing $\alpha 4\beta 7$ and $\alpha 4\beta 1$ (RPMI-8226) was evaluated using fluorescence-activated cell sorting (FACS) and fluorescently labeled antibody | Ab001 preferentially bound to $\alpha 4\beta 7$-expressing B cells, NK cells, and T cells (naïve, TEMRA, effector memory, and central memory) similar to comparator antibody |
| Functional Characterization of the $\alpha 4\beta 7$ binding antibody Ab001 on MAdCAM-1 and VCAM-1 Mediated Adhesion | Test system: $\alpha 4\beta 1$ and $\alpha 4\beta 7$ expressing HuT-78 cells with coating of recombinant MAdCAM-1 or VCAM-1 Concentration range: 5 pM-100 nM n = 6 replicates | MAdCAM-1 Inhibition IC50:<br>the $\alpha 4\beta 7$ binding antibody Ab001= 0.086 nM<br>Comparator antibody = 0.083 nM<br>VCAM-1 Inhibition IC50:<br>the $\alpha 4\beta 7$ binding antibody Ab001= None<br>Comparator antibody = None<br>Natalizumab = 0.23 nM<br>Conclusion: the $\alpha 4\beta 7$ binding antibody Ab001 and a comparator antibody exhibit functional activities that are distinct from those of natalizumab. |
| Pharmacokinetic study of the $\alpha 4\beta 7$ binding antibody Ab001 in cynomolgus monkeys | Doses: 10 mg/kg Route of Administration: IV N = 6 per group | $T_{1/2}$ = 17 days (experiment 1)<br>$T_{1/2}$ = 22 days (experiment 2)<br>Conclusion: The half-life of the $\alpha 4\beta 7$ binding antibody Ab001 in male cynomolgus monkeys is 70% longer than that of a comparator antibody. |
| Mouse Tg276 pharmacokinetic study | Dose: 1, 5, and 10 mg/kg Route of administration: IV N = 5 males per group | Conclusion: the $\alpha 4\beta 7$ binding antibody Ab001 exhibited extended pharmacokinetic half-life in Tg276 mice (>200% longer than a comparator antibody). |

$K_D$: equilibrium dissociation constant between the antibody and its antigen
IC$_{50}$: half-maximal inhibitory concentration
EC$_{50}$: half maximal effective concentration
MAdCAM-1: Mucosal vascular addressin cell adhesion molecule 1
VCAM-1: Vascular cell adhesion protein 1

Example 8: Formulations

α4β7 binding antibody Ab001 drug substance has a deglycosylated molecular weight of 146,698.3 daltons. It is soluble to greater than 200 mg/mL as a colorless to brown, clear to opalescent liquid.

α4β7 binding antibody Ab001 drug product is a sterile liquid for injection supplied in 2 mL glass vials. Each single-use drug product vial contains a nominal volume of 2 mL of 150 mg/mL Ab001 in aqueous solution with histidine, arginine, ethylenedinitrotetraacetic acid disodium salt dihydrate (EDTA), and polysorbate 80.

Example 9: Toxicology and Toxicokinetics of the α4β7 Binding Antibody Ab001

Toxicokinetic assessment after single dose IV and SC dosing of α4β7 binding antibody Ab001 at 30, 75, and 150 mg/kg was conducted in male and female cynomolgus monkeys over 27 days. No PK outliers were observed, thus all animals were considered in the statistical analysis. α4β7 binding antibody Ab001 serum concentration-time profiles in male monkeys dosed intravenously (IV) displayed a biphasic decline with a mean terminal phase $t_{1/2}$ of 6.19±1.72 days, mean $AUC_{last}$ of 27200±4880 day·µg/mL and a mean Vss of 53.0±4.30 mL/kg. A sharp increase in CL was noted after 14 days, consistent with the development of ADAs. When male and female monkeys were dosed SC, $T_{max}$ values ranged between 1 and 7 days. Ab001 exhibited linear dose proportionality when considering $C_{max}$ and $AUC_{last}$. Mean terminal $t_{1/2}$ values ranged from 10.2 to 24.2 days. There were no statistical differences (t test, p=0.05) in exposure at the 75 mg/kg dose between male and female monkeys when considering $C_{max}$ and AUC.

α4β7 binding antibody Ab001 serum concentration-time profiles in male monkeys dosed IV (150 mg/kg) displayed a biphasic decline with a mean (+SD) terminal phase $t_{1/2}$ of 6.19±1.72 days, mean (±SD) $AUC_{last}$ of 27200±3200 day·µg/mL and a mean (±SD) Vss of 53.0±4.30 mL/kg. A sharp increase in CL was noted after 14 days in this cohort, indicating the probable formation of ADAs.

$T_{max}$ values for male and female monkeys dosed SC ranged between 1 and 7 days. α4β7 binding antibody Ab001 exhibited approximately dose-linear pharmacokinetics when considering $C_{max}$ and $AUC_{last}$. Mean terminal $t_{1/2}$ values ranged from 10.2 to 24.2 days. There were no statistical differences (t-test, p=0.05) in exposure at 75 mg/kg between male and female monkeys when considering $C_{max}$ and $AUC_{last}$.

Overall, serum exposures of α4β7 binding antibody Ab001 after SC dosing were proportional to dose when considering $C_{max}$ (maximum mean concentration) and $AUC_{last}$ (area under the concentration/time curve from 0 to 648 hr) (Table 15). Mean (±SD) $C_{max}$ values ranged from 297±46.9 to 1780±315 µg/mL, and $AUC_{last}$ ranged from 4590±600 to 30500±6460 day·µg/mL. Exposures ($AUC_{last}$ and $C_{max}$) were similar in male and female animals after a 75 mg/kg SC dose. Ab001 IV dosing at 150 mg/kg resulted in a mean $AUC_{last}$ exposure of 27200±3200 day·µg/mL and a mean $C_{max}$ of 3670±433 µg/mL.

α4β7 binding antibody Ab001 was then administered to male and female cynomolgus monkeys (n=3/sex/group) every two weeks (Q2W) (doses on Day 1, Day 15, and Day 29) for 1 month at 0 (SC and IV; vehicle control), 25 (SC), 80 (SC), 160 (SC), and 160 mg/kg (IV). All animals survived until their scheduled necropsy on Study Day 30. Bioanalytical samples were collected, processed, and analyzed using a validated GyroLab® bioanalytical method, and toxicokinetic parameters were determined using noncompartmental analysis. $AUC_{0-28d}$ and $C_{max}$ increased in a slightly more than dose-proportional manner after Q2W SC doses of 25, 80, and 160 mg/kg. No sex differences in exposure were observed. Following a single SC administration, median $T_{max}$ values were observed between 3.00 to 7.00 days post dose across dose levels, while $T_{max}$ values after the Day 15 dose were between 1.00 and 7.00 days. Mean (±SD) $AUC_{0-28d}$ exposures (combined sex) after biweekly SC dosing were 6180±2950, 28200±2260, and 71500±17000 day·µg/mL, respectively. The $C_{max}$ (±SD) after the SC doses on Day 15 was 430±291, 1380±151, and 4040±1380 µg/mL, respectively. The mean $AUC_{0-28d}$ (±SD) exposure (combined sex) after biweekly IV dosing at 160 mg/kg was 73200±12500 day·µg/mL, while the $C_{max}$ (±SD) was 4980±905 µg/mL. The mean accumulation ratio after a second biweekly dose was ≤1.4 (AUC) for all doses.

Anti-α4β7 binding antibody Ab001 binding antibodies were associated with decreased exposure in two females and one male animal at the 25 mg/kg SC dose, although these animals were still included in the TK calculations for this dose. The formation of ADAs had no impact on exposure at either the 80 mg/kg or the 160 mg/kg dose (NOAEL). Throughout the evaluation of the study, serum α4β7 binding antibody Ab001 concentrations (at $C_{min}$ for 25 mg/kg dose) were a minimum of 3300× above the EC50 of Ab001 for saturable binding. Exposures ($C_{max}$ and $AUC_{0-28d}$) were slightly more than dose-proportional, and no sex-related differences were observed.

Mean (±SD) $AUC_{0-28d}$ exposures (combined sex) after biweekly SC dosing were 6180±2950, 28200±2260, and 71500±17000 day·µg/mL at 25, 80, and 160 mg/kg, respectively. Mean (±SD) $C_{max}$ after SC doses on Day 15 were 430±291, 1380±151, and 4040±1380 µg/mL at 25, 80, and 160 mg/kg, respectively. The mean (±SD) $AUC_{0-28d}$ exposure (combined sex) after biweekly IV dosing at 160 mg/kg was 73200±12500 day·µg/mL, while the mean (±SD) $C_{max}$ was 4980±905 µg/mL. The mean accumulation ratio after a second biweekly dose was ≤1.40 (AUC) for all doses.

It was not clear whether α4β7 binding antibody Ab001 would demonstrate toxicity because of its half-life extension. The results showed that, despite this prior uncertainty, there were no macroscopic (e.g., organs) or microscopic (e.g., cells/tissues) findings at any dose.

Example 10: Human PK

Serum α4β7 binding antibody Ab001 concentration-time profiles in humans were predicted for single and multiple SC and IV injections of α4β7 binding antibody Ab001 over the dose range of 100 to 1000 mg. Steady-state α4β7 binding antibody Ab001 serum exposures were predicted using the following two resources: (1) α4β7 binding antibody Ab001 PK parameters in cynomolgus monkeys with interspecies extrapolation of CL parameters using published allometric exponents for half-life engineered monoclonal antibodies; and (2) literature values of PK parameters reported for vedolizumab, an approved therapeutic human IgG1 monoclonal antibody targeting α4β7 (Rosario et al. 2016, Clinical Drug Investigation 36 (11): 913-23).

α4β7 binding antibody assumptions were made: (i) Ab001 follows a biphasic decline after administration; (ii) pharmacokinetic parameters including CL and Vss do not change upon repeated dosing and do not change over the dose range of 100 to 1000 mg in a 70 kg human (as observed with vedolizumab); (iii) disease state does not have a significant influence on PK; (iv) target-mediated drug disposition (TMDD) has a small influence on PK; (v), there will be no anti-α4β7 binding antibody Ab001 antibody development or, if present, anti α4β7 binding antibody Ab001 antibodies do not have an impact on α4β7 binding antibody Ab001 PK.

The predicted terminal phase $t_{1/2}$ value of α4β7 binding antibody Ab001 in humans based on the above assumptions is approximately 64 days and is consistent with the expected extended half-life resulting from incorporation of the YTE mutation into the Fc domain. Vedolizumab has a reported human half-life of 25.5 days (Rosario et al. 2015, Alimentary Pharmacology & Therapeutics 42 (2): 188-202; Rosario et al. 2016). The predicted steady-state $C_{max}$ and AUC values for α4β7 binding antibody Ab001 in humans for single and multiple IV and SC dosing are shown in Table 6.

TABLE 6

Predicted Exposure in Humans After Single and Multiple SC and IV Administration

| Clinical Dose (mg/70 kg) | Route | Single Dose | | | Two Doses Given Q2W | | |
|---|---|---|---|---|---|---|---|
| | | $C_{max}$ μg/mL | $AUC_{0-28d}$ day • μg/mL | $AUC_{0-inf}$ day • μg/mL | $C_{max}$ μg/mL | $AUC_{0-28d}$ day • μg/mL | $AUC_{0-inf}$ day • μg/mL |
| 100 | SC | 12.0 | 281 | 568 | 22.3 | 436 | 1450 |
| 300 | | 37.2 | 900 | 2530 | 69.6 | 1360 | 5830 |
| 600 | | 75.0 | 1830 | 5880 | 141 | 2760 | 12800 |
| 900 | | 113 | 2760 | 9370 | 212 | 4150 | 19800 |
| 1000 | | 125 | 3070 | 10500 | 236 | 4620 | 22100 |
| 100 | IV | 33.3 | 432 | 874 | 47.6 | 695 | 2150 |
| 300 | | 100 | 1360 | 3640 | 145 | 2140 | 8170 |
| 600 | | 200 | 2740 | 8230 | 291 | 4320 | 17500 |
| 900 | | 300 | 4130 | 12900 | 437 | 6490 | 26800 |
| 1000 | | 333 | 4590 | 14500 | 486 | 7220 | 29900 |

$AUC_{x-yd}$=area under the serum concentration-time curve from time x to time y post dose (i.e., AUC over a dosing interval); $AUC_{0-inf}$=area under the serum concentration-time curve from time zero to infinity; $C_{max}$=maximum serum concentration over 28 days; IV=intravenous; SC=subcutaneous; Q2W=every two weeks.

Example 11: PK Induction Simulation of Serum Concentrations of the α4β7 Binding Antibody A simulation was performed using the following induction scenarios (1) with an α4β7 binding antibody described herein such as Ab001 at subcutaneous doses of 600 mg at week 0 (W0) and 300 mg at week 2 (W2) to determine the average serum concentration during the induction period of 12 weeks, (2) with an α4β7 binding antibody described herein such as Ab001 at subcutaneous doses of 600 mg at week 0 (W0), 300 mg at week 2 (W2) and 300 mg at week 6 (W6) to determine the average serum concentration during the induction period of 12 weeks, (3) with the comparator antibody at intravenous dose of 300 mg at week 0 (W0), week 2 (W2) and week 6 (W6) to determine the average serum concentration during the induction period of 12 weeks.

An analysis of FIG. 10A indicates that $C_{maxW0-12}$, $C_{minW0-12}$, and $C_{avgW0-12}$ of Ab001 at the subcutaneous induction dose of 600 mg at week 0 (W0) and 300 mg at week 2 (W2) was calculated to be 89.7 μg/mL, 37.4 μg/mL, and 60.7 μg/mL, respectively. An analysis of FIG. 10B indicates that $C_{maxW0-12}$, $C_{minW0-12}$, and $C_{avgW0-12}$ of Ab001 at the subcutaneous induction dose of 600 mg at week 0 (W0), 300 mg at week 2 (W2) and 300 mg at week 6 (W6) was calculated to be 94.7 μg/mL, 57.6 μg/mL, and 73.9 μg/mL, respectively. An analysis of FIG. 10C indicates that $C_{maxW0-12}$, $C_{minW0-12}$, and $C_{avgW0-12}$ of the comparator antibody at the intravenous dose of 300 mg at week 0 (W0), week 2 (W2) and week 6 (W6) was calculated to be 164 μg/mL, 22.9 μg/mL, and 65.1 μg/mL, respectively.

Example 12: PK Maintenance Simulation of Serum Concentrations of the α4β7 Binding Antibody A simulation was performed using maintenance scenarios (1) with an α4β7 binding antibody described herein such as Ab001 at subcutaneous doses of 600 mg every 26 weeks to determine the average serum concentration during the maintenance period from week 30 through week 60, (2) with an α4β7 binding antibody described herein such as Ab001 at subcutaneous doses of 300 mg every 12 weeks to determine the average serum concentration during the maintenance period from week 30 through week 60, (3) with the comparator antibody at intravenous dose of 300 mg every 8 weeks to determine the average serum concentration during the maintenance period from week 30 through week 60, and (4) with the comparator antibody at subcutaneous dose of 108 mg every 2 weeks to determine the average serum concentration during the maintenance period from week 30 through week 60.

Figure 11B:
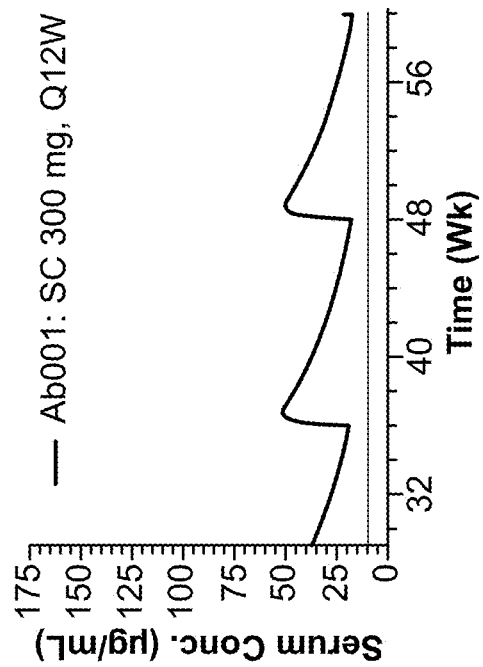
FIGS. 11A-11D are graphs showing human PK maintenance simulation studies for α4β7 binding antibody Ab001 relative to the comparator antibody based on NHP $t_{1/2}$ data.
Figure 11A:
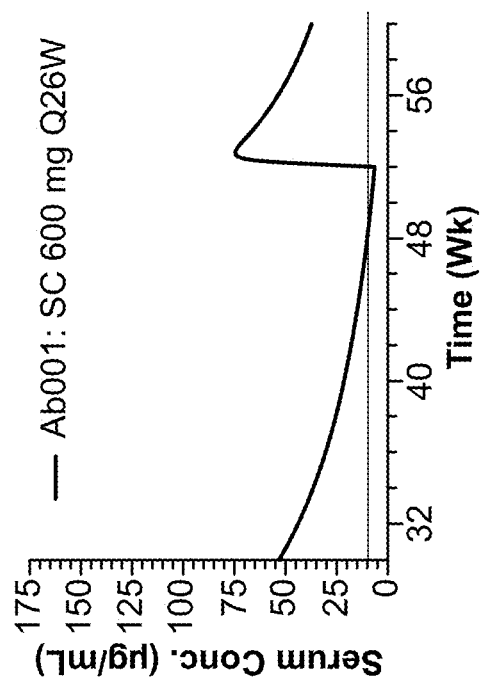
Figure 11D:
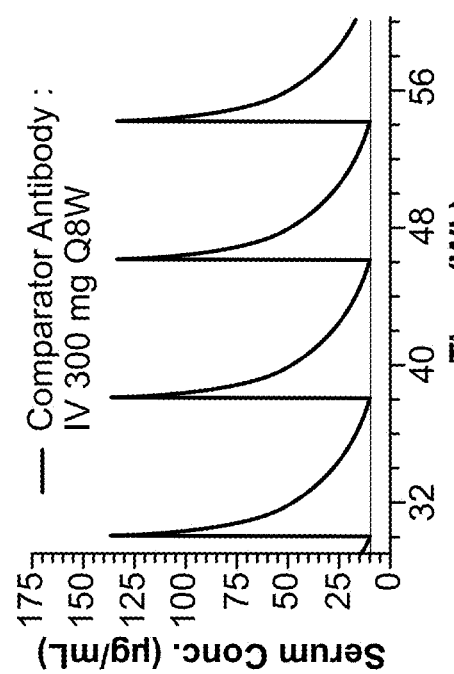
Figure 11C:
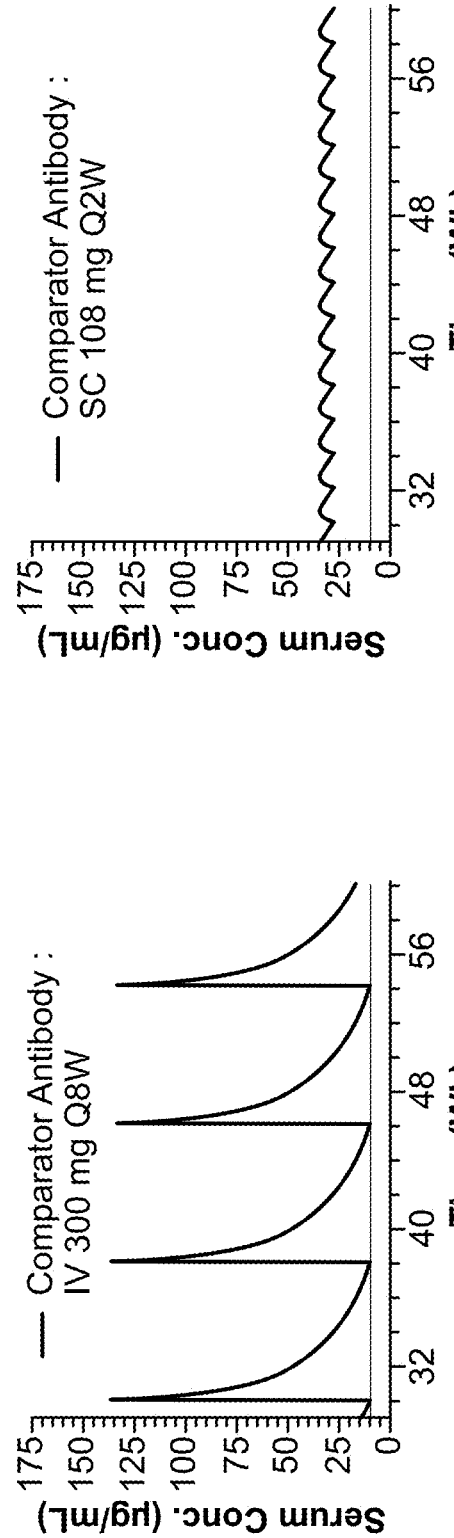

An analysis of FIG. 11A indicates that $C_{maxW30-60}$, $C_{minW30-60}$, and $C_{avgW30-60}$ of Ab001 at the subcutaneous maintenance dose of 600 mg every 26 weeks was calculated to be 74.8 μg/mL, 7.13 μg/mL, and 31.2 μg/mL, respectively. An analysis of FIG. 11B indicates that $C_{maxW30-60}$, $C_{minW30-60}$, and $C_{avgW30-60}$ of Ab001 at the subcutaneous maintenance dose of 300 mg every 12 weeks was calculated to be 50.6 μg/mL, 17.8 μg/mL, and 31.3 μg/mL, respectively. An analysis of FIG. 11C indicates that $C_{maxW30-60}$, $C_{minW30-60}$, and $C_{avgW30-60}$ of the comparator antibody at the intravenous dose of 300 mg every 8 weeks was calculated to be 136 μg/mL, 10.1 μg/mL, and 37.6 μg/mL, respectively. An analysis of FIG. 11D indicates that $C_{maxW30-60}$, $C_{minW30-60}$, and $C_{avgW30-60}$ of the comparator antibody at the subcutaneous dose of 108 mg every 2 weeks was calculated to be 33.7 μg/mL, 27.2 μg/mL, and 31.1 μg/mL, respectively.

Example 13: Single Ascending Dose Simulation of α4β7 Binding Antibody

A single ascending dose simulation was performed for two scenarios: (1) with an α4β7 binding antibody described herein such as Ab001 at 600 mg to determine serum concentration of Ab001 during the period of 84 days from the administration, and (2) with an α4β7 binding antibody described herein such as Ab001 at 300 mg to determine serum concentration of Ab001 during the period of 84 days from the administration.

Figure 12:
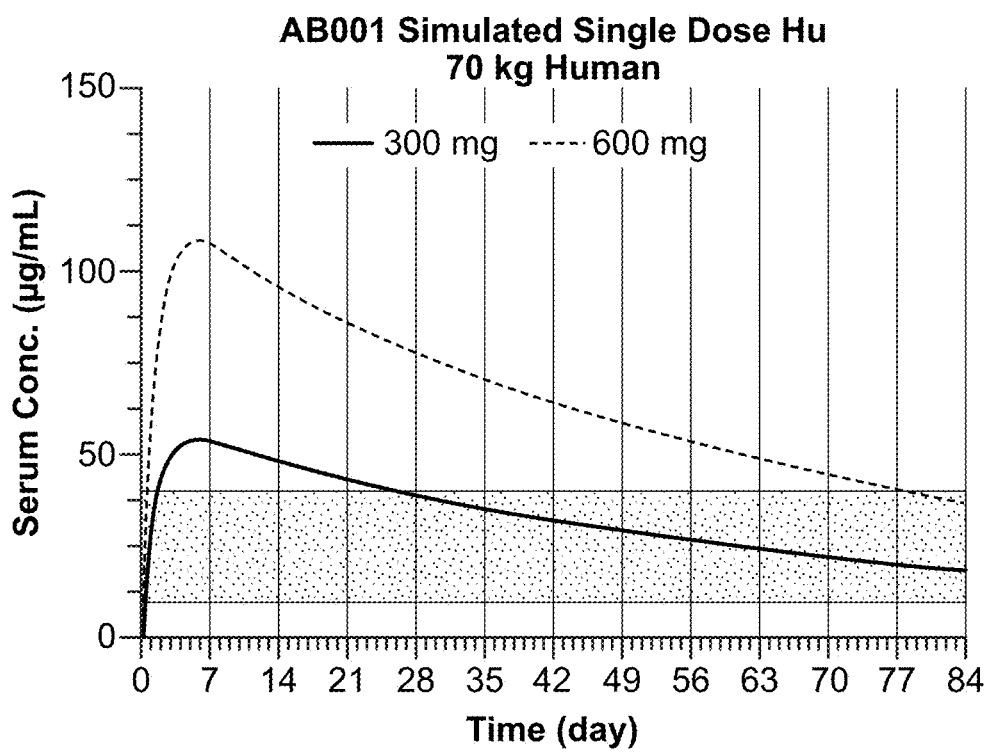
FIG. 12 is a graph showing human PK simulation profile for α4β7 binding antibody described herein such as Ab001 at 600 mg and 300 mg in a single ascending dose study.

FIG. 12 shows a comparison of simulated serum concentration of Ab001 at 600 mg and 300 mg dose of Ab001. An analysis of FIG. 12 indicates that serum concentration of Ab001 in both scenarios remain within concentration range of 10 μg/mL and 40 μg/mL after 84 days of administration.

Example 14: Multiple Ascending Dose Simulation of α4β7 Binding Antibody

A multiple ascending dose simulation was performed for two scenarios: (1) with an α4β7 binding antibody described herein such as Ab001 at subcutaneous doses of 600 mg on Day 0 (D0) followed by 600 mg subcutaneous dose on Day 14 (D14) to determine serum concentration of Ab001 during the period of 56 days from the administration, and (2) with an α4β7 binding antibody described herein such as Ab001 at subcutaneous doses of 600 mg on Day 0 (D0) followed by 600 mg subcutaneous dose on Day 14 (D14) to determine serum concentration of Ab001 during the period of 56 days from the administration.

Figure 13:
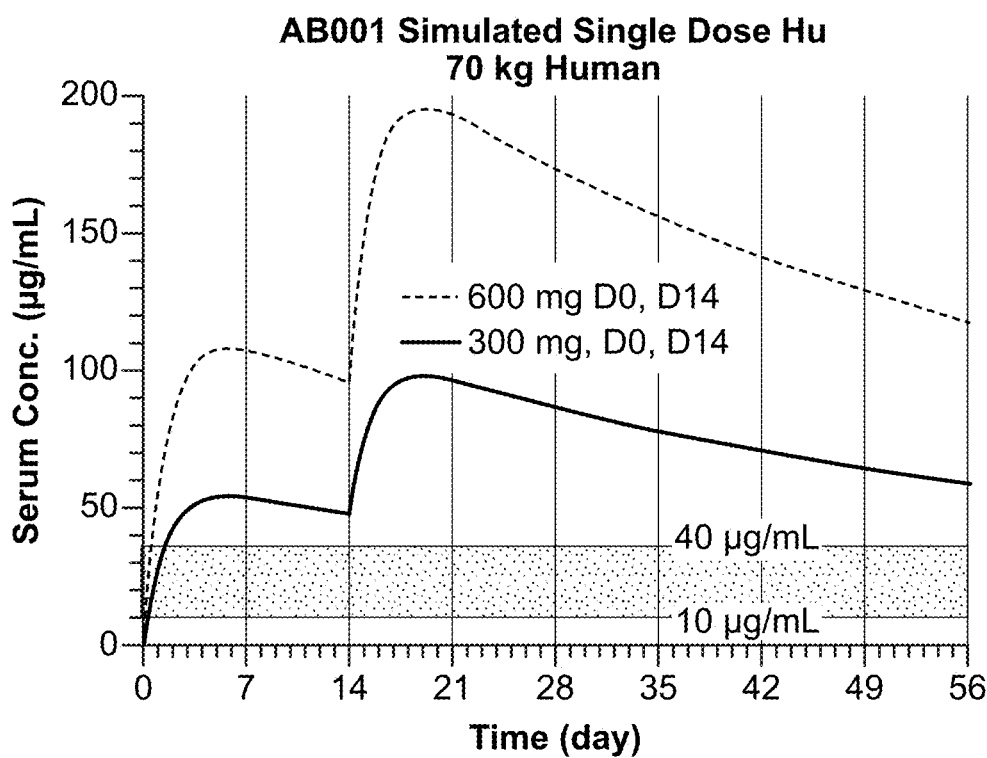
FIG. 13 is a graph showing human PK simulation profile for α4β7 binding antibody described herein such as Ab001 at 600 mg and 300 mg in a multiple ascending dose study.

FIG. 13 shows a comparison of simulated serum concentration of Ab001 at 600 mg and 300 mg dose of Ab001. An analysis of FIG. 13 indicates that serum concentration of Ab001 in both scenarios remain above 40 μg/mL after 56 days of administration.

Example 15: Clinical Efficacy of α4β7 Binding Antibody

Vedolizumab has demonstrated some efficacy in treatment of ulcerative colitis (UC) and Crohn's disease (CD) (ENTYVIO Product Monograph). This antibody has a serum half-life of 26 days in human subjects (25 days according to the product insert). Various factors increase clearance of vedolizumab, including albumin, body weight, fecal calprotectin, prior treatment with TNF antagonist drugs, and presence of anti-vedolizumab antibody. In patients administered 300 mg vedolizumab as a 30-minute intravenous infusion on Weeks 0 and 2, median serum trough concentration at Week 6 was 25.6 mcg/mL (range 0.9 to 140.0) in ulcerative colitis and 24.5 mcg/mL (range 1.1 to 177.0) in Crohn's Disease. Median steady state serum trough concentrations were 9.8 mcg/mL (range 2.4 to 42.8) and 11.2 mcg/mL (0.4 to 54.5), respectively, in patients with ulcerative colitis and Crohn's disease, when 300 mg vedolizumab was administered intravenously every eight weeks starting at week 6.

Clinical trials evaluated efficacy and safety of intravenous (for induction) and intravenous or subcutaneous vedolizumab for the maintenance treatment of adult patients with moderately to severely active ulcerative colitis (Mayo score 6 to 12 with endoscopic sub score ≥2). The primary endpoint of the induction phase was proportion of patients with clinical response at Week 6. The primary endpoint for the subcutaneous study was the proportion of patients in clinical remission (complete Mayo score of ≤2 points and no individual subscore >1 point) at Week 52. Secondary endpoints were mucosal healing (Mayo endoscopic subscore of ≤1 point) at Week 52; durable clinical response (clinical response at Weeks 6 and 52); durable clinical remission (clinical remission at Weeks 6 and 52); and corticosteroid-free clinical remission (patients using oral corticosteroids at baseline who had discontinued corticosteroids and were in clinical remission) at Week 52.

The efficacy and safety of intravenous (for induction) and subcutaneous (for maintenance) vedolizumab for the treatment of adult patients with moderately to severely active Crohn's disease (CDAI score of 220 to 450) was evaluated in a randomized, double-blind, placebo-controlled study evaluating efficacy endpoints at Week 6 (induction) and Week 52 (maintenance). The primary endpoint was the proportion of patients with clinical remission (CDAI score≤150). The secondary endpoints were enhanced clinical response; corticosteroid free remission; and clinical remission in TNFα antagonist naïve patients, at Week 52.

α4β7 binding antibody Ab001 is evaluated in clinical trials in patients with ulcerative colitis and Crohn's disease with various primary and secondary endpoints, such as clinical remission in both ulcerative colitis and Crohn's disease, endoscopic improvement (mucosal healing) in ulcerative colitis, durable clinical response in ulcerative colitis, durable clinical remission in ulcerative colitis, enhanced clinical response in Crohn's disease, clinical remission in advanced therapy (such as a TNFα antagonist) naïve patients in Crohn's disease, and corticosteroid-free clinical remission in both ulcerative colitis and Crohn's disease. Biomarker tests are conducted at Week 6, including C-reactive protein (CRP), fecal calprotectin, and symptoms.

In a clinical study, the characteristics of the α4β7 binding antibody Ab001 provide for greater proportion of patients achieving clinical remission in both ulcerative colitis and Crohn's disease than previously observed with vedolizumab.

In a clinical study, the characteristics of the α4β7 binding antibody Ab001 provide for greater endoscopic improvement in ulcerative colitis than previously observed for vedolizumab.

In a clinical study, the characteristics of the α4β7 binding antibody Ab001 provide for greater mucosal healing in ulcerative colitis than previously observed for vedolizumab.

In a clinical study, the characteristics of the α4β7 binding antibody Ab001 provide for greater durable clinical response in ulcerative colitis than previously observed for vedolizumab.

In a clinical study, the characteristics of the α4β7 binding antibody Ab001 provide for greater durable clinical remission in ulcerative colitis than previously observed for vedolizumab.

In a clinical study, the characteristics of the α4β7 binding antibody Ab001 provide for greater enhanced clinical response in Crohn's disease than previously observed for vedolizumab.

In a clinical study, the characteristics of the α4β7 binding antibody Ab001 provide for greater clinical remission in TNFα antagonist naïve patients in Crohn's disease than previously observed for vedolizumab.

In a clinical study, the characteristics of the α4β7 binding antibody Ab001 provide for greater corticosteroid-free clinical remission in both ulcerative colitis and Crohn's disease than previously observed for vedolizumab.

In a clinical study, the characteristics of the α4β7 binding antibody Ab001 provide for improvements in biomarkers, including CRP, fecal calprotectin, and symptoms at Week 6 than previously observed for vedolizumab.

Example 16: Two-Compartment PK Model

To inform first-in-human dosing of Ab001, a two-compartment pharmacokinetic (PK) model was built and calibrated to data from cynomolgus monkeys (N-34). The model included mechanisms for intercompartmental transport and elimination of drug, and it addressed target-mediated drug disposition (TMDD) through an empirical Michaelis-Menten elimination function. The model parameters were allometrically scaled to humans using scaling exponents specific to YTE-containing mAbs. Single and biweekly administration of drug via IV and SC were simulated. PK metrics, including the maximum drug concentration ($C_{max}$), area under the PK curve (AUC) and trough concentration ($C_{min}$), were calculated for each dosing scenario and are reported here.

The two-compartment PK model was calibrated to preclinical PK datasets for cynomolgus monkeys for both drug molecules, Ab001 and the comparator antibody. The parameters Thalf, Vmax, and Km were fitted to the mean measurements of the IV-administered data set for Ab001. For the SC administered dataset, the parameters $T_{1/2}$, $V_{max}$, and $K_m$ were taken from IV fits, and optimized bioavailability (F) came out to be 100%, and absorption half-life ($T_{1/2}$, SC) to be 1.08 days. The fitted parameters were used to simulate cynomolgus monkey preclinical data for both IV and SC routes.

For comparator antibody preclinical fits, 10 and 50 mg/kg datasets were available for both IV and SC-administered routes. The data in the 10 mg/kg IV dose group ≥20 days were not included in calibration, as these points showed an anomalous increase in serum drug levels. The parameters $T_{1/2}$, $V_{max}$, $K_m$, $P_{dist12}$, and $V_c$ were fitted to capture the IV-administered dataset. A lower value of optimized central volume was found for the comparator antibody, which was required to capture the $C_{max}$ for the IV dataset. For the SC administered dataset, the parameters $T_{1/2}$, $V_{max}$, $K_m$, $P_{dist12}$, and $V_c$ were taken from the IV calibrations and the model simulations were overlaid to SC preclinical data. The bioavailability (F) and absorption half-life ($T_{1/2}$, SC) were set to those from Ab001 SC dose calibrated values.

The Ab001 half-life in cynomolgus monkeys was estimated to be 17.1 days, and for the comparator antibody it was estimated to be 9.74 days. Based on the respective value for each antibody and applying the allometric scaling, the half-life in humans was estimated in this study to be 63.7 days, and the critical concentration above which TMDD has a negligible effect is estimated to be 8 μg/mL. In a prior analysis the estimated half-life of Ab001 in humans was 54 days using the FcRn scaling factors. In this study the human serum half-life of the comparator antibody was estimated to be 38.5 days.

INCORPORATION BY REFERENCE

All publications and patents cited throughout the text of this specification (including all patents, patent applications, scientific publications, manufacturer's specifications, instructions, etc.), whether supra or infra, are hereby incorporated by reference in their entirety for all purposes. To the extent the material incorporated by reference contradicts or is inconsistent with this specification, the specification will supersede any such material.

EQUIVALENTS

The disclosure may be embodied in other specific forms without departing from the spirit or essential characteristics thereof. The foregoing embodiments are therefore to be considered in all respects illustrative rather than limiting the disclosure described herein. Scope of the disclosure is thus indicated by the appended claims rather than by the foregoing description, and all changes that come within the meaning and range of equivalency of the claims are intended to be embraced therein.

The invention claimed is:

1. A dosing regimen for use in treating gastrointestinal inflammatory disease in a subject in need thereof, the dosing regimen comprising:
(a) a first pharmaceutical formulation comprising a dosage amount of from about 150 mg to about 1200 mg of a long acting α4β7 targeting molecule for administration to the subject;
(b) a second pharmaceutical formulation comprising a dosage amount of from about 75 mg to about 600 mg of the long acting α4β7 targeting molecule for subcutaneous administration to the subject at least two weeks after the first pharmaceutical formulation, and thereafter as a maintenance dose at least four weeks after administration of the second pharmaceutical formulation, resulting in treatment of gastrointestinal inflammatory disease in the subject,
wherein the long acting α4β7 targeting molecule comprises:
(i) a heavy chain consisting of an amino acid sequence according to SEQ ID NO: 1, and
(ii) a light chain consisting of an amino acid sequence according to SEQ ID NO: 3;
wherein at least one of the first pharmaceutical formulation and the second pharmaceutical formulation (1) comprises from about 150 mg/ml to about 200 mg/ml of the long acting α4β7 targeting molecule, and (2) does not contain citrate.

2. The dosing regimen of claim 1, wherein the first formulation is for subcutaneous administration.

3. The dosing regimen of claim 1, wherein the first formulation is for intravenous administration.

4. The dosing regimen of claim 1, wherein the first formulation comprises a dosage amount of about 600 mg of the long acting α4β7 targeting molecule.

5. The dosing regimen of claim 1, wherein the second formulation comprises a dosage amount of about 300 mg of the long acting α4β7 targeting molecule.

6. The dosing regimen of claim 1, wherein the dosage amount of the first formulation is about 2 or more times higher than a dosage amount of each maintenance dose.

7. The dosing regimen of claim 1, wherein the first formulation is suitable for administration as a single injection or multiple injections.

8. The dosing regimen of claim 1, wherein the first formulation and the second formulation do not contain citrate.

9. The dosing regimen of claim 8, wherein the first formulation or second formulation or both formulations comprise one or more of:

(a) histidine;
(b) arginine or a salt thereof;
(c) ethylenediaminetetraacetic acid (EDTA); and
(d) polysorbate 80.

10. The dosing regimen of claim 1, wherein the gastrointestinal inflammatory disease is Crohn's disease.

11. The dosing regimen of claim 1, wherein the gastrointestinal inflammatory disease is ulcerative colitis.

12. The dosing regimen of claim 1, resulting in a serum $C_{trough}$ of 35 µg/mL or greater six weeks following administration of the first formulation.

13. The dosing regimen of claim 1, resulting in a serum $C_{avgW0-W6}$ of from 65 µg/ml to 75 µg/ml or greater.

14. The dosing regimen of claim 1, resulting in a serum $C_{avgW0-W12}$ of from 60 µg/ml to 70 µg/ml or greater.

15. The dosing regimen of claim 1, resulting in a serum $C_{avgW30-W40}$ of at least 30 µg/ml.

16. The dosing regimen of claim 1, resulting in a steady state serum $C_{trough}$ of 6 µg/ml or greater following administration of the second formulation.

17. A dosing regimen for use in treating gastrointestinal inflammatory disease in a subject in need thereof, the dosing regimen comprising:
(a) a first pharmaceutical formulation comprising a dosage amount of at least 150 mg of a long acting α4β7 targeting molecule for subcutaneous administration to the subject;
(b) a second formulation pharmaceutical comprising a dosage amount of at least 75 mg of the long acting α4β7 targeting molecule for subcutaneous administration to the subject at least two weeks after the first pharmaceutical formulation, and thereafter as a maintenance dose at least four weeks after administration of the second pharmaceutical formulation, resulting in treatment of gastrointestinal inflammatory disease in the subject,
wherein the long acting α4β7 targeting molecule comprises:
(i) a heavy chain consisting of an amino acid sequence according to SEQ ID NO: 1, and
(ii) a light chain consisting of an amino acid sequence according to SEQ ID NO: 3;
wherein at least one of the first pharmaceutical formulation and second pharmaceutical formulation (1) comprises from about 150 mg/ml to about 200 mg/ml of the long acting α4β7 targeting molecule; and (2) does not contain citrate.

18. The dosing regimen of claim 17, wherein the dosage amount of the first formulation is about 2 or more times higher than a dosage amount of each maintenance dose.

* * * * *

SEQUENCE LISTING

```
Sequence total quantity: 17
SEQ ID NO: 1           moltype = AA  length = 450
FEATURE                Location/Qualifiers
source                 1..450
                       mol_type = protein
                       organism = synthetic construct
SEQUENCE: 1
QVQLVQSGAE VKKPGASVKV SCKGSGYTFT SYWMHWVRQA PGQRLEWIGE IDPSESNTNY   60
NQKFKGRVTL TVDISASTAY MELSSLRSED TAVYYCARGG YDGWDYAIDY WGQGTLVTVS  120
SASTKGPSVF PLAPSSKSTS GGTAALGCLV KDYFPEPVTV SWNSGALTSG VHTFPAVLQS  180
SGLYSLSSVV TVPSSSLGTQ TYICNVNHKP SNTKVDKKVE PKSCDKTHTC PPCPAPELAG  240
APSVFLFPPK PKDTLYITRE PEVTCVVVDV SHEDPEVKFN WYVDGVEVHN AKTKPREEQY  300
NSTYRVVSVL TVLHQDWLNG KEYKCKVSNK ALPAPIEKTI SKAKGQPREP QVYTLPPSRD  360
ELTKNQVSLT CLVKGFYPSD IAVEWESNGQ PENNYKTTPP VLDSDGSFFL YSKLTVDKSR  420
WQQGNVFSCS VMHEALHNHY TQKSLSLSPG                                  450

SEQ ID NO: 2           moltype = AA  length = 450
FEATURE                Location/Qualifiers
source                 1..450
                       mol_type = protein
                       organism = synthetic construct
SEQUENCE: 2
QVQLVQSGAE VKKPGASVKV SCKGSGYTFT SYWMHWVRQA PGQRLEWIGE IDPSESNTNY   60
NQKFKGRVTL TVDISASTAY MELSSLRSED TAVYYCARGG YDGWDYAIDY WGQGTLVTVS  120
SASTKGPSVF PLAPSSKSTS GGTAALGCLV KDYFPEPVTV SWNSGALTSG VHTFPAVLQS  180
SGLYSLSSVV TVPSSSLGTQ TYICNVNHKP SNTKVDKKVE PKSCDKTHTC PPCPAPELAG  240
APSVFLFPPK PKDTLMISRT PEVTCVVVDV SHEDPEVKFN WYVDGVEVHN AKTKPREEQY  300
NSTYRVVSVL TVLHQDWLNG KEYKCKVSNK ALPAPIEKTI SKAKGQPREP QVYTLPPSRD  360
ELTKNQVSLT CLVKGFYPSD IAVEWESNGQ PENNYKTTPP VLDSDGSFFL YSKLTVDKSR  420
WQQGNVFSCS VLHEALHSHY TQKSLSLSPG                                  450

SEQ ID NO: 3           moltype = AA  length = 219
FEATURE                Location/Qualifiers
```

```
source                  1..219
                        mol_type = protein
                        organism = synthetic construct
SEQUENCE: 3
DVVMTQSPLS LPVTPGEPAS ISCRSSQSLA KSYGNTYLSW YLQKPGQSPQ LLIYGISNRF    60
SGVPDRFSGS GSGTDFTLKI SRVEAEDVGV YYCLQGTHQP YTFGQGTKVE IKRTVAAPSV   120
FIFPPSDEQL KSGTASVVCL LNNFYPREAK VQWKVDNALQ SGNSQESVTE QDSKDSTYSL   180
SSTLTLSKAD YEKHKVYACE VTHQGLSSPV TKSFNRGEC                          219

SEQ ID NO: 4            moltype = AA    length = 451
FEATURE                 Location/Qualifiers
source                  1..451
                        mol_type = protein
                        organism = synthetic construct
SEQUENCE: 4
QVQLVQSGAE VKKPGASVKV SCKGSGYTFT SYWMHWVRQA PGQRLEWIGE IDPSESNTNY    60
NQKFKGRVTL TVDISASTAY MELSSLRSED TAVYYCARGG YDGWDYAIDY WGQGTLVTVS   120
SASTKGPSVF PLAPSSKSTS GGTAALGCLV KDYFPEPVTV SWNSGALTSG VHTFPAVLQS   180
SGLYSLSSVV TVPSSSLGTQ TYICNVNHKP SNTKVDKKVE PKSCDKTHTC PPCPAPELAG   240
APSVFLFPPK PKDTLMISRT PEVTCVVVDV SHEDPEVKFN WYVDGVEVHN AKTKPREEQY   300
NSTYRVVSVL TVLHQDWLNG KEYKCKVSNK ALPAPIEKTI SKAKGQPREP QVYTLPPSRD   360
ELTKNQVSLT CLVKGFYPSD IAVEWESNGQ PENNYKTTPP VLDSDGSFFL YSKLTVDKSR   420
WQQGNVFSCS VMHEALHNHY TQKSLSLSPG K                                  451

SEQ ID NO: 5            moltype = AA    length = 219
FEATURE                 Location/Qualifiers
source                  1..219
                        mol_type = protein
                        organism = synthetic construct
SEQUENCE: 5
DVVMTQSPLS LPVTPGEPAS ISCRSSQSLA KSYGNTYLSW YLQKPGQSPQ LLIYGISNRF    60
SGVPDRFSGS GSGTDFTLKI SRVEAEDVGV YYCLQGTHQP YTFGQGTKVE IKRTVAAPSV   120
FIFPPSDEQL KSGTASVVCL LNNFYPREAK VQWKVDNALQ SGNSQESVTE QDSKDSTYSL   180
SSTLTLSKAD YEKHKVYACE VTHQGLSSPV TKSFNRGEC                          219

SEQ ID NO: 6            moltype = AA    length = 5
FEATURE                 Location/Qualifiers
source                  1..5
                        mol_type = protein
                        organism = synthetic construct
SEQUENCE: 6
SYWMH                                                                 5

SEQ ID NO: 7            moltype = AA    length = 17
FEATURE                 Location/Qualifiers
source                  1..17
                        mol_type = protein
                        organism = synthetic construct
SEQUENCE: 7
EIDPSESNTN YNQKFKG                                                   17

SEQ ID NO: 8            moltype = AA    length = 12
FEATURE                 Location/Qualifiers
source                  1..12
                        mol_type = protein
                        organism = synthetic construct
SEQUENCE: 8
GGYDGWDYAI DY                                                        12

SEQ ID NO: 9            moltype = AA    length = 16
FEATURE                 Location/Qualifiers
source                  1..16
                        mol_type = protein
                        organism = synthetic construct
SEQUENCE: 9
RSSQSLAKSY GNTYLS                                                    16

SEQ ID NO: 10           moltype = AA    length = 7
FEATURE                 Location/Qualifiers
source                  1..7
                        mol_type = protein
                        organism = synthetic construct
SEQUENCE: 10
GISNRFS                                                               7

SEQ ID NO: 11           moltype = AA    length = 9
FEATURE                 Location/Qualifiers
source                  1..9
                        mol_type = protein
```

```
                        organism = synthetic construct
SEQUENCE: 11
LQGTHQPYT                                                                      9

SEQ ID NO: 12           moltype = DNA  length = 1350
FEATURE                 Location/Qualifiers
source                  1..1350
                        mol_type = other DNA
                        organism = synthetic construct
SEQUENCE: 12
caggtccagc ttgtacaaag tggagctgaa gtcaaaaagc caggtgcctc cgtcaaagtg      60
tcttgcaaag gcagcggata tacctttaca tcctactgga tgcactgggt ccgtcaagct     120
cccgggcaaa gactggagtg gatcggagaa atcgacccta gtgaaagcaa caccaactat     180
aaccagaagt tcaagggccg ggtgaccctg accgtggaca tcagcgcaag cacggcttac     240
atggagctca gctctctgcg gtcagaggat acagcagtgt attattgtgc ccgtggcggc     300
tatgacggct gggattatgc catcgattac tggggccagg gtaccttgt gaccgtatct      360
agtgctagca ccaagggccc atcggtcttc cccctggcac cctcctccaa gagcacctct     420
gggggcacag cggccctggg ctgcctggtc aaggactact tccccgaacc ggtgacggtg     480
tcgtggaact caggcgccct gaccagcggc gtgcacacct tcccggccgt cctacagtcc     540
tcaggactct actccctcag cagcgtggtg accgtgccct ccagcagctt gggcacccag     600
acctacatct gcaacgtgaa tcacaagccc agcaacacca aggtggacaa gaaggttgag     660
cccaaatctt gtgacaaaac tcacacatgc ccaccgtgcc cagcacctga actggctggg     720
gcccgtcag tcttcctctt cccccccaaaa cccaaggaca ccctctatat cacccgggga   780
cctgaggtca catgcgtggt ggtggacgtg agccacgaag accctgaggt caagttcaac     840
tggtacgtgg acggcgtgga ggtgcataat gccaagacaa agccgcggga ggagcagtac     900
aacagcacgt accgtgtggt cagcgtcctc accgtcctgc accaggactg gctgaatgge     960
aaggagtaca agtgcaaggt ctccaacaaa gccctcccag cccccatcga aaaaccatc    1020
tccaaagcca agggcagccc cgagaaccag gtgtacaccc tgccccca tcccgggac      1080
gagctgacca agaaccaggt cagcctgacc tgcctggtca aaggcttcta tcccagcgac    1140
atcgccgtgg agtgggagag caatgggcag ccggagaaca actacaagac cacgcctccc   1200
gtgctggact ccgacggctc cttcttcctc tacagcaagc tcaccgtgga caagagcagg    1260
tggcagcagg ggaacgtctt ctcatgctcc gtgatgcatg aggctctgca caaccactac    1320
acgcagaaga gcctctccct gtctccgggc                                     1350

SEQ ID NO: 13           moltype = DNA  length = 657
FEATURE                 Location/Qualifiers
source                  1..657
                        mol_type = other DNA
                        organism = synthetic construct
SEQUENCE: 13
gacgtcgtta tgactcagag tcccctgtct ctgcccgtca cccctggcga accagcatcc      60
atttcctgta gaagttcaca aagcctcgcc aagtcttatg caacacgtac ctttcgtgg     120
tatcttcaaa agccgggtca atctcccca ctgttgatct acggcatcag caaccggttc     180
tctggcgtcc ctgatcgctt ctctgggagt ggcagcggaa cagacttcac actgaagatc     240
agcagggtcg aagctgagga cgttggggtt tactactgtc tgcaagggac acaccagcca     300
tatacctttg gcaaggcac caaggtggag atcaagcgta cggtggctgc accatctgtc    360
ttcatcttcc cgccatctga tgagcagttg aaatctggaa ctgcctctgt tgtgtgcctg     420
ctgaataact tctatcccag agaggccaaa gtacagtgga aggtggataa cgccctccaa     480
tcgggtaact cccaggagag tgtcacagag caggacagca aggacagcac ctacagcctc     540
agcagcaccc tgacgctgag caaagcagac tacgagaaac acaaagtcta cgcctgcgaa     600
gtcacccatc agggcctgag ctcgcccgtc acaaagagct tcaacagggg agagtgt       657

SEQ ID NO: 14           moltype = DNA  length = 1407
FEATURE                 Location/Qualifiers
source                  1..1407
                        mol_type = other DNA
                        organism = synthetic construct
SEQUENCE: 14
atgggatggt catgtatcat ccttttttctg gtagcaactg caactggagt acatagccag      60
gtccagcttg tacaaagtgg agctgaagtc aaaaagccag gtgcctccgt caaagtgtct     120
tgcaaaggca gcggatatac ctttacatcc tactggatgc actgggtccg tcaagctccc     180
gggcaaagac tggagtggat cggagaaatc gaccctagtg aaagcaacac caactataac     240
cagaagttca agggccgggt gaccctgacc gtggacatca gcgcaagcac ggcttacatg     300
gagctcagct ctctgcggtc agaggataca gcagtgtatt attgtgcccg tggcggctat     360
gacggctggg attatgccat cgattactgg ggccagggta ccttgtgac cgtatctagt      420
gctagcacca agggcccatc ggtcttcccc ctggcaccct cctccaagag cacctctggg     480
ggcacagcgg ccctgggctg cctggtcaag gactacttcc ccgaaccggt gacggtgtcg     540
tggaactcag gcgccctgac cagcggcgtg cacaccttcc cggccgtcct acagtcctca     600
ggactctact ccctcagcag cgtggtgacc gtgccctcca gcagcttggg cacccagacc     660
tacatctgca acgtgaatca caagcccagc aacaccaagg tggacaagaa ggttgagccc     720
aaatcttgtg acaaaactca cacatgccca ccgtgcccag cacctgaact ggctggggcc     780
ccgtcagtct tcctcttccc cccaaaaccc aaggacaccc tctacatcac ccgggagcct     840
gaggtcacat gcgtggtggt ggacgtgagc cacgaagacc ctgaggtcaa gttcaactgg     900
tacgtggacg gcgtggaggt gcataatgcc aagacaaagc cgcgggagga gcagtacaac     960
agcacgtacc gtgtggtcag cgtcctcacc gtcctgcacc aggactggct gaatggcaag    1020
gagtacaagt gcaaggtctc caacaaagcc ctcccagccc ccatcgagaa aaccatctcc    1080
aaagccaaag gcagccccg agaaccacag gtgtacaccc tgccccatc ccgggacgag    1140
ctgaccaaga accaggtcag cctgacctgc ctggtcaaag gcttctatcc cagcgacatc    1200
gccgtggagt gggagagcaa tgggcagccg gagaacaact acaagaccac gcctcccgtg    1260
```

```
ctggactccg acggctcctt cttcctctac agcaagctca ccgtggacaa gagcaggtgg    1320
cagcagggga acgtcttctc atgctccgtg atgcatgagg ctctgcacaa ccactacacg    1380
cagaagagcc tctccctgtc tccgggc                                        1407

SEQ ID NO: 15           moltype = DNA  length = 1410
FEATURE                 Location/Qualifiers
source                  1..1410
                        mol_type = other DNA
                        organism = synthetic construct
SEQUENCE: 15
atggagacag acacactcct gctatgggta ctgctgctct ggttccagg ctccaccggc       60
caggtccagc ttgtacaaag tggagctgaa gtcaaaaagc caggtgcctc cgtcaaagtg     120
tcttgcaaag gcagcggata tacctttaca tcctactgga tgcactgggt ccgtcaagct    180
cccggcaaa gactggagtg gatcgggaga atcgaccta gtgaaagcaa caccaactat      240
aaccagaagt tcaagggccg ggtgaccctg accgtggaca tcagcgcaag cacggcttac    300
atggagctca gctctctgcg gtcagaggat acagcagtgt attattgtgc ccgtggcggc    360
tatgacggct gggattatgc catcgattac tgggcagg gtacccttgt gaccgtatct     420
agtgctagca ccaagggccc atcggtcttc ccctggcac cctcctccaa gagcacctct    480
ggggggcacag cggccctggg ctgcctggtc aaggactact tccccgaacc ggtgacggtg   540
tcgtggaact caggcgccct gaccagcggc gtgcacacct tcccggccgt cctacagtcc   600
tcaggactct actccctcag cagcgtggtg accgtgccct ccagcagctt gggcacccag   660
acctacatct gcaacgtgaa tcacaagccc agcaacacca aggtggacaa gaaggttgag   720
cccaaatctt gtgacaaaac tcacacatgc ccaccgtgcc cagcacctga actggctggg   780
gccccgtcag tcttcctctt ccccccaaaa cccaaggaca ccctctacat cacccggag    840
cctgaggtca catgcgtggt ggtggacgtg agccacgaag accctgaggt caagttcaac   900
tggtacgtgg acggcgtgga ggtgcataat gccaagacaa agccgcggga ggagcagtac   960
aacagcacgt accgtgtggt cagcgtcctc accgtcctgc accaggactg gctgaatggc  1020
aaggagtaca agtgcaaggt ctccaacaaa gccctcccag cccccatcga gaaaaccatc  1080
tccaaagcca aagggcagcc ccgagaacca caggtgtaca ccctgccccc atcccgggac  1140
gagctgacca agaaccaggt cagcctgacc tgcctggtca aaggcttcta tcccagcgac  1200
atcgccgtgg agtgggagag caatgggcag ccggagaaca actacaagac cacgcctccc  1260
gtgctggact ccgacggctc cttcttcctc tacagcaagc tcaccgtgga caagagcagg  1320
tggcagcagg ggaacgtctt ctcatgctcc gtgatgcatg aggctctgca caaccactac  1380
acgcagaaga gcctctccct gtctccgggc                                    1410

SEQ ID NO: 16           moltype = DNA  length = 1407
FEATURE                 Location/Qualifiers
source                  1..1407
                        mol_type = other DNA
                        organism = synthetic construct
SEQUENCE: 16
atgggggtcaa ccgccatcct tggcctcctc ctggctgttc tccaaggagt ctgtgcccag      60
gtccagcttg tacaaagtgg agctgaagtc aaaaagccag gtgcctccgt caaagtgtct    120
tgcaaaggca gcggatatac ctttacatcc tactggatgc actgggtccg tcaagctccc    180
gggcaaagac tggagtggat cggagaaatc gaccctagtg aaagcaacac caactataac    240
cagaagttca agggccgggt gaccctgacc gtggacatca gcgcaagcac ggcttacatg    300
gagctcagct ctctgcggtc agaggataca gcagtgtatt attgtgcccg tggcggctat    360
gacggctggg attatgccat cgattactgg ggccagggta cccttgtgac cgtatctagt    420
gctagcacca agggcccatc ggtcttcccc ctggcaccct cctccaagag cacctctggg    480
ggcacagcgg ccctgggctg cctggtcaag gactacttcc ccgaaccggt gacggtgtcg    540
tggaactcag gcgccctgac cagcggcgtg cacaccttcc cggccgtcct acagtcctca    600
ggactctact ccctcagcag cgtggtgacc gtgccctcca gcagcttggg cacccagacc    660
tacatctgca acgtgaatca caagcccagc aacaccaagg tggacaagaa ggttgagccc    720
aaatcttgtg acaaaactca cacatgccca ccgtgcccag cacctgaact ggctggggcc    780
ccgtcagtct tcctcttccc cccaaaaccc aaggacaccc tctacatcac ccggaggcct    840
gaggtcacat gcgtggtggt ggacgtgagc cacgaagacc ctgaggtcaa gttcaactgg    900
tacgtggacg gcgtggaggt gcataatgcc aagacaaagc cgcgggagga gcagtacaac    960
agcacgtacc gtgtggtcag cgtcctcacc gtcctgcacc aggactggct gaatggcaag   1020
gagtacaagt gcaaggtctc caacaaagcc ctcccagccc ccatcgagaa aaccatctcc   1080
aaagccaaag ggcagccccg agaaccacag gtgtacaccc tgcccccatc ccgggacgag   1140
ctgaccaaga accaggtcag cctgacctgc ctggtcaaag gcttctatcc cagcgacatc   1200
gccgtggagt gggagagcaa tgggcagccg gagaacaact acaagaccac gcctcccgtg   1260
ctggactccg acggctcctt cttcctctac agcaagctca ccgtggacaa gagcaggtgg   1320
cagcagggga acgtcttctc atgctccgtg atgcatgagg ctctgcacaa ccactacacg   1380
cagaagagcc tctccctgtc tccgggc                                       1407

SEQ ID NO: 17           moltype = DNA  length = 717
FEATURE                 Location/Qualifiers
source                  1..717
                        mol_type = other DNA
                        organism = synthetic construct
SEQUENCE: 17
atggagacag acacactcct gctatgggta ctgctgctct ggttccagg ctccaccggc       60
gacgtcgtta tgactcagag tccccctgtct ctgcccgtca ccctggcga accagcatcc    120
atttcctgta gaagttcaca aagcctcgcc agtcttatg caacacgta cctttcgtgg      180
tatcttcaaa agccgggtca atctcccaa ctgttgatct acggcatcag caaccggttc     240
tctgcgtcc ctgatcgctt ctctgggagt ggcagcggaa cagacttcac actgaagatc     300
agcagggctcg aagctgagga cgttggggtt tactactgtc tgcaagggac acaccagcca   360
tatccctttg gcaaggcac caaggtggag atcaagcgta cggtggctgc accatctgtc    420
```

```
ttcatcttcc cgccatctga tgagcagttg aaatctggaa ctgcctctgt tgtgtgcctg    480
ctgaataact tctatcccag agaggccaaa gtacagtgga aggtggataa cgccctccaa    540
tcgggtaact cccaggagag tgtcacagag caggacagca aggacagcac ctacagcctc    600
agcagcaccc tgacgctgag caaagcagac tacgagaaac acaaagtcta cgcctgcgaa    660
gtcacccatc agggcctgag ctcgcccgtc acaaagagct tcaacagggg agagtgt       717
```